US009913838B2

(12) United States Patent
Chen

(10) Patent No.: US 9,913,838 B2
(45) **Date of Patent: *Mar. 13, 2018**

(54) METHODS OF TREATING CANCER USING COMPOSITIONS COMPRISING PERILLYL ALCOHOL DERIVATIVE

(71) Applicant: NEONC TECHNOLOGIES INC., Los Angeles, CA (US)

(72) Inventor: Thomas Chen, La Canada, CA (US)

(73) Assignee: NeOnc Technologies, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/026,649

(22) PCT Filed: Oct. 8, 2014

(86) PCT No.: PCT/US2014/059600

§ 371 (c)(1),
(2) Date: Apr. 1, 2016

(87) PCT Pub. No.: WO2015/054333

PCT Pub. Date: Apr. 16, 2015

(65) Prior Publication Data

US 2016/0243114 A1 Aug. 25, 2016

Related U.S. Application Data

(63) Continuation-in-part of application No. 14/455,293, filed on Aug. 8, 2014, which is a continuation of application No. 13/566,731, filed on Aug. 3, 2012, now Pat. No. 8,916,545, which is a continuation of application No. PCT/US2011/049392, filed on Aug. 26, 2011.

(60) Provisional application No. 61/471,402, filed on Apr. 4, 2011, provisional application No. 61/377,747, filed on Aug. 27, 2010, provisional application No. 61/888,253, filed on Oct. 8, 2013.

(51) Int. Cl.

| | |
|---|---|
| ***A61K 31/495*** | (2006.01) |
| ***A61K 47/54*** | (2017.01) |
| ***A61K 47/55*** | (2017.01) |
| *A61K 9/00* | (2006.01) |

(52) U.S. Cl.

CPC ............ *A61K 31/495* (2013.01); *A61K 47/54* (2017.08); *A61K 47/55* (2017.08); *A61K 9/0043* (2013.01); *A61K 9/0085* (2013.01)

(58) Field of Classification Search

None

See application file for complete search history.

(56) References Cited

U.S. PATENT DOCUMENTS

| | | | |
|---|---|---|---|
| 6,378,819 | B1 | 4/2002 | Johnson |
| 2003/0177609 | A1 | 9/2003 | Bigolin |
| 2006/0029586 | A1 | 2/2006 | Chen |
| 2006/0104997 | A1 | 5/2006 | Constanides |
| 2006/0225001 | A1 | 10/2006 | Sylthe |
| 2008/0319039 | A1 | 12/2008 | Bersch |
| 2010/0112780 | A1 | 5/2010 | Thompson et al. |
| 2012/0184560 | A1 | 7/2012 | Wong et al. |
| 2013/0210877 | A1 | 8/2013 | Chen et al. |
| 2014/0364472 | A1 | 12/2014 | Chen |

FOREIGN PATENT DOCUMENTS

| | | | |
|---|---|---|---|
| JP | 2009510171 | | 3/2009 |
| JP | 2010-65038 | | 3/2010 |
| JP | 2010520216 | | 6/2010 |
| WO | 2007041637 | | 4/2007 |
| WO | 2008109333 | | 9/2008 |
| WO | WO2010/091198 | * | 8/2010 |

OTHER PUBLICATIONS

Braun et al. (Drug, Design, Development and Therapy (2008), vol. 2, pp. 289-301).*

Addeo et al. (Cancer (2008) vol. 112 pp. 2524-2531).*

Vogelstein et al. (Nature Medicine (2004), vol. 10, pp. 789-799).*

Holland Progenitor cells and glioma formation. Curr. Opin. Neurology, 2001, 14: 683-688.*

Healthcommunities.com [online] Retrieved on Feb. 2, 2017 Retrieved from the internet <url:http://www.healthcommunities.com/nervous-system-tumors/other-treatment.shtml>.*

Chen; et al., "Green tea epigallocatechin gallate enhances therapeutic efficacy of temozolomide in orthotopic mouse glioblastoma models", Cancer Lett. (Mar. 2011), 302(2):100-8.

Crow et al. (1994) L Med. Chem. 37(19):3191-3194.

Henry et al., A Pharmacokinetic study of midazolam in dogs: nasal drop vs. atomizer administration, Pediatric Dentistry (1998), 20(5) 321-326.

Japanese Office Action dated Jun. 14, 2016 corresponding to Japanese Patent Application No. 2014-542593; 5 pages.

Otagiri, Masaki, Prodrug, New Drug Delivery System, CMC Co., Ltd. Shima Kentaro, 2000, p. 123-126.

(Continued)

*Primary Examiner* — Kendra D Carter

*Assistant Examiner* — Taina D Matos Negron

(74) *Attorney, Agent, or Firm* — Leason Ellis LLP

(57) ABSTRACT

A method for treating brain metastases of a cancer in a mammal includes administering to the mammal a therapeutically effective amount of a perillyl alcohol carbamate, such as TMZ-POH. The brain metastases can be originated or spread from breast cancer. The perillyl alcohol derivative may be perillyl alcohol conjugated with a therapeutic agent, such as a chemotherapeutic agent. The chemotherapeutic agents that may be used in the present invention include a DNA alkylating agent, a topoisomerase inhibitor, an endoplasmic reticulum stress inducing agent, a platinum compound, an antimetabolite, an enzyme inhibitor, and a receptor antagonist.

7 Claims, 21 Drawing Sheets

(56) References Cited

OTHER PUBLICATIONS

B. Brennan, Nasopharyngeal carcinoma, Orphanet J Rare Dis 1 (2006) 23.

S.M. Cao, et al., The prevalence and prevention of nasopharyngeal carcinoma in China, Chin J Cancer 30 (2011) 114-119.

Wei, et al. nasopharyngeal carcinoma. Lancet 365 (2005) 2041-2054.

J. Tsang et al., Novel Therapy for nasopharyngeal carcinoma—where are we. Oral Oncol 50 (2014) 798-801.

L. Jang-Chun et al., Comparisons of quality of life for patients with nasopharyngeal carcinoma after treatment with: different RT technologies, Acta Otorhinolaryngol Ital 34 (2014) 241-246.

Lin et al., Characterization of seven newly established nasopharyngeal carcinoma cell lines, Lab Invest 68 (1993)'16-727.

Wu et al., Nucleolin antisense oligodeoxynucleotides induce apoptosis and may be used as a potential drug fornasopharyngeal carcinoma therapy, Oncol. Rep. 27 (2012) 94-100.

Intenational Search Report and Written Opinion dated Jan. 19, 2016 corresponding to International Application No. PCT/US2015/057609; 2 pages.

Chen et al. Inhalational temozolomide—a new mode of treating malignant gliomas. Proceedings of the 103rd Annual Meeting of the American Association for Cancer Research 2012, Cancer Res. 72(8 Supply): Abstract No. 3893, 2012.

Cho et al. NEO212, Temozolomide Conjugated to Perillyl Alcohol, is a Novel Drug for Effective Treatment of a Broad Range of Temozolomide-Resistant Gliomas. Mol. Cancer Ther. 13(8):2004-2017, 2014.

International Search Report and Written Opinion dated Jan. 13, 2015 corresponding to International Patent Application No. PCT/US2014/059600; 8 pages.

* cited by examiner

Colony Forming Assay for TMZ and TMZ-POH on TMZ sensitive and resistant glioma cells – 72 hr treatment CFA of U251 and U251TR with POH – 72 hr treatment.

Western Blot following TMZ-POH treatment of U251-TMZs and U251-TMZr cells -18 hr treatment

METHODS OF TREATING CANCER USING COMPOSITIONS COMPRISING PERILLYL ALCOHOL DERIVATIVE

CROSS REFERENCE TO RELATED APPLICATIONS

This application is a national stage under 35 U.S.C. 371 based on and claiming the benefit of International Application PCT/US14/59600, filed on 8 Oct. 2014, incorporated by reference, which claims priority to U.S. Provisional Application No. 61/888,253, filed Oct. 8, 2013. This application also relates to U.S. application Ser. No. 14/455,293 filed Aug. 8, 2014, which is a continuation of U.S. application Ser. No. 13/566,731 filed Aug. 3, 2012, now U.S. Pat. No. 8,916,545, which is a continuation of International Application No. PCT/US2011/049392 filed Aug. 26, 2011, which claims priority to U.S. Provisional Application Nos. 61/377,747 (filed Aug. 27, 2010) and 61/471,402 (filed Apr. 4, 2011). The disclosures of all of these prior filed applications are incorporated by reference herein in their entireties.

FIELD OF THE INVENTION

The present invention relates to compositions of perillyl alcohol (POH) derivatives such as POH carbamates, as well as the use thereof for treating cancers.

BACKGROUND OF THE INVENTION

Malignant gliomas, the most common form of central nervous system (CNS) cancers, is currently considered essentially incurable. Among the various malignant gliomas, anaplastic astrocytomas (Grade III) and glioblastoma multiforme (GBM; Grade IV) have an especially poor prognosis due to their aggressive growth and resistance to currently available therapies. The present standard of care for malignant gliomas consists of surgery, ionizing radiation, and chemotherapy. Despite recent advances in medicine, the past 50 years have not seen any significant improvement in prognosis for malignant gliomas. Wen et al. Malignant gliomas in adults. *New England J Med.* 359: 492-507, 2008. Stupp et al. Radiotherapy plus concomitant and adjuvant temozolomide for glioblastoma. *New England J Med.* 352: 987-996, 2005.

The poor response of tumors, including malignant gliomas, to various types of chemotherapeutic agents are often due to intrinsic drug resistance. Additionally, acquired resistance of initially well-responding tumors and unwanted side effects are other problems that frequently thwart long-term treatment using chemotherapeutic agents. Hence, various analogues of chemotherapeutic agents have been prepared in an effort to overcome these problems. The analogues include novel therapeutic agents which are hybrid molecules of at least two existing therapeutic agents. For example, cisplatin has been conjugated with Pt-(II) complexes with cytotoxic codrugs, or conjugated with bioactive shuttle components such as porphyrins, bile acids, hormones, or modulators that expedite the transmembrane transport or the drug accumulation within the cell. (6-Aminomethylnicotinate) dichloridoplatinum(II) complexes esterified with terpene alcohols were tested on a panel of human tumor cell lines. The terpenyl moieties in these complexes appeared to fulfill a transmembrane shuttle function and increased the rate and extent of the uptake of these conjugates into various tumor cell lines. Schobert et al. Monoterpenes as Drug Shuttles: Cytotoxic (6-minomethylnicotinate) dichloridoplatinum(II) Complexes with Potential To Overcome Cisplatin Resistance. *J. Med. Chem.* 2007, 50, 1288-1293.

Metastasized cancer, such as breast cancer, that has spread to the brain poses a similarly serious therapeutic challenge as malignant gliomas. This challenge once was a late aspect of disease progression, but increasingly is becoming a first site of disease progression after otherwise successful treatment of primary tumor and metastases outside the cranium. Traditional breast cancer therapeutics, such as paclitaxel or doxorubicin, only reach brain metastases at concentrations that are far lower than needed to be therapeutically active. P. R. Lockman, et al. Heterogeneous blood-tumor barrier permeability determines drug efficacy in experimental brain metastases of breast cancer, *Clin Cancer Res* 16 (2010) 5664-5678. The most critical barrier to effective entry of chemotherapeutics into the brain is the blood brain barrier (BBB), and very few anticancer drugs are able to overcome this obstacle. E. Fokas, J. P. Steinbach, C. Rodel, Biology of brain metastases and novel targeted therapies: time to translate the research, *Biochim Biophys Acta* 1835 (2013) 61-75.

Perillyl alcohol (POH), a naturally occurring monoterpene, has been suggested to be an effective agent against a variety of cancers, including CNS cancer, breast cancer, pancreatic cancer, lung cancer, melanomas and colon cancer. Gould, M. Cancer chemoprevention and therapy by monoterpenes. *Environ Health Perspect.* 1997 June; 105 (Suppl 4): 977-979. Hybrid molecules containing both perillyl alcohol and retinoids were prepared to increase apoptosis-inducing activity. Das et al. Design and synthesis of potential new apoptosis agents: hybrid compounds containing perillyl alcohol and new constrained retinoids. *Tetrahedron Letters* 2010, 51, 1462-1466.

The alkylating agent temozolomide (TMZ) is able to cross the BBB after oral dosing and has become the chemotherapeutic standard of care for patients with glioblastoma multiforme (GBM). Zhang et al. Temozolomide: mechanisms of action, repair and resistance. *Curr Mol Pharmacol* 5 (2012) 102-114. TMZ acts as a prodrug. Its mechanism of activation involves hydrolytic opening of its tetrazinone ring, which takes places spontaneously in aqueous solution at 37° C., and does not require the participation of cellular enzymes. The resulting product, the unstable monomethyl MTIC (5-(3-methyltriazen-1-yl)-imidazole-4-carboxamide), reacts with water to liberate AIC (4-amino-5-imidazole-carboxamide) and the highly reactive methyldiazonium cation, which methylates DNA purine residues.

When TMZ was tested for activity against brain metastatic breast cancer in heavily pretreated patients, it revealed mixed outcomes that ranged from "encouraging activity" and "disease control" to "well-tolerated, but no objective responses". C. Christodoulou et al., Phase II study of temozolomide in heavily pretreated cancer patients with brain metastases, *Annals Oncol* 12 (2001) 249-254; L. E. Abrey et al., A phase II trial of temozolomide for patients with recurrent or progressive brain metastases, *J Neurooncol* 53 (2001) 259-265; M. E. Trudeau et al., Temozolomide in metastatic breast cancer (MBC): a phase II trial of the National Cancer Institute of Canada-Clinical Trials Group (NCIC-CTG) *Annals Oncol* 17 (2006) 952-956; R. Addeo et al. Phase 2 trial of temozolomide using protracted low-dose and whole-brain radiotherapy for nonsmall cell lung cancer and breast cancer patients with brain metastases, *Cancer* 113 (2008) 2524-2531; S. Siena et al., Dose-dense temozolomide regimen for the treatment of brain metastases from melanoma, breast cancer, or lung cancer not amenable to surgery or radiosurgery: a multicenter phase II study. *Annals*

*Oncol* 21 (2010) 655-661; R. Addeo et al., Protracted low dose of oral vinorelbine and temozolomide with whole-brain radiotherapy in the treatment for breast cancer patients with brain metastases, *Cancer Chemother Pharmacol* 70 (2012) 603-609. The underlying basis for these inconsistent results was not investigated, but it is conceivable that these differences may have been due to variable expression levels of O6-methylguanine-DNA methyltransferase (MGMT; also called O6-alkylguanine-DNA alkyltransferase, AGT), a DNA repair enzyme that removes alkyl groups located on the O6-position of guanine A. E. Pegg, Multifaceted roles of alkyltransferase and related proteins in DNA repair, DNA damage, resistance to chemotherapy, and research tools, *Chem Res Toxicol* 24 (2011) 618-639; M. Christmann et al., O(6)-Methylguanine-DNA methyltransferase (MGMT) in normal tissues and tumors: enzyme activity, promoter methylation and immunohistochemistry, *Biochim Biophys Acta* 1816 (2011) 179-190. Because the primary toxic DNA lesion set by TMZ is alkylation of O6-guanine, high expression levels of MGMT protect tumor cells from the cytotoxic impact of TMZ and provide treatment resistance. J. R. Silber et al., O(6)-methylguanine-DNA methyltransferase in glioma therapy: promise and problems, *Biochim Biophys Acta* 1826 (2012) 71-82; A. V. Knizhnik et al., Survival and death strategies in glioma cells: autophagy, senescence and apoptosis triggered by a single type of temozolomide-induced DNA damage, *PLoS One* 8 (2013) e55665. When MGMT expression was investigated in breast cancer metastases to the brain, it was found that over half of the intracranial lesions analyzed were strongly positive for MGMT immunoreactivity. B. Ingold et al., Homogeneous MGMT immunoreactivity correlates with an unmethylated MGMT promoter status in brain metastases of various solid tumors, *PLoS One* 4 (2009) e4775.

MGMT activity is unusual in that it represents a "suicide" mechanism, whereby acceptance of the alkyl group from DNA irreversibly inactivates the enzyme and leads to its rapid degradation. This feature is exploited by the use of specific MGMT inhibitors, such as O6-benzylguanine (O6-BG), which act as pseudosubstrates. B. Kaina, et al. Targeting O(6)-methylguanine-DNA methyltransferase with specific inhibitors as a strategy in cancer therapy, *Cell Mol Life Sci* 67 (2010) 3663-3681. Benzylation of MGMT via reaction with O6-BG causes the same structural change in the enzyme as that seen after alkylation following DNA repair, and therefore also leads to rapid degradation of the protein. A. E. Pegg, et al., Use of antibodies to human O6-alkylguanine-DNA alkyltransferase to study the content of this protein in cells treated with O6-benzylguanine or N-methyl-N'-nitro-N-nitrosoguanidine, *Carcinogenesis* 12 (1991) 1679-1683. Ablation of MGMT activity after treatment of MGMT-positive cells with O6-BG generally increases their sensitivity to killing by TMZ, and this has been well established in numerous in vitro and in vivo tumor models. However, a recent phase-II clinical trial yielded mixed outcomes when O6-BG and TMZ were administered to brain cancer patients with TMZ-resistant tumors: while the addition of the MGMT inhibitor restored TMZ-sensitivity in a fraction (16%) of patients with anaplastic glioma, there was no significant effect (3%) in patients with GBM. J. A. Quinn, et al., Phase II trial of temozolomide plus o6-benzylguanine in adults with recurrent, temozolomide-resistant malignant glioma, *J Clin Oncol* 27 (2009) 1262-1267. While the underlying reasons for this disappointing outcome remain to be established, the limited response documented in this trial does not generate enthusiasm for the potential study of this drug combination in brain metastatic breast cancer patients.

There is a need to prepare effective therapeutic agents and methods of use thereof in the treatment of cancers such as malignant gliomas and other cancers metastasized in the brain.

SUMMARY OF THE INVENTION

The invention provides for a method for treating brain metastases of a cancer in a mammal, comprising delivering to the mammal a therapeutically effective amount of a perillyl alcohol derivative, such as a perillyl alcohol carbamate. The invention also provides for a method for treating a metastatic cancer of a mammal that has spread to the brain by delivering to the mammal a therapeutically effective amount of a perillyl alcohol derivative, such as a perillyl alcohol carbamate.

The perillyl alcohol derivative may be perillyl alcohol conjugated with a therapeutic agent, such as a chemotherapeutic agent. The chemotherapeutic agents that may be used in the present invention include a DNA alkylating agent, a topoisomerase inhibitor, an endoplasmic reticulum stress inducing agent, a platinum compound, an antimetabolite, an enzyme inhibitor, and a receptor antagonist. In certain embodiments, the therapeutic agent can be temozolomide (TMZ). The perillyl alcohol carbamate may be 3-methyl 4-oxo-3,4-dihydroimidazo[5,1-d][1,2,3,5]tetrazine-8-carbonyl)-carbamic acid-4-isopropenyl cyclohex-1-enylmethyl ester (TMZ-POH).

The method may further comprise treating the mammal with radiation before, during, or after the administration of the pharmaceutical composition, and/or further comprise delivering to the mammal another chemotherapeutic agent. The brain metastasis or metastases to be treated can originate or spread from a cancer such as a systemic cancer, lung cancer, prostate cancer, breast cancer, hematopoietic cancer, ovarian cancer, bladder cancer, germ cell tumors, kidney cancer, leukemia, lymphoma, and melanoma. In one embodiment, the brain metastases originate or are spread from metastatic breast cancer.

The routes of administration of the perillyl alcohol derivative include inhalation, intranasal, oral, intravenous, subcutaneous or intramuscular administration. In some embodiments, the perillyl alcohol derivative can be administered intranasally using a nasal delivery device selected from the group consisting of an intranasal inhaler, an intranasal spray device, an atomizer, a nebulizer, a metered dose inhaler (MDI), a pressurized dose inhaler, an insufflator, a unit dose container, a pump, a dropper, a nasal spray bottle, a squeeze bottle and a bi-directional device.

BRIEF DESCRIPTION OF THE DRAWINGS

FIG. 9A shows the images of subcutaneous U-87 gliomas in nude mice treated with butyryl-POH, purified (S)-perillyl alcohol having a purity greater than 98.5% ("Purified POH"), POH purchased from Sigma chemicals ("Sigma"), or phosphate buffered saline ("PBS"; negative control). FIG. 9B shows average tumor growth over time (total time period of 60 days).

In FIG. 20A, cells were exposed for 48 hours to increasing concentrations of TMZ (diamonds), TMZ-POH (circles), POH (triangles), or equimolar concentrations of TMZ plus POH (squares). Colony formation by control cells (treated with vehicle only) is set at 1; graphs display mean (±SD) from ≥3 independent experiments. In FIG. 20B, cells were exposed to 10 μM TMZ-POH, TMZ, or POH, or to 10 μM TMZ-POH or TMZ combined with 10 μM POH. Shown is a photo of one representative CFA.

FIG. 21A shows MGMT basal levels in the six breast cancer cell lines used in this study. FIG. 21B shows MGMT basal levels in three GBM cell lines compared to MCF7 breast cancer cells. In FIG. 21C, MDA-MB-468 cells were treated with the indicated concentrations of TMZ-POH, TMZ, or O6-BG for 17 hours before harvest of cellular lysates. vh.=cells treated with vehicle only.

In FIG. 22A, two individually selected clones, 231-MGMT-1 and -2, were analyzed by Western blot for basal level MGMT protein expression in comparison to parental cells. In FIG. 22B, 231-MGMT-1 and -2 were treated with increasing concentrations of TMZ-POH and TMZ for 48 hours, and cell survival was analyzed by CFA. Graph with 231-MGMT-1 cells displays mean (±SD) from 3 independent experiments; graph with 231-MGMT-2 cells shows the average from two independent experiments.

FIG. 23A shows colony survival of MDA-MB-231 cells; FIG. 23B shows MGMT-transfected 231-MGMT-2 cells, and FIG. 23C shows MDA-MB-468 cells. Shown is mean number of colonies (±SD) from ≥3 wells treated in parallel.

In FIG. 25A, cells were treated with 15 μM TMZ-POH and harvested every 24 hours up to 6 days; control cells remained untreated, or received vehicle (vh.) only. In FIG. 25B, cells were treated with 20 μM of either TMZ-POH, TMZ, or POH individually, or with 20 μM TMZ combined with 20 μM POH (TMZ+POH) and harvested after 24 hours or 5 days; control cells remained untreated, or received vehicle (vh.) only. In the case of caspase 7, only the activated (cleaved) form is shown (cl. C-7). In the case of PARP, the top panel shows both full-length and proteolytically cleaved forms of the protein, whereas the bottom panel only shows faster-migrating, cleaved PARP.

In FIG. 26A, cells were treated with 15 μM TMZ-POH or 30 μM TMZ for 30 min or 1, 2, 4, and 24 hours. Thereafter, drug-containing medium was removed, fresh medium (without drug) was added, and cells remained undisturbed until colony staining 12 days later. In FIG. 26B, cells were exposed to supernatant (i.e., the drug-containing medium removed from cells shown in FIG. 26A). The arrows indicate which cells received which supernatant. After 24 hours of incubation, all drug-containing medium was removed, fresh medium (without drug) was added, and cells remained undisturbed until colony staining 12 days later. FIG. 26C shows a representative 6-well plate with stained colonies. Left panel (untreated): control cells without drug treatment. Middle panel (0-24 h): Cells received 15 μM TMZ-POH or 30 μM TMZ for 24 hours. Right panel (1-25 h): TMZ-POH and TMZ were incubated in neutral buffer at 37° C. for 1 hour before addition to cells to a final concentration of 15 μM TMZ-POH and 30 μM TMZ for 24 hours.

In FIG. 27A, all surviving animals were imaged again on days 21, 28, and 36. The top panel shows one representative mouse from the vehicle-only treated group. Note 12-fold increased ROI radiance (representative of tumor growth) from 1.65E7 to 1.92E8 between days 10 and 21. The bottom panel shows a representative mouse from the group of TMZ-POH-treated animals. Here, radiance increased only 1.7-fold (from 1.11E7 to 1.92E7) between days 10 and 21, but reached 1.88E8 (similar to control mouse on day 21) by day 43. Heat bar to the right shows scale of radiance. FIG. 27B shows Kaplan-Meier survival plot of all animals carrying intracranial tumors. Arrow labeled Rx indicates the time period of treatment. Statistical difference between groups of TMZ-treated and TMZ-POH-treated animals: $p<0.001$.

DETAILED DESCRIPTION

Figure 1:
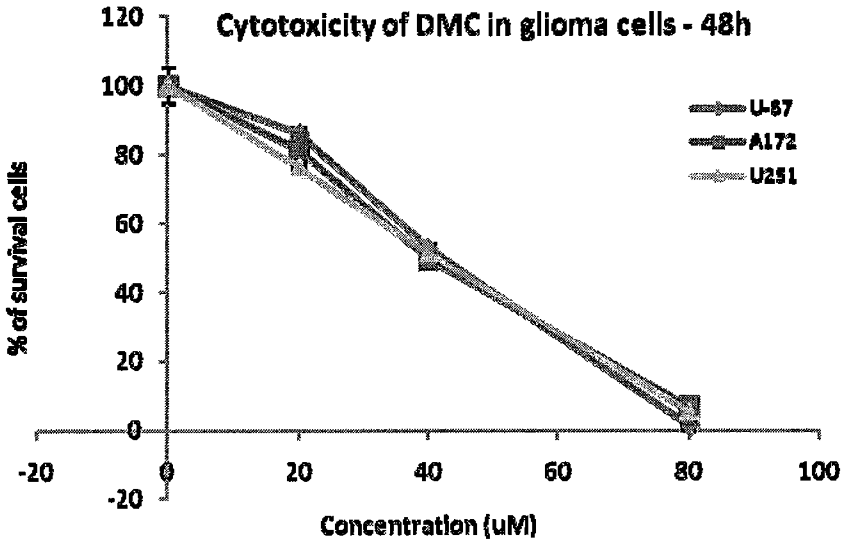
FIG. 1 shows the results of the MTT cytotoxicity assays demonstrating the efficacy of dimethyl celecoxib (DMC) in killing U87, A172 and U251 human glioma cells.

The present invention provides for a derivative of monoterpene or sesquiterpene, such as a perillyl alcohol derivative. The present invention also provides for a pharmaceutical composition comprising a derivative of monoterpene or sesquiterpene, such as a perillyl alcohol derivative.

For example, the perillyl alcohol derivative may be a perillyl alcohol carbamate. The perillyl alcohol derivative may be perillyl alcohol conjugated with a therapeutic agent such as a chemotherapeutic agent. The monoterpene (or sesquiterpene) derivative may be formulated into a pharmaceutical composition, where the monoterpene (or sesquiterpene) derivative is present in amounts ranging from about 0.01% (w/w) to about 100% (w/w), from about 0.1% (w/w) to about 80% (w/w), from about 1% (w/w) to about 70% (w/w), from about 10% (w/w) to about 60% (w/w), or from about 0.1% (w/w) to about 20% (w/w). The present compositions can be administered alone, or may be co-administered together with radiation or another agent (e.g., a chemotherapeutic agent), to treat a disease such as cancer. Treatments may be sequential, with the monoterpene (or sesquiterpene) derivative being administered before or after the administration of other agents. For example, a perillyl alcohol carbamate may be used to sensitize a cancer patient to radiation or chemotherapy. Alternatively, agents may be administered concurrently. The route of administration may vary, and can include, inhalation, intranasal, oral, transdermal, intravenous, subcutaneous or intramuscular injection. The present invention also provides for a method of treating a disease such as cancer, comprising the step of delivering to a patient a therapeutically effective amount of a derivative of monoterpene (or sesquiterpene).

The compositions of the present invention may contain one or more types of derivatives of monoterpene (or sesquiterpene). Monoterpenes include terpenes that consist of two isoprene units. Monoterpenes may be linear (acyclic) or contain rings. Derivatives of monoterpenoids are also encompassed by the present invention. Monoterpenoids may be produced by biochemical modifications such as oxidation or rearrangement of monoterpenes. Examples of monoterpenes and monoterpenoids include, perillyl alcohol (S(−)) and (R(+)), ocimene, myrcene, geraniol, citral, citronellol, citronellal, linalool, pinene, terpineol, terpinen, limonene, terpinenes, phellandrenes, terpinolene, terpinen-4-ol (or tea tree oil), pinene, terpineol, terpinen; the terpenoids such as p-cymene which is derived from monocyclic terpenes such as menthol, thymol and carvacrol; bicyclic monoterpenoids such as camphor, borneol and eucalyptol.

Monoterpenes may be distinguished by the structure of a carbon skeleton and may be grouped into acyclic monoterpenes (e.g., myrcene, (Z)- and (E)-ocimene, linalool, geraniol, nerol, citronellol, myrcenol, geranial, citral a, neral, citral b, citronellal, etc.), monocyclic monoterpenes (e.g., limonene, terpinene, phellandrene, terpinolene, menthol, carveol, etc.), bicyclic monoterpenes (e.g., pinene, myrtenol, myrtenal, verbanol, verbanon, pinocarveol, carene, sabinene, camphene, thujene, etc.) and tricyclic monoterpenes (e.g. tricyclene). See *Encyclopedia of Chemical Technology*, Fourth Edition, Volume 23, page 834-835.

Sesquiterpenes of the present invention include terpenes that consist of three isoprene units. Sesquiterpenes may be linear (acyclic) or contain rings. Derivatives of sesquiterpenoids are also encompassed by the present invention. Sesquiterpenoids may be produced by biochemical modifications such as oxidation or rearrangement of sesquiterpenes. Examples of sesquiterpenes include farnesol, farnesal, farnesylic acid and nerolidol.

The derivatives of monoterpene (or sesquiterpene) include, but are not limited to, carbamates, esters, ethers, alcohols and aldehydes of the monoterpene (or sesquiterpene). Monoterpene (or sesquiterpene) alcohols may be derivatized to carbamates, esters, ethers, aldehydes or acids.

Chloroformate

Carbamate refers to a class of chemical compounds sharing the functional group

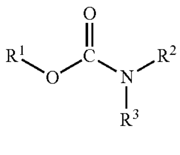

based on a carbonyl group flanked by an oxygen and a nitrogen. $R^1$, $R^2$ and $R^3$ can be a group such as alkyl, aryl, etc., which can be substituted. The R groups on the nitrogen and the oxygen may form a ring. $R^1$—OH may be a monoterpene, e.g., POH. The $R^2$—N—$R^3$ moiety may be a therapeutic agent.

Carbamates may be synthesized by reacting isocyanate and alcohol, or by reacting chloroformate with amine. Carbamates may be synthesized by reactions making use of phosgene or phosgene equivalents. For example, carbamates may be synthesized by reacting phosgene gas, diphosgene or a solid phosgene precursor such as triphosgene with two amines or an amine and an alcohol. Carbamates (also known as urethanes) can also be made from reaction of a urea intermediate with an alcohol. Dimethyl carbonate and diphenyl carbonate are also used for making carbamates. Alternatively, carbamates may be synthesized through the reaction of alcohol and/or amine precursors with an ester-substituted diaryl carbonate, such as bismethylsalicylcarbonate (BMSC). U.S. Patent Publication No. 20100113819.

Carbamates may be synthesized by the following approach:

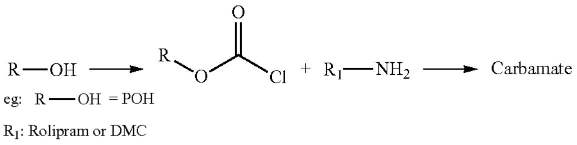

Suitable reaction solvents include, but are not limited to, tetrahydrofuran, dichloromethane, dichloroethane, acetone, and diisopropyl ether. The reaction may be performed at a temperature ranging from about −70° C. to about 80° C., or from about −65° C. to about 50° C. The molar ratio of perillyl chloroformate to the substrate R—$NH_2$ may range from about 1:1 to about 2:1, from about 1:1 to about 1.5:1, from about 2:1 to about 1:1, or from about 1.05:1 to about 1.1:1. Suitable bases include, but are not limited to, organic bases, such as triethylamine, potassium carbonate, N,N'-diisopropylethylamine, butyl lithium, and potassium-t-butoxide.

Alternatively, carbamates may be synthesized by the following approach:

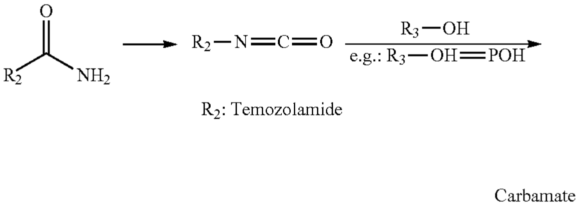

Suitable reaction solvents include, but are not limited to, dichloromethane, dichloroethane, toluene, diisopropyl ether, and tetrahydrofuran. The reaction may be performed at a temperature ranging from about 25° C. to about 110° C., or from about 30° C. to about 80° C., or about 50° C. The molar ratio of perillyl alcohol to the substrate R—N═C═O may range from about 1:1 to about 2:1, from about 1:1 to about 1.5:1, from about 2:1 to about 1:1, or from about 1.05:1 to about 1.1:1.

Esters of the monoterpene (or sesquiterpene) alcohols of the present invention can be derived from an inorganic acid or an organic acid. Inorganic acids include, but are not limited to, phosphoric acid, sulfuric acid, and nitric acid. Organic acids include, but are not limited to, carboxylic acid such as benzoic acid, fatty acid, acetic acid and propionic acid, and any therapeutic agent bearing at least one carboxylic acid functional group Examples of esters of monoterpene (or sesquiterpene) alcohols include, but are not limited to, carboxylic acid esters (such as benzoate esters, fatty acid esters (e.g., palmitate ester, linoleate ester, stearate ester, butyryl ester and oleate ester), acetates, propionates (or propanoates), and formates), phosphates, sulfates, and carbamates (e.g., N,N-dimethylaminocarbonyl).

A specific example of a monoterpene that may be used in the present invention is perillyl alcohol (commonly abbreviated as POH). The derivatives of perillyl alcohol include, perillyl alcohol carbamates, perillyl alcohol esters, perillic aldehydes, dihydroperillic acid, perillic acid, perillic aldehyde derivatives, dihydroperillic acid esters and perillic acid esters. The derivatives of perillyl alcohol may also include its oxidative and nucleophilic/electrophilic addition derivatives. U.S. Patent Publication No. 20090031455. U.S. Pat. Nos. 6,133,324 and 3,957,856. Many examples of derivatives of perillyl alcohol are reported in the chemistry literature (see Appendix A: CAS Scifinder search output file, retrieved Jan. 25, 2010).

In certain embodiments, a POH carbamate is synthesized by a process comprising the step of reacting a first reactant of perillyl chloroformate with a second reactant such as dimethyl celocoxib (DMC), temozolomide (TMZ) and rolipram. The reaction may be carried out in the presence of tetrahydrofuran and a base such as n-butyl lithium. Perillyl chloroformate may be made by reacting POH with phosgene. For example, POH conjugated with temozolomide through a carbamate bond may be synthesized by reacting temozolomide with oxalyl chloride followed by reaction with perillyl alcohol. The reaction may be carried out in the presence of 1,2-dichloroethane.

POH carbamates encompassed by the present invention include, but not limited to, 4-(bis-N,N'-4-isopropenyl cyclohex-1-enylmethyloxy carbonyl [5-(2,5-dimethyl phenyl)-3-trifluoromethyl pyrazol-1-yl]benzenesulfonamide, 4-(3-cyclopentyloxy-4-methoxy phenyl)-2-oxo-pyrrolidine-1-carboxylic acid 4-isopropenyl cyclohex-1-enylmethyl ester, and (3-methyl 4-oxo-3,4-dihydroimidazo[5,1-d][1,2,3,5]tetrazine-8-carbonyl)carbamic acid-4-isopropenyl cyclohex-1-enylmethyl ester. The details of the chemical reactions generating these compounds are described in the Examples below.

In certain embodiments, perillyl alcohol derivatives may be perillyl alcohol fatty acid esters, such as palmitoyl ester of POH and linoleoyl ester of POH, the chemical structures of which are shown below.

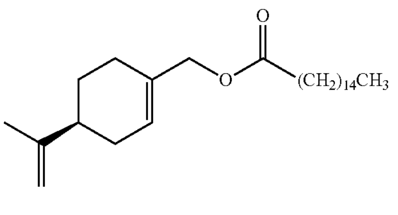

Hexadecanoic acid 4-isopropenyl-cyclohex-1-enylmethyl ester (Palmitoyl ester of POH)

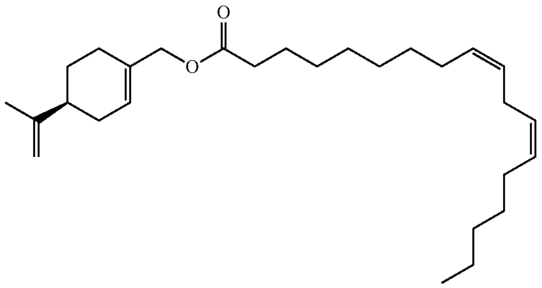 [SMILES: C=C(C)[C@@H]1CC=C(COC(=O)CCCCCCC/C=C\C/C=C\CCCCC)CC1]

Octadeca-9, 12-dienoic acid 4-isopropenyl-cyclohex-1-enylmethyl ester (Linoleoyl ester of POH)

The monoterpene (or sesquiterpene) derivative may be a monoterpene (or sesquiterpene) conjugated with a therapeutic agent. A monoterpene (or sesquiterpene) conjugate encompassed by the present invention is a molecule having a monoterpene (or sesquiterpene) covalently bound via a chemical linking group to a therapeutic agent. The molar ratio of the monoterpene (or sesquiterpene) to the therapeutic agent in the monoterpene (or sesquiterpene) conjugate may be 1:1, 1:2, 1:3, 1:4, 2:1, 3:1, 4:1, or any other suitable molar ratios. The monoterpene (or sesquiterpene) and the therapeutic agent may be covalently linked through carbamate, ester, ether bonds, or any other suitable chemical functional groups. When the monoterpene (or sesquiterpene) and the therapeutic agent are conjugated through a carbamate bond, the therapeutic agent may be any agent bearing at least one carboxylic acid functional group, or any agent bearing at least one amine functional group. In a specific example, a perillyl alcohol conjugate is perillyl alcohol covalently bound via a chemical linking group to a chemotherapeutic agent.

According to the present invention, the therapeutic agents that may be conjugated with monoterpene (or sesquiterpene) include, but are not limited to, chemotherapeutic agents, therapeutic agents for treatment of CNS disorders (including, without limitation, primary degenerative neurological disorders such as Alzheimer's, Parkinson's, multiple sclerosis, Attention-Deficit Hyperactivity Disorder or ADHD, psychological disorders, psychosis and depression), immunotherapeutic agents, angiogenesis inhibitors, and anti-hypertensive agents. Anti-cancer agents that may be conjugated with monoterpene or sesquiterpene can have one or more of the following effects on cancer cells or the subject: cell death; decreased cell proliferation; decreased numbers of cells; inhibition of cell growth; apoptosis; necrosis; mitotic catastrophe; cell cycle arrest; decreased cell size; decreased cell division; decreased cell survival; decreased cell metabolism; markers of cell damage or cytotoxicity; indirect indicators of cell damage or cytotoxicity such as tumor shrinkage; improved survival of a subject; or disappearance of markers associated with undesirable, unwanted, or aberrant cell proliferation. U.S. Patent Publication No. 20080275057.

Also encompassed by the present invention is admixtures and/or coformulations of a monoterpene (or sesquiterpene) and at least one therapeutic agent.

Chemotherapeutic agents include, but are not limited to, DNA alkylating agents, topoisomerase inhibitors, endoplasmic reticulum stress inducing agents, a platinum compound, an antimetabolite, vincalkaloids, taxanes, epothilones, enzyme inhibitors, receptor antagonists, tyrosine kinase inhibitors, boron radiosensitizers (i.e. velcade), and chemotherapeutic combination therapies.

Non-limiting examples of DNA alkylating agents are nitrogen mustards, such as Cyclophosphamide (Ifosfamide, Trofosfamide), Chlorambucil (Melphalan, Prednimustine), Bendamustine, Uramustine and Estramustine; nitrosoureas, such as Carmustine (BCNU), Lomustine (Semustine), Fotemustine, Nimustine, Ranimustine and Streptozocin; alkyl sulfonates, such as Busulfan (Mannosulfan, Treosulfan); Aziridines, such as Carboquone, Triaziquone, Triethylenemelamine; Hydrazines (Procarbazine); Triazenes such as Dacarbazine and Temozolomide (TMZ); Altretamine and Mitobronitol.

Non-limiting examples of Topoisomerase I inhibitors include Campothecin derivatives including SN-38, APC, NPC, campothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier Y. (2006) *Nat. Rev. Cancer* 6(10):789-802 and U.S. Patent Publication No. 200510250854; Protoberberine alkaloids and derivatives thereof including berberrubine and coralyne as described in Li et al. (2000) *Biochemistry* 39(24):7107-7116 and Gatto et al. (1996) *Cancer Res.* 15(12):2795-2800; Phenanthroline derivatives including Benzo[i]phenanthridine, Nitidine, and fagaronine as described in Makhey et al. (2003) *Bioorg. Med. Chem.* 11 (8): 1809-1820; Terbenzimidazole and derivatives thereof as described in Xu (1998) *Biochemistry* 37(10):3558-3566; and Anthracycline derivatives including Doxorubicin, Daunorubicin, and Mitoxantrone as described in Foglesong et al. (1992) *Cancer Chemother. Pharmacol.* 30(2):123-]25, Crow et al. (1994) *J. Med. Chem.* 37(19):31913194, and Crespi et al. (1986) *Biochem. Biophys. Res. Commun.* 136(2):521-8. Topoisomerase II inhibitors include, but are not limited to Etoposide and Teniposide. Dual topoisomerase I and II inhibitors include, but are not limited to, Saintopin and other Naphthecenediones, DACA and other Acridine-4-Carboxamindes, Intoplicine and other Benzopyridoindoles, TAS-I03 and other 7H-indeno[2,1-c]Quinoline-7-ones, Pyrazoloacridine, XR 11576 and other Benzophenazines, XR 5944 and other Dimeric compounds, 7-oxo-7H-dibenz[f,ij]Isoquinolines and 7-oxo-7H-benzo[e]pyrimidines, and Anthracenyl-amino Acid Conjugates as described in Denny and Baguley (2003) *Curr. Top. Med. Chem.* 3(3):339-353. Some agents inhibit Topoisomerase II and have DNA intercalation activity such as, but not limited to, Anthracyclines (Aclarubicin, Daunorubicin, Doxorubicin, Epirubicin, Idarubicin, Amrubicin, Pirarubicin, Valrubicin, Zorubicin) and Antracenediones (Mitoxantrone and Pixantrone).

Examples of endoplasmic reticulum stress inducing agents include, but are not limited to, dimethyl-celecoxib (DMC), nelfinavir, celecoxib, and boron radiosensitizers (i.e. velcade (Bortezomib)).

Platinum based compounds are a subclass of DNA alkylating agents. Non-limiting examples of such agents include Cisplatin, Nedaplatin, Oxaliplatin, Triplatin tetranitrate, Satraplatin, Aroplatin, Lobaplatin, and JM-216. (see McKeage et al. (1997) *J. Clin. Oncol.* 201:1232-1237 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

"FOLFOX" is an abbreviation for a type of combination therapy that is used to treat colorectal cancer. It includes 5-FU, oxaliplatin and leucovorin. Information regarding this treatment is available on the National Cancer Institute's web site, cancer.gov, last accessed on Jan. 16, 2008.

"FOLFOX/BV" is an abbreviation for a type of combination therapy that is used to treat colorectal cancer. This therapy includes 5-FU, oxaliplatin, leucovorin and Bevacizumab. Furthermore, "XELOX/BV" is another combination therapy used to treat colorectal cancer, which includes the prodrug to 5-FU, known as Capecitabine (Xeloda) in combination with oxaliplatin and bevacizumab. Information regarding these treatments are available on the National Cancer Institute's web site, cancer.gov or from 23 the National Comprehensive Cancer Network's web site, nccn.org, last accessed on May 27, 2008.

Non-limiting examples of antimetabolite agents include Folic acid based, i.e. dihydrofolate reductase inhibitors, such as Aminopterin, Methotrexate and Pemetrexed; thymidylate synthase inhibitors, such as Raltitrexed, Pemetrexed; Purine based, i.e. an adenosine deaminase inhibitor, such as Pentostatin, a thiopurine, such as Thioguanine and Mercaptopurine, a halogenated/ribonucleotide reductase inhibitor, such as Cladribine, Clofarabine, Fludarabine, or a guanine/guanosine: thiopurine, such as Thioguanine; or Pyrimidine based, i.e. cytosine/cytidine: hypomethylating agent, such as Azacitidine and Decitabine, a DNA polymerase inhibitor, such as Cytarabine, a ribonucleotide reductase inhibitor, such as Gemcitabine, or a thymine/thymidine: thymidylate synthase inhibitor, such as a Fluorouracil (5-FU). Equivalents to 5-FU include prodrugs, analogs and derivative thereof such as 5'-deoxy-5-fluorouridine (doxifluroidine), 1-tetrahydrofuranyl-5-fluorouracil (ftorafur), Capecitabine (Xeloda), S-I (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Examples of vincalkaloids, include, but are not limited to Vinblastine, Vincristine, Vinflunine, Vindesine and Vinorelbine.

Examples of taxanes include, but are not limited to docetaxel, Larotaxel, Ortataxel, Paclitaxel and Tesetaxel. An example of an epothilone is iabepilone.

Examples of enzyme inhibitors include, but are not limited to farnesyltransferase inhibitors (Tipifarnib); CDK inhibitor (Alvocidib, Seliciclib); proteasome inhibitor (Bortezomib); phosphodiesterase inhibitor (Anagrelide; rolipram); IMP dehydrogenase inhibitor (Tiazofurine); and lipoxygenase inhibitor (Masoprocol). Examples of receptor antagonists include, but are not limited to ERA (Atrasentan); retinoid X receptor (Bexarotene); and a sex steroid (Testolactone).

Examples of tyrosine kinase inhibitors include, but are not limited to inhibitors to ErbB: HER1/EGFR (Erlotinib, Gefitinib, Lapatinib, Vandetanib, Sunitinib, Neratinib); HER2/neu (Lapatinib, Neratinib); RTK class III: C-kit (Axitinib, Sunitinib, Sorafenib), FLT3 (Lestaurtinib), PDGFR (Axitinib, Sunitinib, Sorafenib); and VEGFR (Vandetanib, Semaxanib, Cediranib, Axitinib, Sorafenib); bcr-abl (Imatinib, Nilotinib, Dasatinib); Src (Bosutinib) and Janus kinase 2 (Lestaurtinib).

"Lapatinib" (Tykerb®) is an dual EGFR and erbB-2 inhibitor. Lapatinib has been investigated as an anticancer monotherapy, as well as in combination with trastuzumab, capecitabine, letrozole, paclitaxel and FOLFIRI(irinotecan, 5-fluorouracil and leucovorin), in a number of clinical trials. It is currently in phase III testing for the oral treatment of metastatic breast, head and neck, lung, gastric, renal and bladder cancer.

A chemical equivalent of lapatinib is a small molecule or compound that is a tyrosine kinase inhibitor (TKI) or alternatively a HER-1 inhibitor or a HER-2 inhibitor. Several TKIs have been found to have effective antitumor activity and have been approved or are in clinical trials. Examples of such include, but are not limited to, Zactima (ZD6474), Iressa (gefitinib), imatinib mesylate (STI571; Gleevec), erlotinib (OSI-1774; Tarceva), canertinib (CI 1033), semaxinib (SU5416), vatalanib (PTK787/ZK222584), sorafenib (BAY 43-9006), sutent (SUI 1248) and lefltmomide (SU101).

PTK/ZK is a tyrosine kinase inhibitor with broad specificity that targets all VEGF receptors (VEGFR), the platelet-derived growth factor (PDGF) receptor, c-KIT and c-Fms. Drevs (2003) Idrugs 6(8):787-794. PTK/ZK is a targeted drug that blocks angiogenesis and lymphangiogenesis by inhibiting the activity of all known receptors that bind VEGF including VEGFR-I (Flt-1), VEGFR-2 (KDR/Flk-1) and VEGFR-3 (Flt-4). The chemical names of PTK/ZK are 1-[4-Chloroanilino]-4-[4-pyridylmethyl] phthalazine Succinate or 1-Phthalazinamine, N-(4-chlorophenyl)-4-(4-pyridinylmethyl)-butanedioate (1:1). Synonyms and analogs of PTK/TK are known as Vatalanib, CGP79787D, PTK787/ZK 222584, CGP-79787, DE-00268, PTK-787, PTK787A, VEGFR-TK inhibitor, ZK 222584 and ZK.

Chemotherapeutic agents that can be conjugated with monoterpene or sesquiterpene may also include amsacrine, Trabectedin, retinoids (Alitretinoin, Tretinoin), Arsenic trioxide, asparagine depleter Asparaginase/Pegaspargase), Celecoxib, Demecolcine, Elesclomol, Elsamitrucin, Etoglucid, Lonidamine, Lucanthone, Mitoguazone, Mitotane, Oblimersen, Temsirolimus, and Vorinostat.

The monoterpene or sesquiterpene derivative may be conjugated with angiogenesis inhibitors. Examples of angiogenesis inhibitors include, but are not limited to, angiostatin, angiozyme, antithrombin III, AG3340, VEGF inhibitors, batimastat, bevacizumab (avastin), BMS-275291, CAI, 2C3, HuMV833 Canstatin, Captopril, carboxyamidotriazole, cartilage derived inhibitor (CDI), CC-5013, 6-O-(chloroacetyl-carbonyl)-fumagillol, COL-3, combretastatin, combretastatin A4 Phosphate, Dalteparin, EMD 121974 (Cilengitide), endostatin, erlotinib, gefitinib (Iressa), genistein, halofuginone hydrobromide, Id1, Id3, IM862, imatinib mesylate, IMC-IC11 Inducible protein 10, interferon-alpha, interleukin 12, lavendustin A, LY317615 or AE-941, marimastat, mspin, medroxpregesterone acetate, Meth-1, Meth-2, 2-methoxyestradiol (2-ME), neovastat, oteopontin cleaved product, PEX, pigment epithelium growth factor (PEGF), platelet factor 4, prolactin fragment, proliferin-related protein (PRP), PTK787/ZK 222584, ZD6474, recombinant human platelet factor 4 (rPF4), restin, squalamine, SU5416, SU6668, SU11248 suramin, Taxol, Tecogalan, thalidomide, thrombospondin, TNP-470, troponin-1, vasostatin, VEG1, VEGF-Trap, and ZD6474.

Non-limiting examples of angiogenesis inhibitors also include, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, pentosan polysulfate, angiotensin II antagonists, cyclooxygenase inhibitors (including non-steroidal anti-inflammatory drugs (NSAIDs) such as aspirin and ibuprofen, as well as selective cyclooxygenase-2 inhibitors such as celecoxib and rofecoxib), and steroidal anti-inflammatories (such as corticosteroids, mineralocorticoids, dexamethasone, prednisone, prednisolone, methylpred, betamethasone).

Other therapeutic agents that modulate or inhibit angiogenesis and may also be conjugated with monoterpene or sesquiterpene include agents that modulate or inhibit the coagulation and fibrinolysis systems, including, but not limited to, heparin, low molecular weight heparins and carboxypeptidase U inhibitors (also known as inhibitors of active thrombin activatable fibrinolysis inhibitor [TAFIa]). U.S. Patent Publication No. 20090328239. U.S. Pat. No. 7,638,549.

Non-limiting examples of the anti-hypertensive agents include angiotensin converting enzyme inhibitors (e.g., captopril, enalapril, delapril etc.), angiotensin II antagonists (e.g., candesartan cilexetil, candesartan, losartan (or Cozaar), losartan potassium, eprosartan, valsartan (or Diovan), termisartan, irbesartan, tasosartan, olmesartan, olmesartan medoxomil etc.), calcium antagonists (e.g., manidipine, nifedipine, amlodipine (or Amlodin), efonidipine, nicardipine etc.), diuretics, renin inhibitor (e.g., aliskiren etc.), aldosterone antagonists (e.g., spironolactone, eplerenone etc.), beta-blockers (e.g., metoprolol (or Toporol), atenolol, propranolol, carvedilol, pindolol etc.), vasodilators (e.g., nitrate, soluble guanylate cyclase stimulator or activator, prostacycline etc.), angiotensin vaccine, clonidine and the like. U.S. Patent Publication No. 20100113780.

Other therapeutic agents that may be conjugated with monoterpene (or sesquiterpene) include, but are not limited to, Sertraline (Zoloft), Topiramate (Topamax), Duloxetine (Cymbalta), Sumatriptan (Imitrex), Pregabalin (Lyrica), Lamotrigine (Lamictal), Valaciclovir (Valtrex), Tamsulosin (Flomax), Zidovudine (Combivir), Lamivudine (Combivir), Efavirenz (Sustiva), Abacavir (Epzicom), Lopinavir (Kaletra), Pioglitazone (Actos), Desloratidine (Clarinex), Cetirizine (Zyrtec), Pentoprazole (Protonix), Lansoprazole (Prevacid), Rebeprazole (Aciphex), Moxifloxacin (Avelox), Meloxicam (Mobic), Dorzolamide (Truspot), Diclofenac (Voltaren), Enlapril (Vasotec), Montelukast (Singulair), Sildenafil (Viagra), Carvedilol (Coreg), Ramipril (Delix).

Table 1 lists pharmaceutical agents that can be conjugated with monoterpene (or sesquiterpene), including structure of the pharmaceutical agent and the preferred derivative for conjugation.

TABLE 1

| Brand Name | Generic Name | Activity | Structure | Preferred Derivative |
|---|---|---|---|---|
| Zoloft | Sertraline | Depression | 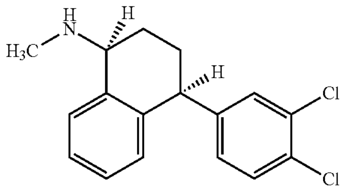 [SMILES: CN[C@H]1CC[C@@H](c2ccc(Cl)c(Cl)c2)c2ccccc21] | Carbamate |
| Topamax | Topiramate | Seizures | 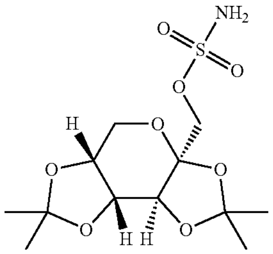 | Carbamate |
| Cymbalta | Duloxetine | Depression | 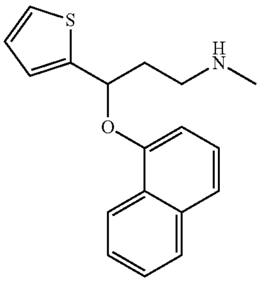 [SMILES: CNCCC(Oc1cccc2ccccc12)c1cccs1] | Carbamate |
| Imitrex | Sumatriptan | Migraine | 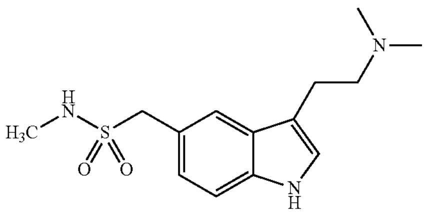 | Carbamate |

TABLE 1-continued

| Brand Name | Generic Name | Activity | Structure | Preferred Derivative |
| --- | --- | --- | --- | --- |
| Lyrica | Pregabalin | Neuropathic pain | 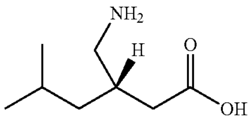 | Carbamate or Ester |
| Lamictal | Lamotrigine | Seizures | 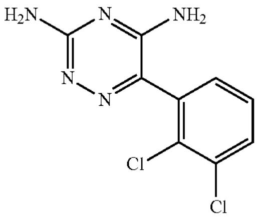 [SMILES: Nc1nnc(-c2cccc(Cl)c2Cl)c(N)n1] | Carbamate |
| Valtrex | Valaciclovir | Herpes | 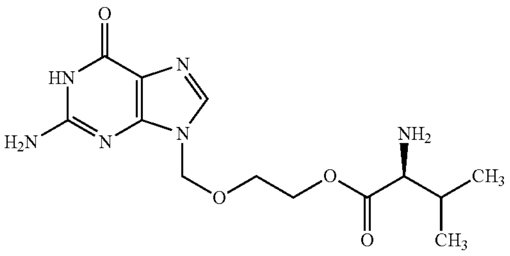 [SMILES: CC(C)[C@H](N)C(=O)OCCOCn1cnc2c(=O)[nH]c(N)nc21] | Carbamate |
| Tarceva | Erlotinib | Non-small cell lung cancer | 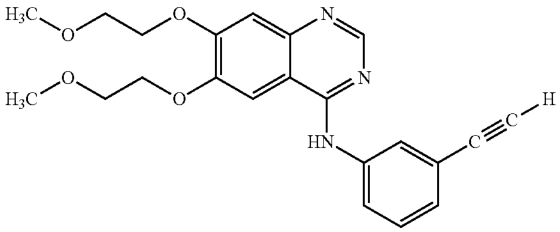 [SMILES: C#Cc1cccc(Nc2ncnc3cc(OCCOC)c(OCCOC)cc23)c1] | Carbamate |
| Flomax | Tamsulosin | Benign prostatic Cancer | 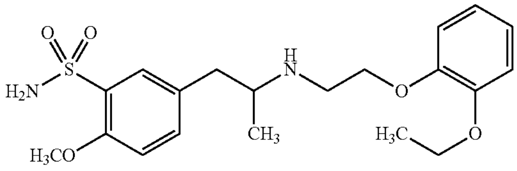 [SMILES: CCOc1ccccc1OCCNC(C)Cc1ccc(OC)c(S(N)(=O)=O)c1] | Carbamate |
| Gleevec | Imatinib | Leukemia | 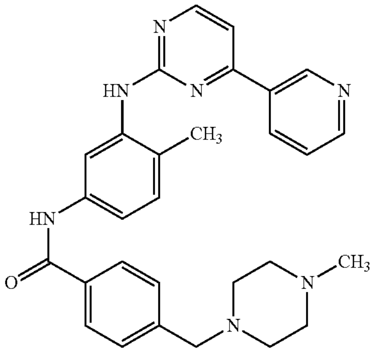 [SMILES: Cc1ccc(NC(=O)c2ccc(CN3CCN(C)CC3)cc2)cc1Nc1nccc(-c2cccnc2)n1] | Carbamate |

TABLE 1-continued
| Brand Name | Generic Name | Activity | Structure | Preferred Derivative |
|---|---|---|---|---|
| Combivir | Zidovudine | HIV infection | 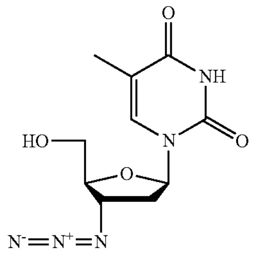 | Carbamate |
| Combivir | Lamivudine | HIV infection | 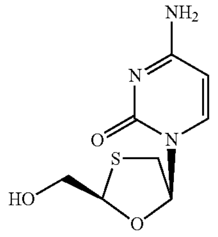 [SMILES: Nc1ccn([C@@H]2CS[C@H](CO)O2)c(=O)n1] | Carbonate |
| Sustiva | Efavirenz | HIV infection | 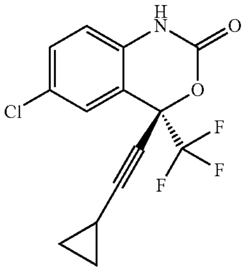 [SMILES: O=C1Nc2ccc(Cl)cc2[C@@](C#CC2CC2)(C(F)(F)F)O1] | Carbamate |
| Epzicom | Abacavir | HIV infection | 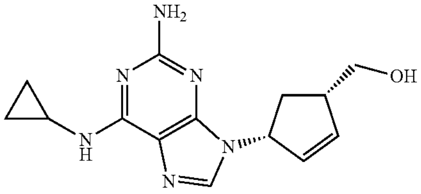 [SMILES: Nc1nc(NC2CC2)c2ncn([C@H]3C=C[C@@H](CO)C3)c2n1] | Carbamate |
| Kaletra | Lopinavir | HIV infection | 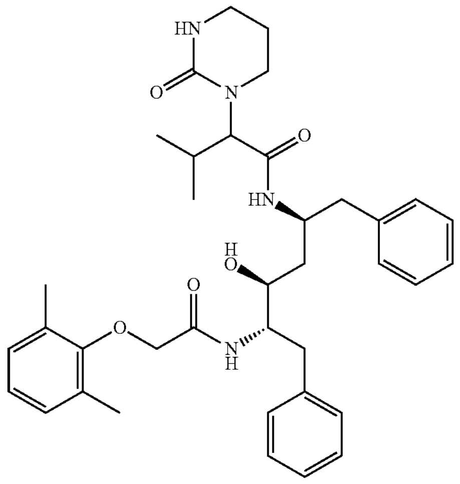 [SMILES: Cc1cccc(C)c1OCC(=O)N[C@@H](Cc1ccccc1)[C@@H](O)C[C@H](Cc1ccccc1)NC(=O)C(C(C)C)N1CCCNC1=O] | Carbamate |

TABLE 1-continued

| Brand Name | Generic Name | Activity | Structure | Preferred Derivative |
|---|---|---|---|---|
| Actos | Pioglitazone | Type-2 diabetes | 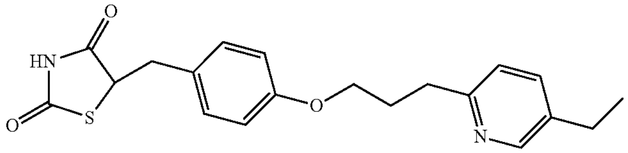 [SMILES: CCc1ccc(CCCOc2ccc(CC3SC(=O)NC3=O)cc2)nc1] | Carbamate |
| Clarinex | Desloratidine | Allergic rhinitis | 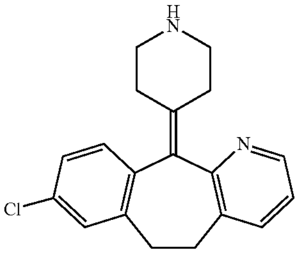 [SMILES: Clc1ccc2c(c1)CCc1cccnc1C2=C1CCNCC1] | Carbamate |
| Zyrtec | Cetirizine | Allergic | 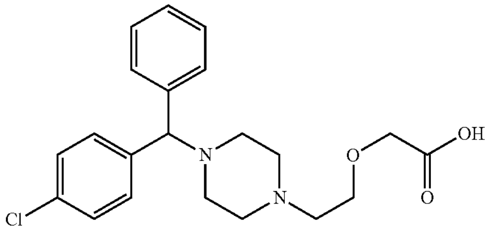 [SMILES: O=C(O)COCCN1CCN(C(c2ccccc2)c2ccc(Cl)cc2)CC1] | Ester |
| Protonix | Pentoprazole | Gastrointestinal | 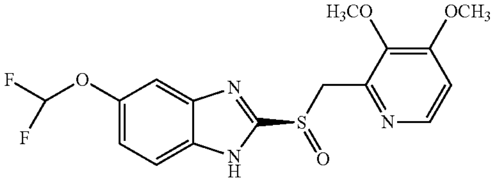 [SMILES: COc1ccnc(C[S@@](=O)c2nc3cc(OC(F)F)ccc3[nH]2)c1OC] | Carbamate |
| Prevacid | Lansoprazole | Gastrointestinal | 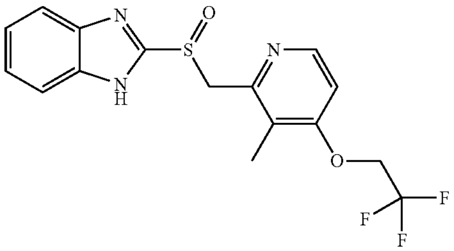 [SMILES: Cc1c(OCC(F)(F)F)ccnc1CS(=O)c1nc2ccccc2[nH]1] | Carbamate |
| Aciphex | Rebeprazole | Gastrointestinal | 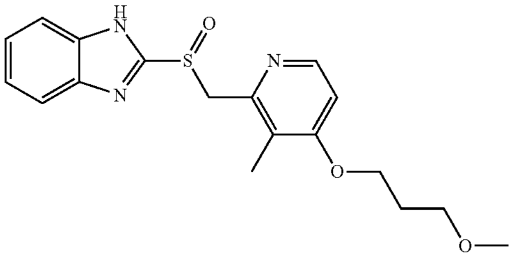 [SMILES: COCCCOc1ccnc(CS(=O)c2nc3ccccc3[nH]2)c1C] | Carbamate |

TABLE 1-continued

| Brand Name | Generic Name | Activity | Structure | Preferred Derivative |
|---|---|---|---|---|
| Diovan | Valsartan | Hypertension | 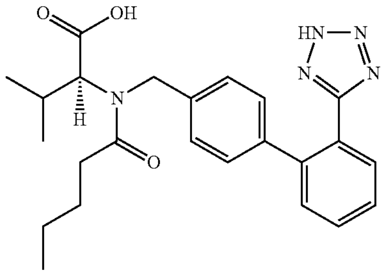 [SMILES: CCCCC(=O)N(Cc1ccc(-c2ccccc2-c2nn[nH]n2)cc1)[C@H](C(=O)O)C(C)C] | Carbamate |
| Cozaar | Losartan | Hypertension | 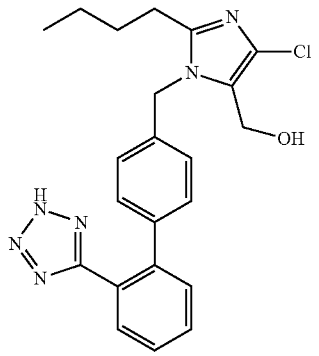 [SMILES: CCCCc1nc(Cl)c(CO)n1Cc1ccc(-c2ccccc2-c2nn[nH]n2)cc1] | Carbamate |
| Avelox | Moxifloxacin | Bacterial infection | 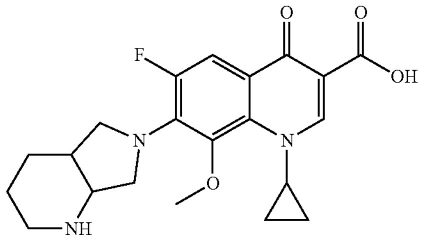 [SMILES: COc1c(N2CC3CCCNC3C2)c(F)cc2c(=O)c(C(=O)O)cn(C3CC3)c12] | Carbamate or Ester |
| Mobic | Meloxicam | Osteoarthritis | 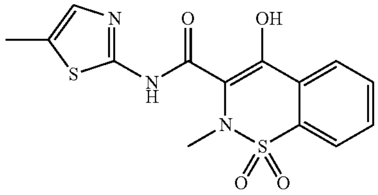 [SMILES: Cc1cnc(NC(=O)C2=C(O)c3ccccc3S(=O)(=O)N2C)s1] | Carbamate |
| Truspot | Dorzolamide | Intraocular pressure | 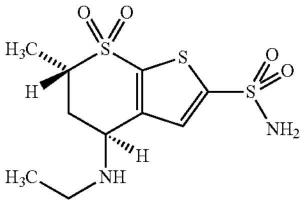 [SMILES: CCN[C@H]1C[C@H](C)S(=O)(=O)c2sc(S(N)(=O)=O)cc21] | Carbamate |
| Voltaren | Diclofenac | Osteoarthritis & rheumatoid arthritis | 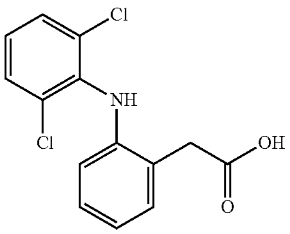 [SMILES: O=C(O)Cc1ccccc1Nc1c(Cl)cccc1Cl] | Carbamate or Ester |

TABLE 1-continued

| Brand Name | Generic Name | Activity | Structure | Preferred Derivative |
|---|---|---|---|---|
| Vasotec | Enlapril | Hypertension | 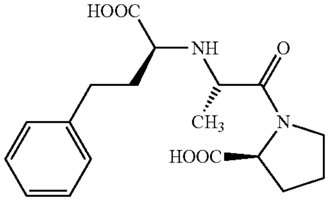 | Carbamate or Ester |
| Singulair | Montelukast | Asthma | 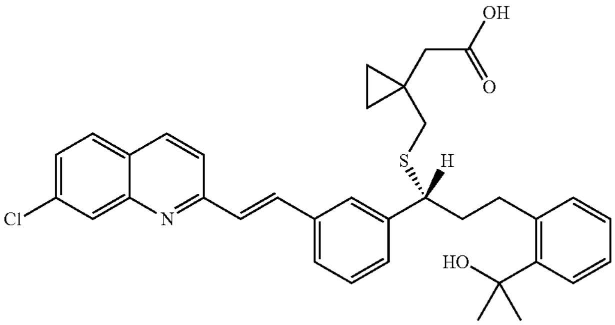 [SMILES: CC(C)(O)c1ccccc1CC[C@@H](SCC1(CC(=O)O)CC1)c1cccc(/C=C/c2ccc3ccc(Cl)cc3n2)c1] | Ester |
| Amlodin | Amlodipine | Hypertension | 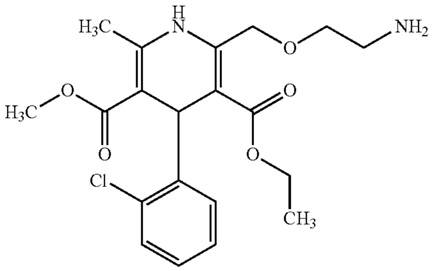 [SMILES: CCOC(=O)C1=C(COCCN)NC(C)=C(C(=O)OC)C1c1ccccc1Cl] | Carbamate |
| Toporol | Metoprolol | Hypertension | 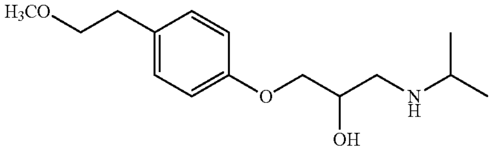 [SMILES: COCCc1ccc(OCC(O)CNC(C)C)cc1] | Carbamate |
| Viagra | Sildenafil | Erectile dysfunction | 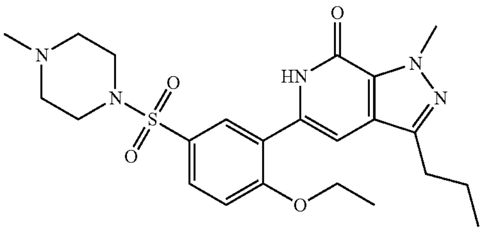 [SMILES: CCCc1nn(C)c2c(=O)[nH]c(-c3cc(S(=O)(=O)N4CCN(C)CC4)ccc3OCC)cc12] | Carbamate |
| Coreg | Carvedilol | Hypertension | 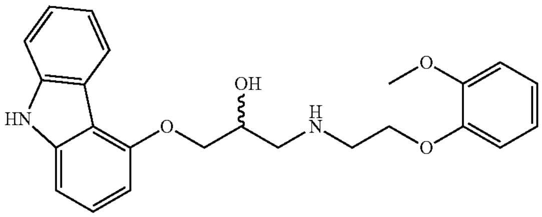 [SMILES: COc1ccccc1OCCNCC(O)COc1cccc2[nH]c3ccccc3c12] | Carbamate |

TABLE 1-continued

| Brand Name | Generic Name | Activity | Structure | Preferred Derivative |
|---|---|---|---|---|
| Delix | Ramipril | Hypertension | 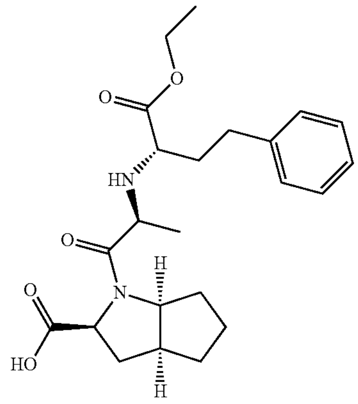 [SMILES: CCOC(=O)[C@H](CCc1ccccc1)N[C@@H](C)C(=O)N1[C@H](C(=O)O)C[C@@H]2CCC[C@@H]21] | Carbamate or Ester |
| Sinemet (Parcopa, Atamet) | L-DOPA | Neurological disorders | 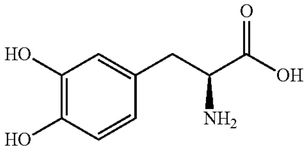 [SMILES: N[C@@H](Cc1ccc(O)c(O)c1)C(=O)O] | Carbamate or Ester |

The purity of the monoterpene (or sesquiterpene) derivatives may be assayed by gas chromatography (GC) or high pressure liquid chromatography (HPLC). Other techniques for assaying the purity of monoterpene (or sesquiterpene) derivatives and for determining the presence of impurities include, but are not limited to, nuclear magnetic resonance (NMR) spectroscopy, mass spectrometry (MS), GC-MS, infrared spectroscopy (IR), and thin layer chromatography (TLC). Chiral purity can be assessed by chiral GC or measurement of optical rotation.

The monoterpene (or sesquiterpene) derivatives may be purified by methods such as crystallization, or by separating the monoterpene (or sesquiterpene) derivative from impurities according to the unique physicochemical properties (e.g., solubility or polarity) of the derivative. Accordingly, the monoterpene (or sesquiterpene) derivative can be separated from the monoterpene (or sesquiterpene) by suitable separation techniques known in the art, such as preparative chromatography, (fractional) distillation, or (fractional) crystallization.

The invention also provides for methods of using monoterpenes (or sesquiterpenes) derivatives to treat a disease, such as a cancer or other nervous system disorders. A monoterpene (or sesquiterpene) derivative may be administered alone, or in combination with radiation, surgery or chemotherapeutic agents. A monoterpene or sesquiterpene derivative may also be co-administered with antiviral agents, anti-inflammatory agents or antibiotics. The agents may be administered concurrently or sequentially. A monoterpene (or sesquiterpene) derivative can be administered before, during or after the administration of the other active agent(s).

The monoterpene or sesquiterpene derivative may be used in combination with radiation therapy. In one embodiment, the present invention provides for a method of treating tumor cells, such as malignant glioma cells or brain metastases, with radiation, where the cells are treated with an effective amount of a monoterpene derivative, such as a perillyl alcohol carbamate, and then exposed to radiation. Monoterpene derivative treatment may be before, during and/or after radiation. For example, the monoterpene or sesquiterpene derivative may be administered continuously beginning one week prior to the initiation of radiotherapy and continued for two weeks after the completion of radiotherapy. U.S. Pat. Nos. 5,587,402 and 5,602,184.

In one embodiment, the present invention provides for a method of treating tumor cells, such as malignant glioma cells or brain metastases, with chemotherapy, where the cells are treated with an effective amount of a monoterpene derivative, such as a perillyl alcohol carbamate, and then exposed to chemotherapy. Monoterpene derivative treatment may be before, during and/or after chemotherapy.

Monoterpene (or sesquiterpene) derivatives may be used for the treatment of nervous system cancers, such as a malignant glioma (e.g., astrocytoma, anaplastic astrocytoma, glioblastoma multiforme), retinoblastoma, pilocytic astrocytomas (grade I), meningiomas, metastatic brain tumors, neuroblastoma, pituitary adenomas, skull base meningiomas, and skull base cancer. As used herein, the term "nervous system tumors" refers to a condition in which a subject has a malignant proliferation of nervous system cells.

Cancers that can be treated by the present monoterpene (or sesquiterpene) derivatives include, but are not limited to, lung cancer, ear, nose and throat cancer, leukemia, colon cancer, melanoma, pancreatic cancer, mammary cancer, prostate cancer, breast cancer, hematopoietic cancer, ovarian cancer, basal cell carcinoma, biliary tract cancer; bladder cancer; bone cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia including acute myeloid leukemia, acute lymphoid leukemia, chronic myeloid leukemia, chronic lymphoid leukemia; liver cancer; lymphoma including Hodgkin's and Non-Hodgkin's lymphoma; myeloma; fibroma, neuroblastoma; oral cavity cancer (e.g., lip, tongue, mouth, and pharynx); ovarian cancer; pancreatic cancer; prostate cancer; retinoblastoma; rhabdomyosarcoma; rectal cancer; renal cancer; cancer of the respiratory system; sarcoma; skin cancer; stomach cancer; testicular cancer; thyroid cancer; uterine cancer; cancer of the urinary system, as well as other carcinomas and sarcomas. U.S. Pat. No. 7,601,355.

The present monoterpene (or sesquiterpene) derivatives can be used for treating brain metastases that originate or spread from a primary cancer such as a systemic cancer, lung cancer, prostate cancer, breast cancer, hematopoietic cancer, ovarian cancer, bladder cancer, germ cell tumors, kidney cancer, leukemia, lymphoma, and melanoma. In some embodiments, the present invention provides for a method for treating a mammal having a metastatic cancer, such as metastatic breast cancer that has spread to the brain, by administering to the mammal a monoterpene (or sesquiterpene) derivative described herein, e.g., a POH carbamate, such as TMZ-POH.

The present invention also provides methods of treating CNS disorders, including, without limitation, primary degenerative neurological disorders such as Alzheimer's, Parkinson's, psychological disorders, psychosis and depression. Treatment may consist of the use of a monoterpene or sesquiterpene derivative alone or in combination with current medications used in the treatment of Parkinson's, Alzheimer's, or psychological disorders.

The present invention also provides a method of improving immunomodulatory therapy responses comprising the steps of exposing cells to an effective amount of a monoterpene or sisquiterpene derivative, such as a perillyl alcohol carbamate, before or during immunomodulatory treatment. Preferred immunomodulatory agents are cytokines, such interleukins, lymphokines, monokines, interfereons and chemokines.

The present composition may be administered by any method known in the art, including, without limitation, intranasal, oral, transdermal, ocular, intraperitoneal, inhalation, intravenous, ICV, intracisternal injection or infusion, subcutaneous, implant, vaginal, sublingual, urethral (e.g., urethral suppository), subcutaneous, intramuscular, intravenous, rectal, sub-lingual, mucosal, ophthalmic, spinal, intrathecal, intra-articular, intra-arterial, sub-arachinoid, bronchial and lymphatic administration. Topical formulation may be in the form of gel, ointment, cream, aerosol, etc; intranasal formulation can be delivered as a spray or in a drop; transdermal formulation may be administered via a transdermal patch or iontorphoresis; inhalation formulation can be delivered using a nebulizer or similar device. Compositions can also take the form of tablets, pills, capsules, semisolids, powders, sustained release formulations, solutions, suspensions, elixirs, aerosols, or any other appropriate compositions.

To prepare such pharmaceutical compositions, one or more of monoterpene (or sesquiterpene) derivatives may be mixed with a pharmaceutical acceptable carrier, adjuvant and/or excipient, according to conventional pharmaceutical compounding techniques. Pharmaceutically acceptable carriers that can be used in the present compositions encompass any of the standard pharmaceutical carriers, such as a phosphate buffered saline solution, water, and emulsions, such as an oil/water or water/oil emulsion, and various types of wetting agents. The compositions can additionally contain solid pharmaceutical excipients such as starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, particularly for injectable solutions, include water, saline, aqueous dextrose, and glycols. For examples of carriers, stabilizers and adjuvants, see *Remington's Pharmaceutical Sciences*, edited by E. W. Martin (Mack Publishing Company, 18th ed., 1990). The compositions also can include stabilizers and preservatives.

As used herein, the term "therapeutically effective amount" is an amount sufficient to treat a specified disorder or disease or alternatively to obtain a pharmacological response treating a disorder or disease. Methods of determining the most effective means and dosage of administration can vary with the composition used for therapy, the purpose of the therapy, the target cell being treated, and the subject being treated. Treatment dosages generally may be titrated to optimize safety and efficacy. Single or multiple administrations can be carried out with the dose level and pattern being selected by the treating physician. Suitable dosage formulations and methods of administering the agents can be readily determined by those of skill in the art. For example, the composition are administered at about 0.01 mg/kg to about 200 mg/kg, about 0.1 mg/kg to about 100 mg/kg, or about 0.5 mg/kg to about 50 mg/kg. When the compounds described herein are co-administered with another agent or therapy, the effective amount may be less than when the agent is used alone.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer. If the composition is in the form of a gel, the composition may be rubbed onto a membrane of the patient, for example, the skin, preferably intact, clean, and dry skin, of the shoulder or upper arm and or the upper torso, and maintained thereon for a period of time sufficient for delivery of the monoterpene (or sesquiterpene) derivative to the blood serum of the patient. The composition of the present invention in gel form may be contained in a tube, a sachet, or a metered pump. Such a tube or sachet may contain one unit dose, or more than one unit dose, of the composition. A metered pump may be capable of dispensing one metered dose of the composition.

This invention also provides the compositions as described above for intranasal administration. As such, the compositions can further comprise a permeation enhancer. Southall et al. *Developments in Nasal Drug Delivery,* 2000. The monoterpene (or sesquiterpene) derivative may be administered intranasally in a liquid form such as a solution, an emulsion, a suspension, drops, or in a solid form such as a powder, gel, or ointment. Devices to deliver intranasal medications are well known in the art. Nasal drug delivery can be carried out using devices including, but not limited to, intranasal inhalers, intranasal spray devices, atomizers, nasal spray bottles, unit dose containers, pumps, droppers, squeeze bottles, nebulizers, metered dose inhalers (MDI), pressurized dose inhalers, insufflators, and bi-directional devices. The nasal delivery device can be metered to administer an accurate effective dosage amount to the nasal cavity. The nasal delivery device can be for single unit delivery or multiple unit delivery. In a specific example, the ViaNase Electronic Atomizer from Kurve Technology (Bethell, Wash.) can be used in this invention (http://www.kurvetech- .com). The compounds of the present invention may also be delivered through a tube, a catheter, a syringe, a packtail, a pledget, a nasal tampon or by submucosal infusion. U.S. Patent Publication Nos. 20090326275, 20090291894, 20090281522 and 20090317377.

The monoterpene (or sesquiterpene) derivative can be formulated as aerosols using standard procedures. The monoterpene (or sesquiterpene) derivative may be formulated with or without solvents, and formulated with or without carriers. The formulation may be a solution, or may be an aqueous emulsion with one or more surfactants. For example, an aerosol spray may be generated from pressurized container with a suitable propellant such as, dichlorodifluoromethane, trichlorofluoromethane, dichlorotetrafluoroethane, hydrocarbons, compressed air, nitrogen, carbon dioxide, or other suitable gas. The dosage unit can be determined by providing a valve to deliver a metered amount. Pump spray dispensers can dispense a metered dose or a dose having a specific particle or droplet size. As used herein, the term "aerosol" refers to a suspension of fine solid particles or liquid solution droplets in a gas. Specifically, aerosol includes a gas-borne suspension of droplets of a monoterpene (or sesquiterpene), as may be produced in any suitable device, such as an MDI, a nebulizer, or a mist sprayer. Aerosol also includes a dry powder composition of the composition of the instant invention suspended in air or other carrier gas. Gonda (1990) *Critical Reviews in Therapeutic Drug Carrier Systems* 6:273-313. Raeburn et al., (1992) *Pharmacol. Toxicol. Methods* 27:143-159.

The monoterpene (or sesquiterpene) derivative may be delivered to the nasal cavity as a powder in a form such as microspheres delivered by a nasal insufflator. The monoterpene (or sesquiterpene) derivative may be absorbed to a solid surface, for example, a carrier. The powder or microspheres may be administered in a dry, air-dispensable form. The powder or microspheres may be stored in a container of the insufflator. Alternatively the powder or microspheres may be filled into a capsule, such as a gelatin capsule, or other single dose unit adapted for nasal administration.

The pharmaceutical composition can be delivered to the nasal cavity by direct placement of the composition in the nasal cavity, for example, in the form of a gel, an ointment, a nasal emulsion, a lotion, a cream, a nasal tampon, a dropper, or a bioadhesive strip. In certain embodiments, it can be desirable to prolong the residence time of the pharmaceutical composition in the nasal cavity, for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, chitosans and/or cellulose (e.g., methyl or propyl; hydroxyl or carboxy; carboxymethyl or hydroxylpropyl).

The composition containing the purified monoterpene (or sesquiterpene) can be administered by oral inhalation into the respiratory tract, i.e., the lungs.

Typical delivery systems for inhalable agents include nebulizer inhalers, dry powder inhalers (DPI), and metered-dose inhalers (MDI).

Nebulizer devices produce a stream of high velocity air that causes a therapeutic agent in the form of liquid to spray as a mist. The therapeutic agent is formulated in a liquid form such as a solution or a suspension of particles of suitable size. In one embodiment, the particles are micronized. The term "micronized" is defined as having about 90% or more of the particles with a diameter of less than about 10 μm. Suitable nebulizer devices are provided commercially, for example, by PARI GmbH (Starnberg, Germany). Other nebulizer devices include Respimat (Boehringer Ingelheim) and those disclosed in, for example, U.S. Pat. Nos. 7,568,480 and 6,123,068, and WO 97/12687. The monoterpenes (or sesquiterpenes) can be formulated for use in a nebulizer device as an aqueous solution or as a liquid suspension.

DPI devices typically administer a therapeutic agent in the form of a free flowing powder that can be dispersed in a patient's air-stream during inspiration. DPI devices which use an external energy source may also be used in the present invention. In order to achieve a free flowing powder, the therapeutic agent can be formulated with a suitable excipient (e.g., lactose). A dry powder formulation can be made, for example, by combining dry lactose having a particle size between about 1 μm and 100 μm with micronized particles of the monoterpenes (or sesquiterpenes) and dry blending. Alternatively, the monoterpene can be formulated without excipients. The formulation is loaded into a dry powder dispenser, or into inhalation cartridges or capsules for use with a dry powder delivery device. Examples of DPI devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI devices typically discharge a measured amount of therapeutic agent using compressed propellant gas. Formulations for MDI administration include a solution or suspension of active ingredient in a liquefied propellant. Examples of propellants include hydrofluoroalklanes (HFA), such as 1,1,1,2-tetrafluoroethane (HFA 134a) and 1,1,1,2,3,3,3-heptafluoro-n-propane, (HFA 227), and chlorofluorocarbons, such as $CCl_3F$. Additional components of HFA formulations for MDI administration include co-solvents, such as ethanol, pentane, water; and surfactants, such as sorbitan trioleate, oleic acid, lecithin, and glycerin. (See, for example, U.S. Pat. No. 5,225,183, EP 0717987, and WO 92/22286). The formulation is loaded into an aerosol canister, which forms a portion of an MDI device. Examples of MDI devices developed specifically for use with HFA propellants are provided in U.S. Pat. Nos. 6,006,745 and 6,143,227. For examples of processes of preparing suitable formulations and devices suitable for inhalation dosing see U.S. Pat. Nos. 6,268,533, 5,983,956, 5,874,063, and 6,221,398, and WO 99/53901, WO 00/61108, WO 99/55319 and WO 00/30614.

The monoterpene (or sesquiterpene) derivative may be encapsulated in liposomes or microcapsules for delivery via inhalation. A liposome is a vesicle composed of a lipid bilayer membrane and an aqueous interior. The lipid membrane may be made of phospholipids, examples of which include phosphatidylcholine such as lecithin and lysolecithin; acidic phospholipids such as phosphatidylserine and phosphatidylglycerol; and sphingophospholipids such as phosphatidylethanolamine and sphingomyelin. Alternatively, cholesterol may be added. A microcapsule is a particle coated with a coating material. For example, the coating material may consist of a mixture of a film-forming polymer, a hydrophobic plasticizer, a surface activating agent or/and a lubricant nitrogen-containing polymer. U.S. Pat. Nos. 6,313,176 and 7,563,768.

The monoterpene (or sesquiterpene) derivative may also be used alone or in combination with other chemotherapeutic agents via topical application for the treatment of localized cancers such as breast cancer or melanomas. The monoterpene (or sesquiterpene) derivative may also be used in combination with narcotics or analgesics for transdermal delivery of pain medication.

This invention also provides the compositions as described above for ocular administration. As such, the compositions can further comprise a permeation enhancer. For ocular administration, the compositions described herein can be formulated as a solution, emulsion, suspension, etc. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851.

The monoterpene (or sesquiterpene) derivative can be given alone or in combination with other drugs for the treatment of the above diseases for a short or prolonged period of time. The present compositions can be administered to a mammal, preferably a human. Mammals include, but are not limited to, murines, rats, rabbit, simians, bovines, ovine, porcine, canines, feline, farm animals, sport animals, pets, equine, and primates.

The invention also provides a method for inhibiting the growth of a cell in vitro, ex vivo or in vivo, where a cell, such as a cancer cell, is contacted with an effective amount of the monoterpene (or sesquiterpene) derivative as described herein.

Pathological cells or tissue such as hyperproliferative cells or tissue may be treated by contacting the cells or tissue with an effective amount of a composition of this invention. The cells, such as cancer cells, can be primary cancer cells or can be cultured cells available from tissue banks such as the American Type Culture Collection (ATCC). The pathological cells can be cells of a systemic cancer, gliomas, meningiomas, pituitary adenomas, or a CNS metastasis or brain metastasis from a systemic cancer, lung cancer, prostate cancer, breast cancer, hematopoietic cancer, ovarian cancer, bladder cancer, germ cell tumors, kidney cancer, leukemia, lymphoma, and melanoma. The cells can be from a vertebrate, preferably a mammal, more preferably a human. U.S. Patent Publication No. 2004/0087651. Balassiano et al. (2002) *Intern. J. Mol. Med.* 10:785-788. Thorne, et al. (2004) *Neuroscience* 127:481-496. Fernandes, et al. (2005) *Oncology Reports* 13:943-947. Da Fonseca, et al. (2008) *Surgical Neurology* 70:259267. Da Fonseca, et al. (2008) *Arch. Immunol. Ther. Exp.* 56:267-276. Hashizume, et al. (2008) *Neuroncology* 10:112-120.

In vitro efficacy of the present composition can be determined using methods well known in the art. For example, the cytoxicity of the present monoterpene (or sesquiterpene) and/or the therapeutic agents may be studied by MTT [3-(4,5-dimethylthiazol-2-yl)-2,5-diphenyl tetrazolium bromide] cytotoxicity assay. MTT assay is based on the principle of uptake of MTT, a tetrazolium salt, by metabolically active cells where it is metabolized into a blue colored formazon product, which can be read spectrometrically. *J. of Immunological Methods* 65: 55 63, 1983. The cytoxicity of the present monoterpene (or sesquiterpene) derivative and/or the therapeutic agents may be studied by colony formation assay. Functional assays for inhibition of VEGF secretion and IL-8 secretion may be performed via ELISA. Cell cycle block by the present monoterpene (or sesquiterpene) derivative and/or the therapeutic agents may be studied by standard propidium iodide (PI) staining and flow cytometry.

Invasion inhibition may be studied by Boyden chambers. In this assay a layer of reconstituted basement membrane, Matrigel, is coated onto chemotaxis filters and acts as a barrier to the migration of cells in the Boyden chambers. Only cells with invasive capacity can cross the Matrigel barrier. Other assays include, but are not limited to cell viability assays, apoptosis assays, and morphological assays.

The following are examples of the present invention and are not to be construed as limiting.

EXAMPLES

Example 1: Synthesis of Dimethyl Celecoxib bisPOH Carbamate (4-(bis-N,N'-4-isopropenyl cyclohex-1-enylmethyloxy carbonyl [5-(2,5-dimethyl phenyl)-3-trifluoromethyl pyrazol-1-yl] benzenesulfonamide) (also referred to as POH-DMC or DMC-POH herein)

The reaction scheme is the following:

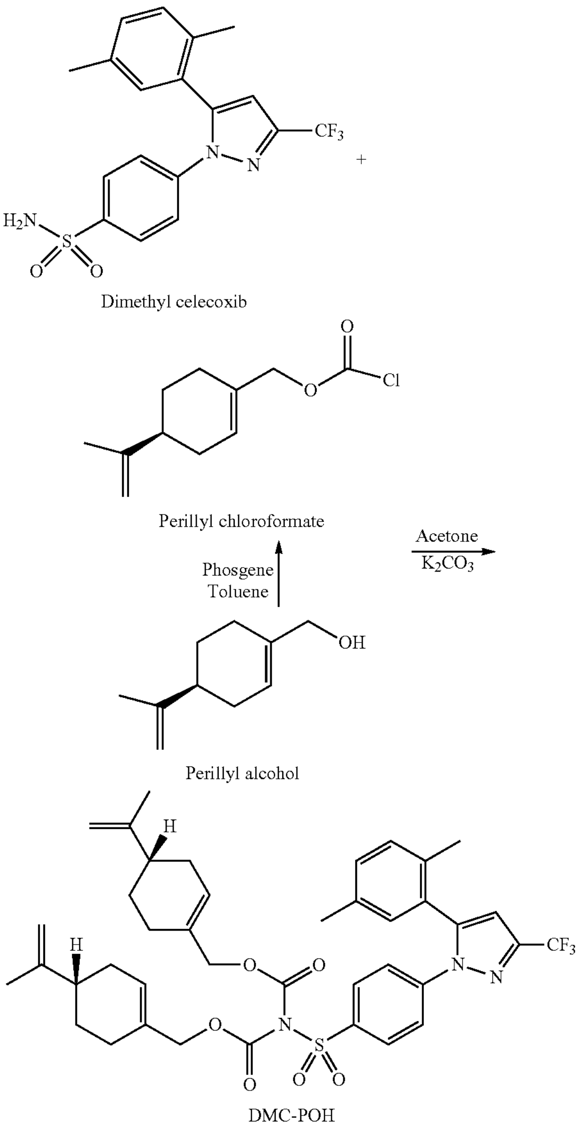

Dimethyl celecoxib

Perillyl chloroformate

Perillyl alcohol

DMC-POH

Phosgene (20% in toluene, 13 ml, 26.2 mmol) was added to a mixture of perillyl alcohol (2.0 grams, 13.1 mmol) and potassium carbonate (5.4 grams, 39.1 mmol) in dry toluene (30 mL) over a period of 30 minutes while maintaining the temperature between 10° C. to 15° C. The reaction mixture was allowed to warm to room temperature and stirred for 8.0 hours under $N_2$. The reaction mixture was quenched with water (30 mL) and the organic layer was separated. The aqueous layer was extracted with toluene (20 mL) and the combined organic layer was washed with water (50 mL×2), brine (15%, 30 mL) and dried over sodium sulfate (20 grams). The filtered organic layer was concentrated under vacuum to give perillyl chloroformate as an oil. Weight: 2.5 grams; Yield: 89%. $^1$H-NMR (400 MHz, $CDCl_3$): δ 1.5 (m, 1H), 1.7 (s, 3H), 1.8 (m, 1H), 2.0 (m, 1H), 2.2 (m, 4H), 4.7 (dd, 4H); 5.87 (m, 1H).

Perillyl chloroformate (0.11 grams, 0.55 mmol) was added slowly to a mixture of dimethyl celecoxib (0.2 grams, 0.50 mmol) and potassium carbonate (0.13 grams, 1.0 mmol) in dry acetone (10 mL) over a period of 5 minutes under $N_2$. The reaction mixture was heated to reflux and maintained for 3 hours. Since TLC analysis indicated the presence of dimethyl celecoxib (>60%), another 1.0 equivalent of perillyl chloroformate was added and refluxed for an additional 5 hours. The reaction mixture was cooled and acetone was concentrated under vacuum to give a residue.

The resulting residue was suspended in water (15 mL) and extracted with ethyl acetate (3×15 mL). The combined organic layer was washed with water (20 mL) followed by brine (15%, 20 mL) and dried over sodium sulfate. The filtered organic layer was concentrated under vacuum to give a residue which was purified by column chromatography [column dimensions: diameter: 1.5 cm, height: 10 cm, silica: 230-400 mesh] and eluted with hexanes (100 mL) followed by a mixture of hexanes/ethyl acetate (95:5, 100 mL). The hexane/ethyl acetate fractions were combined and concentrated under vacuum to give a gummy mass.

The product POH carbamate exhibited a weight of 120 mg and a yield of 31%. $^1$H-NMR (400 MHz, $CDCl_3$): δ 0.9 (m, 2H), 1.4 (m, 2H), 1.7 (m, 7H*), 1.95 (m, 8H*), 2.1 (m, 4H), 2.3 (s, 3H), 4.4 (d, 2H), 4.7 (dd, 2H), 5.6 (br d, 2H), 6.6 (s, 1H), 7.0 (br s, 1H), 7.12 (d, 1H), 7.19 (d, 1H), 7.4 (d, 2H), 7.85 (d, 2H); MS, m/e: 751.8 ($M^+$ 3%), 574.3 (100%), 530.5 (45%), 396 (6%). * N.B. further 2H overlapping from presumed impurity discounted in NMR integration.

Example 2: In Vitro Cytotoxicity Studies of POH-DMC Carbamate (POH-DMC)

First cytotoxicity assays were carried out after cells were treated with dimethyl-celecoxib (DMC) alone. FIG. 1 shows the results of the MTT cytotoxicity assays performed on human malignant glioma cells U87, A172 and U251 with DMC alone.

Figure 2:
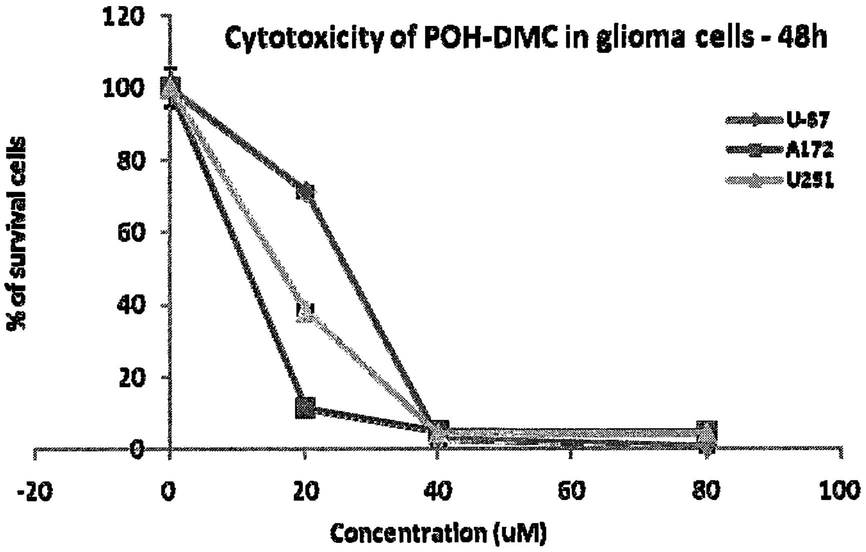
FIG. 2 shows the results of the MTT cytotoxicity assays demonstrating the efficacy of the POH–DMC conjugate in killing U87, A172 and U251 human glioma cells according to the present invention.

Then U87, A172 and U251 cells were treated with dimethyl celecoxib bisPOH carbamate (POH-DMC) (e.g., synthesized by the method in Example 1), and the MTT cytotoxicity assays performed (FIG. 2). The results suggest that POH carbamate POH-DMC exhibited much better cytotoxicity than DMC alone.

Example 3: Synthesis of Temozolomide POH Carbamate (3-methyl 4-oxo-3,4-dihydroimidazo[5,1-d][1,2,3,5]tetrazine-8-carbonyl)-carbamic acid-4-isopropenyl cyclohex-1-enylmethyl ester) (also referred to as TMZ-POH or POH-TMZ herein)

The reaction scheme is the following:

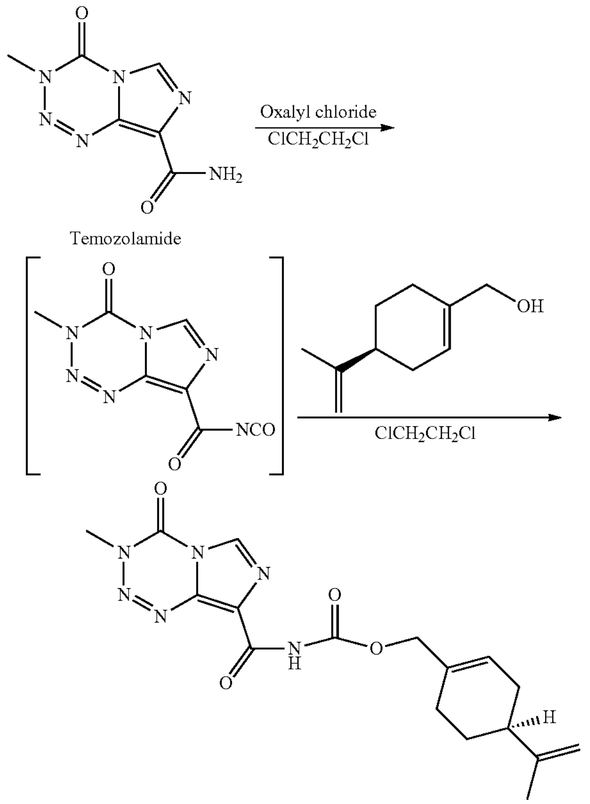

TMZ-POH

Oxalyl chloride (0.13 grams, 1.0 mmol) was added slowly to a mixture of temozolomide (OChem Incorporation, 0.1 grams, 0.5 mmol) in 1,2-dichloroethane (10 mL) over a period of 2 minutes while maintaining the temperature at 10° C. under $N_2$. The reaction mixture was allowed to warm to room temperature and then heated to reflux for 3 hours. The excess of oxalyl chloride and 1,2-dichloroethane were removed by concentration under vacuum. The resulting residue was re-dissolved in 1,2-dichlorethane (15 mL) and the reaction mixture was cooled to 10° C. under $N_2$. A solution of perillyl alcohol (0.086 grams, 0.56 mmol) in 1,2-dichloroethane (3 mL) was added over a period of 5 minutes. The reaction mixture was allowed to warm to room temperature and stirred for 14 hours. 1,2-dichloroethane was concentrated under vacuum to give a residue, which was triturated with hexanes. The resulting yellow solid was filtered and washed with hexanes. Weight: 170 mg; Yield: 89%. $^1$H-NMR (400 MHz, $CDCl_3$): δ 1.4-2.2 (m, 10H), 4.06 (s, 3H), 4.6-4.8 (m, 4H), 5.88 (br s, 1H), 8.42 (s, 1H), 9.31 (br s, 1H); MS, no molecular ion peak was observed. m/e: 314 (100%), 286.5 (17%), 136 (12%).

Alternatively, temozolomide POH carbamate was synthesized according to the following procedure. Oxalyl chloride (0.13 grams, 1.0 mmol) was added slowly to a mixture of temozolomide (OChem Incorporation, 0.1 grams, 0.5 mmol)

in 1,2-dichloroethane (10 mL) over a period of 2 minutes while maintaining the temperature at 10° C. under $N_2$. The reaction mixture was allowed to warm to room temperature and then heated to reflux for 3 hours. The excess of oxalyl chloride and 1,2-dichloroethane were removed by concentration under vacuum. The resulting residue was re-dissolved in 1,2-dichlorethane (15 mL) and the reaction mixture was cooled to 10° C. under $N_2$. A solution of perillyl alcohol (0.086 grams, 0.56 mmol) in 1,2-dichloroethane (3 mL) was added over a period of 5 minutes. The reaction mixture was allowed to warm to room temperature and stirred for 14 hours. 1,2-Dichloroethane was concentrated under vacuum to give a residue, which was purified by a short silica-plug column (column dimensions: diameter: 2 cm, height: 3 cm, silica: 230-400 mesh) and eluted with a mixture of hexanes/ethyl acetate (1:1, 100 mL). The hexane/ethyl acetate fractions were combined and concentrated under vacuum to give a white solid residue which was triturated with heptanes and filtered to obtain a white solid. Weight: 170 mg; Yield: 89%. $^1$H-NMR (400 MHz, CDC13): 1.4-2.2 (m, 10H), 4.06 (s, 3H), 4.6-4.8 (m, 4H), 5.88 (br s, 1H), 8.42 (s, 1H), 9.31 (br s, 1H); MS, no molecular ion peak was observed, m/e: 314 (100%), 286.5 (17%), 136 (12%).

Example 4: In Vitro Cytotoxicity Studies of TMZ-POH

Figure 3:
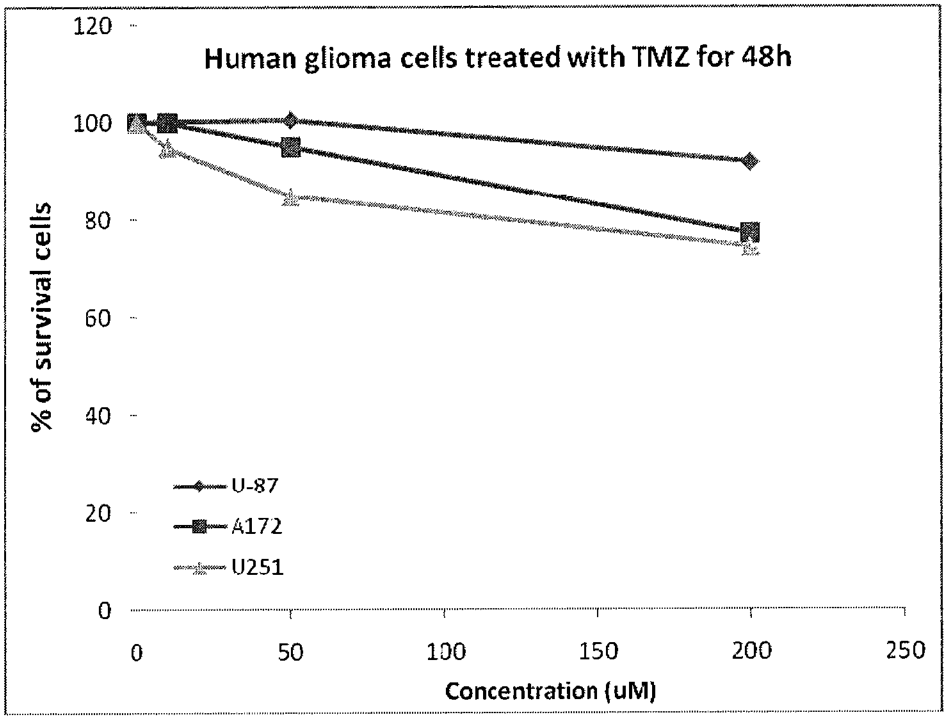
FIG. 3 shows the results of the MTT cytotoxicity assays demonstrating the efficacy of temozolomide (TMZ) in killing U87, A172 and U251 human glioma cells.

First cytotoxicity assays were carried out after cells were treated with temozolomide (TMZ) alone, the standard alkylating agent used in the treatment of malignant gliomas. FIG. 3 shows the results of the MTT cytotoxicity assays performed on human malignant glioma cells U87, A172 and U251 with TMZ alone. Increasing concentrations of TMZ had minimal cytotoxicity towards the cell lines tested.

Figure 4:
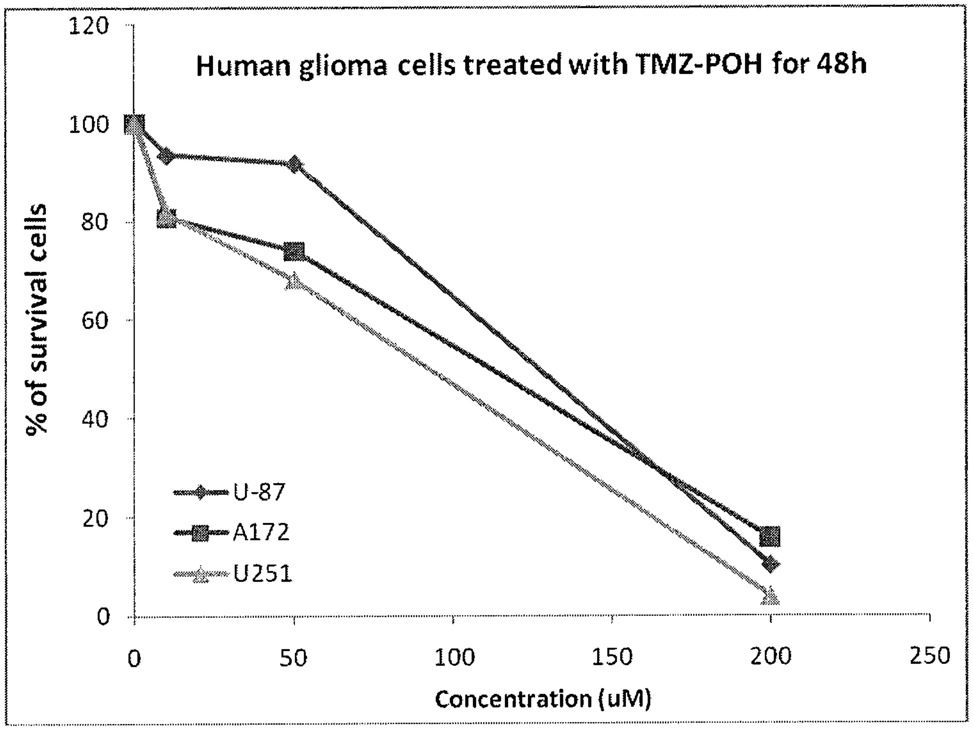
FIG. 4 shows the results of the MTT cytotoxicity assays demonstrating the efficacy of the TMZ-POH conjugate in killing U87, A172, and U251 human glioma cells according to the present invention.

Then TMZ-resistant glioma cell lines U87, A172 and U251 cells were treated with TMZ-POH (e.g., synthesized by the method in Example 3). The MTT assay results (FIG. 4) showed that TMZ-POH exhibited substantially higher kill rates of the various human glioma cells compared to TMZ alone.

Example 5: Synthesis of Rolipram POH Carbamate (4-(3-cyclopentyloxy-4-methoxy phenyl)-2-oxo-pyrrolidine-1-carboxylic acid 4-isopropenyl cyclohex-1-enylmethyl ester) (also referred to as Rolipram-POH or POH-Rolipram herein)

The reaction scheme is the following:

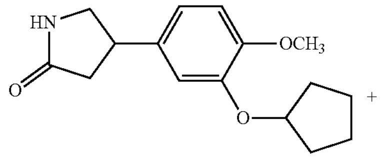

Rolipram

-continued

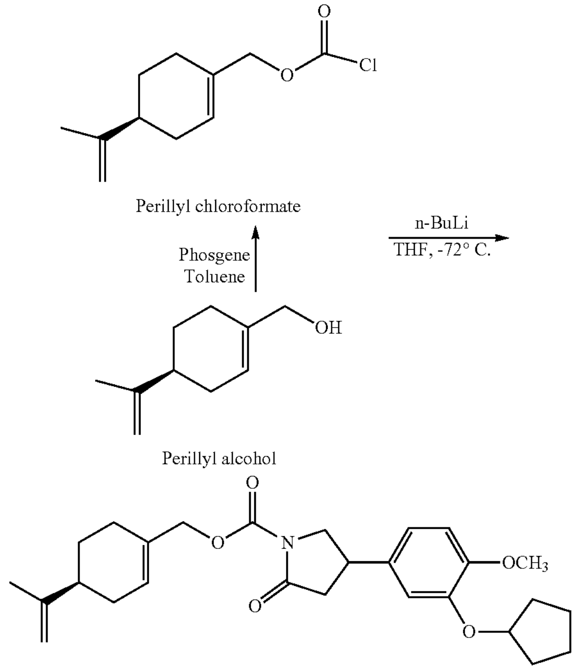

Perillyl chloroformate

Perillyl alcohol

Rolipram-POH

Phosgene (20% in toluene, 13 ml, 26.2 mmol) was added to a mixture of perillyl alcohol (2.0 grams, 13.1 mmol) and potassium carbonate (5.4 grams, 39.1 mmol) in dry toluene (30 mL) over a period of 30 minutes while maintaining the temperature between 10° C. to 15° C. The reaction mixture was allowed to warm to room temperature and stirred for 8.0 hours under $N_2$. The reaction mixture was quenched with water (30 mL) and the organic layer separated. The aqueous layer was extracted with toluene (20 mL) and the combined organic layer washed with water (50 mL×2), brine (15%, 30 mL) and dried over sodium sulfate (20 grams). The filtered organic layer was concentrated under vacuum to give perillyl chloroformate as an oil. Weight: 2.5 grams; Yield: 89%. $^1$H-NMR (400 MHz, $CDCl_3$): δ 1.5 (m, 1H), 1.7 (s, 3H), 1.8 (m, 1H), 2.0 (m, 1H), 2.2 (m, 4H), 4.7 (dd, 4H); 5.87 (m, 1H).

Butyl lithium (2.5 M, 0.18 mL, 0.45 mmol) was added to a solution of rolipram (GL synthesis, Inc., 0.1 grams, 0.36 mmol) in dry THF at −72° C. over a period of 5 minutes under $N_2$. After the reaction mixture was stirred for 1.0 hours at −72° C., perillyl chloroformate (dissolved in 4 mL THF) was added over a period of 15 minutes while maintaining the temperature at −72° C. The reaction mixture was stirred for 2.5 hours and quenched with saturated ammonium chloride (5 mL). The reaction mixture was allowed to warm to room temperature and extracted with ethyl acetate (2×15 mL). The combined organic layer was washed with water (15 mL), brine (15%, 15 mL), and then dried over sodium sulfate. The filtered organic layer was concentrated to give an oil which was purified by column chromatography [column dimensions: diameter: 1.5 cm, height: 10 cm, silica: 230-400 mesh] and eluted with a mixture of 8% ethyl acetate/hexanes (100 mL) followed by 12% ethyl acetate/hexanes (100 mL). The 12% ethyl acetate/hexanes fractions were combined and concentrated under vacuum to yield a gummy solid. Weight: 142 mg; Yield: 86%. $^1$H-NMR (400 MHz, $CDCl_3$): δ 1.5 (m, 1H), 1.6 (m, 2H), 1.7 (s, 3H), 1.9 (m, 6H), 2.2 (m, 5H), 2.7 (m, 1H), 2.9 (m, 1H), 3.5 (m, 1H), 3.7 (m, 1H), 3.8 (s, 3H), 4.2 (m, 1H), 4.7 (m, 6H), 5.8 (br s, 1H), 6.8 (m, 3H); MS, m/e: 452.1 ($M^{+1}$ 53%), 274.1 (100%), 206.0 (55%).

Example 6: In Vitro Cytotoxicity Studies of Rolipram POH Carbamate

Figure 5:
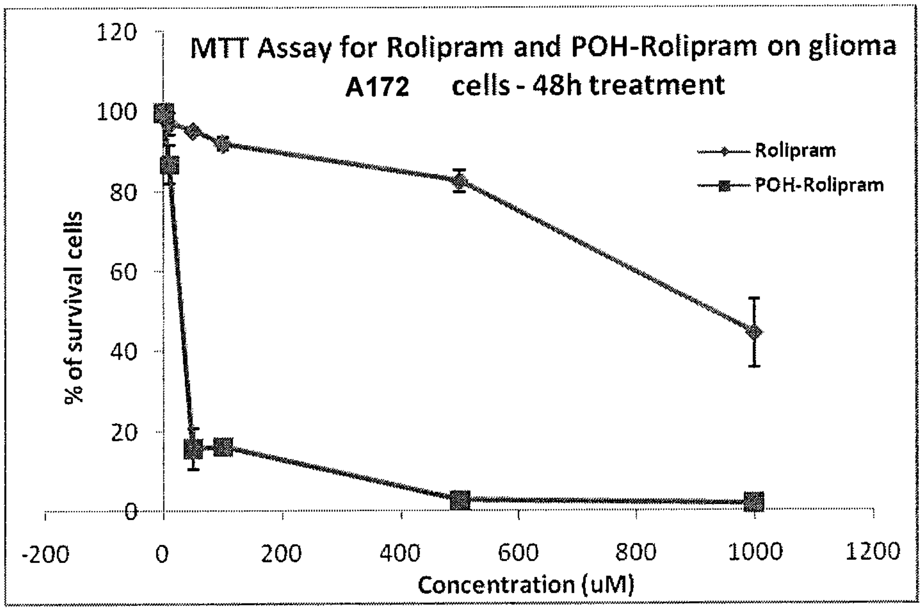
FIG. 5 shows the results of the MTT cytotoxicity assays demonstrating the efficacy of the POH-Rolipram conjugate and Rolipram in killing A172 human glioma cells.
Figure 6:
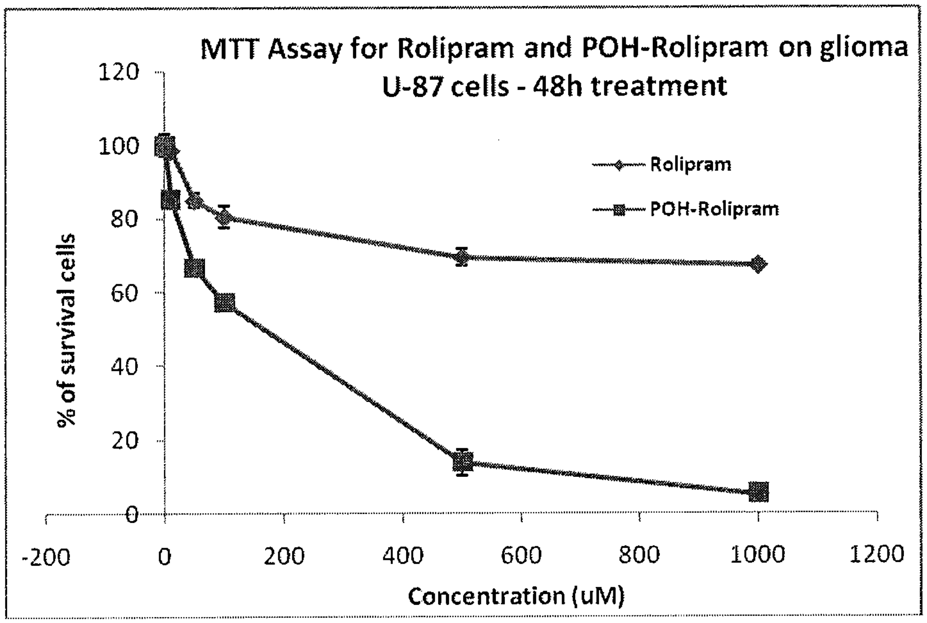
FIG. 6 shows the results of the MTT cytotoxicity assays demonstrating the efficacy of the POH-Rolipram conjugate and Rolipram in killing U87 human glioma cells.
Figure 7:
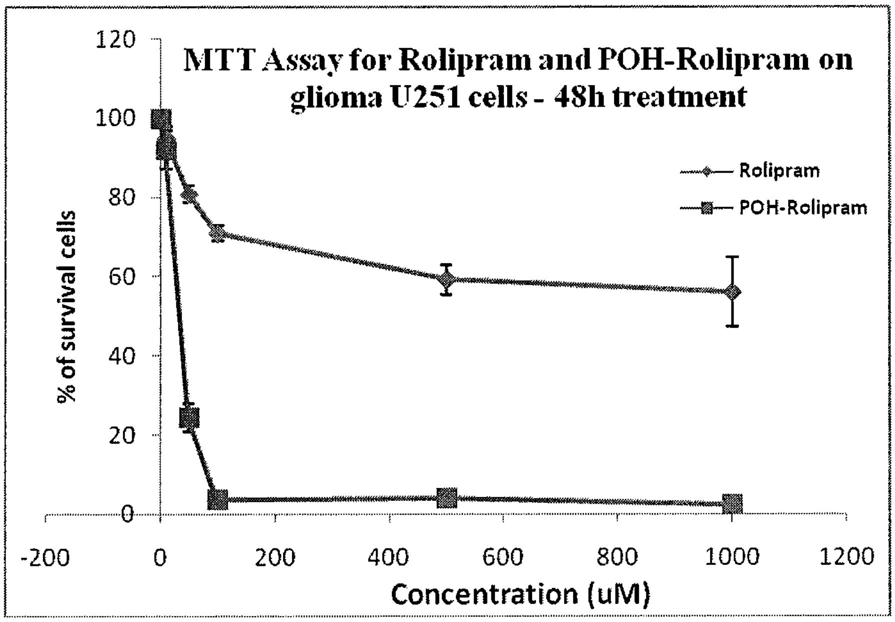
FIG. 7 shows the results of the MTT cytotoxicity assays demonstrating the efficacy of the POH-Rolipram conjugate and Rolipram in killing U251 human glioma cells.
Figure 8:
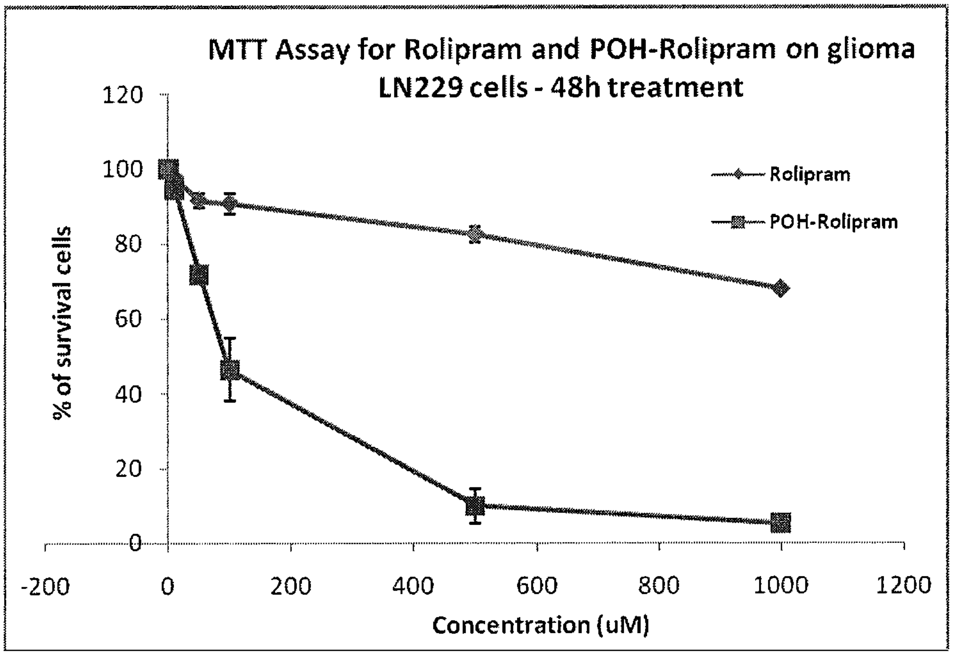
FIG. 8 shows the results of the MTT cytotoxicity assays demonstrating the efficacy of the POH-Rolipram conjugate and Rolipram in killing L229 human glioma cells.

To compare the cytotoxicity of Rolipram POH Carbamate (POH-Rolipram) (e.g., synthesized by the method in Example 5) with rolipram, a type IV phosphodiesterase inducing differentiation and apoptosis in glioma cells, A172, U87, U251 and LN229 human glioma cells were treated with either POH-Rolipram or rolipram for 48 hours. The MTT assay results are shown in FIGS. 5 to 8. POH-Rolipram exhibited substantially higher kill rates compared to rolipram alone for each of the several different human glioma cell types. FIG. 5 shows the MTT assay for increasing concentrations of rolipram and POH-rolipram for A-172 cells. Rolipram alone demonstrates an IC50 of approximately 1000 uM (1 mM). In the presence of POH-rolipram, IC50 is achieved at concentrations as low as 50 uM. FIG. 6 shows the MTT assay for increasing concentrations of rolipram with U-87 cells. IC50 is not met at 1000 uM. On the other hand, IC50 is achieved at 180 uM with POH-rolipram. FIG. 7 shows that IC50 for rolipram alone for U251 cells is achieved at 170 uM; plateau cytotoxicity is reached at 60%. POH-rolipram achieves IC50 at 50 uM, with almost 100% cytoxicity at 100 uM. FIG. 8 shows that IC50 for rolipram alone for LN229 cells is not achieved even at 100 uM. On the other hand, IC50 for POH-rolipram is achieved at 100 uM, with almost 100% cytotoxicity at 10 uM.

Example 7: In Vivo Tumor Growth Inhibition by POH Fatty Acid Derivatives

Figure 9A:
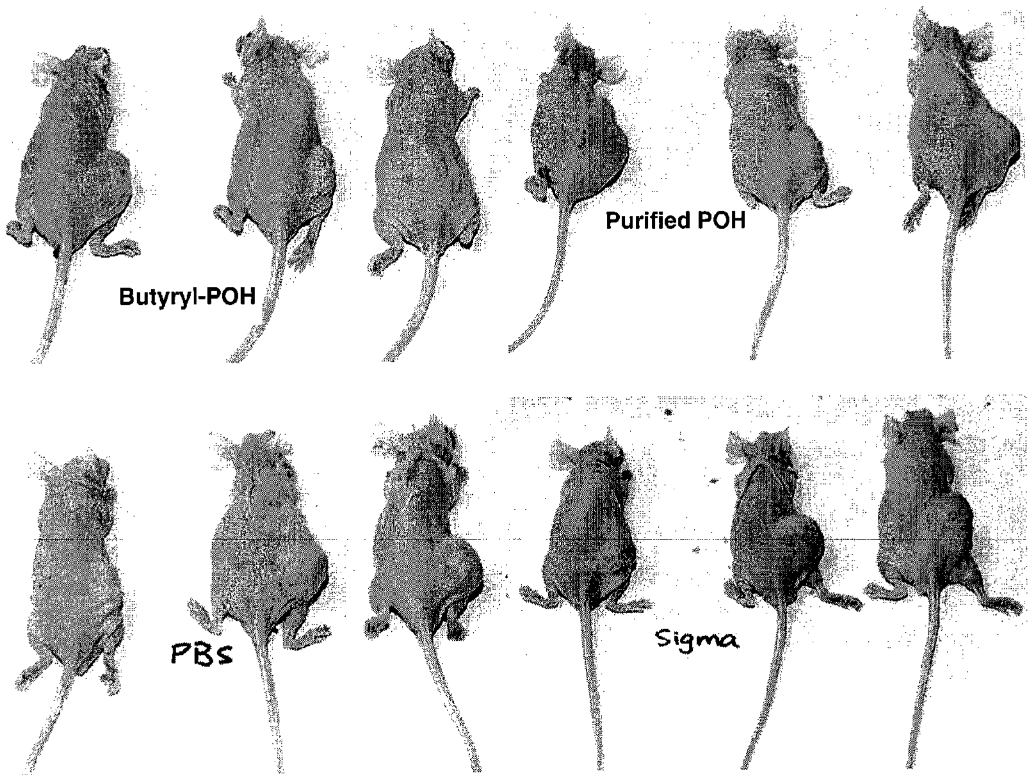
FIGS. 9A and 9B show the inhibition of tumor growth by butyryl-POH in mouse models.
Figure 9B:
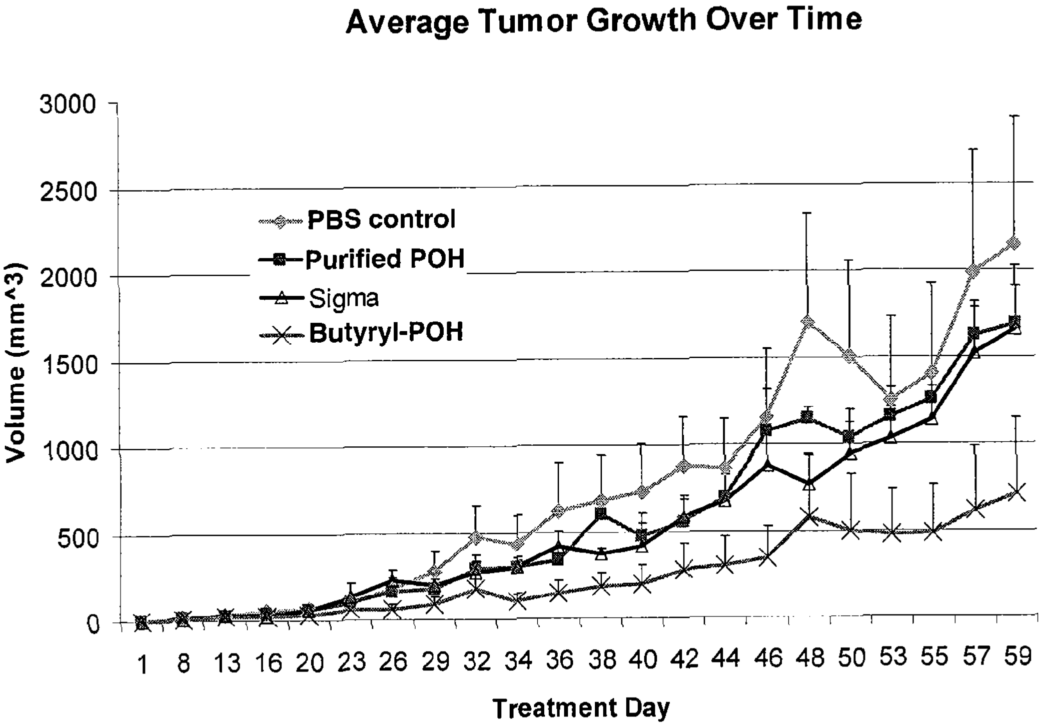

Inhibition of tumor growth by butyryl-POH was studied in a nude mouse subcutaneous glioma model. Mice were injected with U-87 glioma cells (500,000 cells/injection) and allowed to form a palpable nodule over two weeks. Once palpable nodule was formed, the mice were treated with local application of various compounds as indicated in FIGS. 9A and 9B via a Q-tip (1 cc/application/day) over a period of 8 weeks. FIG. 9A shows the images of subcutaneous U-87 gliomas in nude mice treated with butyryl-POH, purified (S)-perillyl alcohol having a purity greater than 98.5% ("purified POH"), POH purchased from Sigma chemicals, or phosphate buffered saline (PBS; negative control). FIG. 9B shows average tumor growth over time (total time period of 60 days). Butyryl-POH demonstrated the greatest inhibition of tumor growth, followed by purified POH and Sigma POH.

Figure 10:
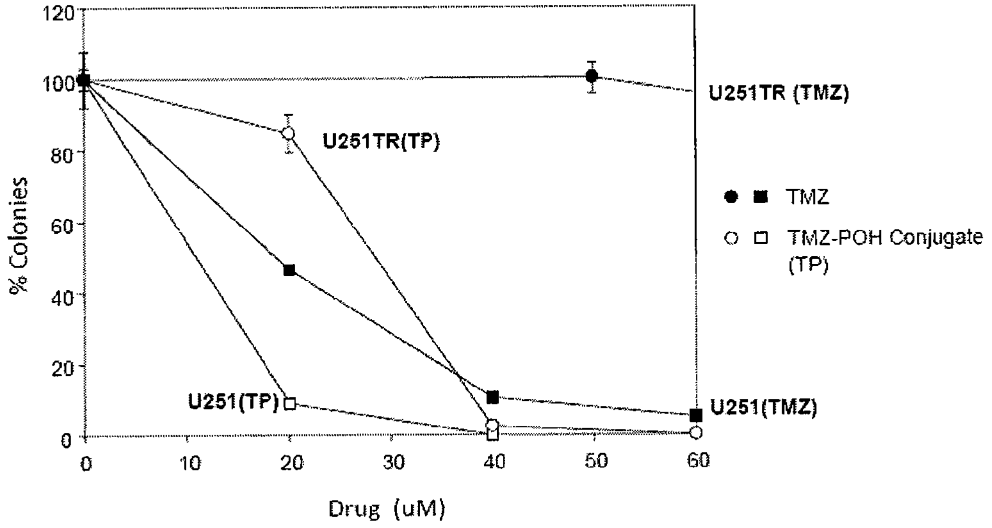
FIG. 10 shows the results of a Colony forming Assay (CFA) demonstrating the cytotoxic effect of TMZ and TMZ-POH on TMZ sensitive (U251) and TMZ resistant (U251TR) U251 cells.

Example 8: In Vitro Cytotoxicity Studies of TMZ and TMZ-POH on TMZ Sensitive and Resistant Glioma Cells Colony forming assays were carried out after cells were treated with TMZ alone, POH alone, and the TMZ-POH conjugate. The colony forming assays were carried out as described in Chen T C, et al. Green tea epigallocatechin gallate enhances therapeutic efficacy of temozolomide in orthotopic mouse glioblastoma models. *Cancer Lett.* 2011 Mar. 28; 302(2):100-8. FIG. 10 shows the results of the colony forming assays performed on TMZ sensitive (U251) and TMZ resistant (U251TR) U251 cells with TMZ or TMZ-POH. TMZ demonstrated cytotoxicity towards TMZ sensitive U251 cells, but had minimal cytotoxicity towards TMZ resistant U251 cells. TMZ-POH demonstrated cytotoxicity towards both TMZ sensitive and TMZ resistant U251 cells.

Figure 11:
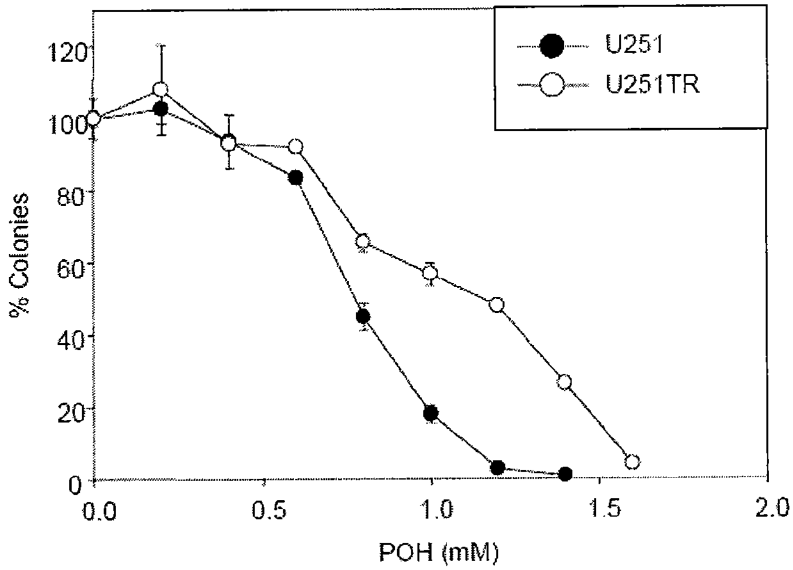
FIG. 11 shows the results of a Colony forming Assay (CFA) demonstrating the cytotoxic effect of POH on TMZ sensitive (U251) and TMZ resistant (U251 TR) U251 cells.

FIG. 11 shows the results of the colony forming assays performed on TMZ sensitive (U251) and TMZ resistant (U251TR) U251 cells with POH. POH demonstrated cytotoxicity towards both TMZ sensitive and TMZ resistant U251 cells. TMZ-POH (FIG. 10) exhibited substantially greater potency compared to POH alone (FIG. 11) in the colony forming assays.

Figure 12:
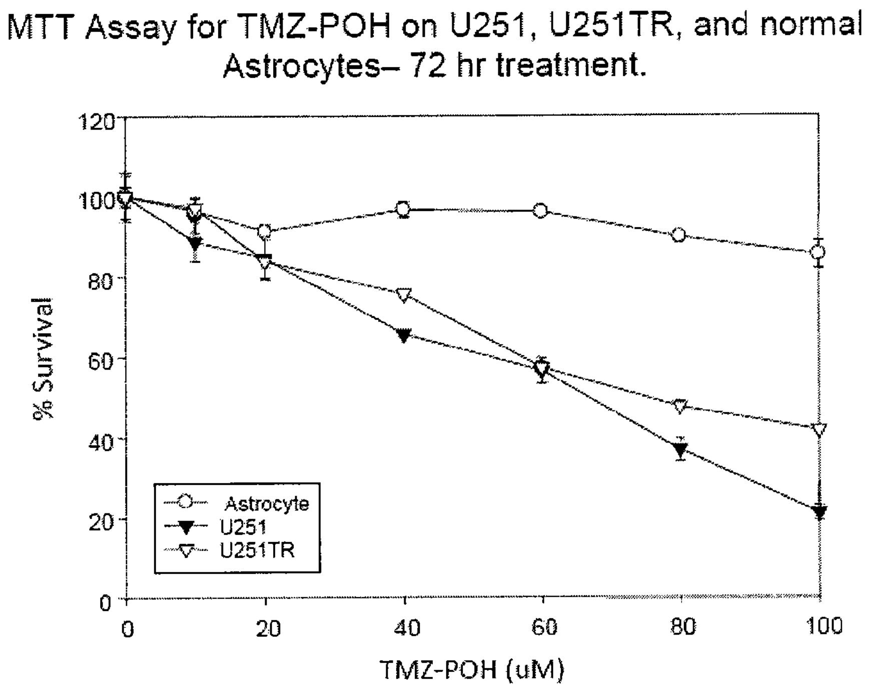
FIG. 12 shows the results of the MTT cytotoxicity assays demonstrating the efficacy of the TMZ-POH conjugate in killing U251 cells, U251TR cells, and normal astrocytes.

Example 9: In Vitro Cytotoxicity Studies of TMZ-POH on U251 Cells, U251TR Cells, and Normal Astrocytes MTT cytotoxicity assays were carried out after cells were treated with the TMZ-POH conjugate. The MTT cytotoxicity assays were carried out as described in Chen T C, et al. Green tea epigallocatechin gallate enhances therapeutic efficacy of temozolomide in orthotopic mouse glioblastoma models. *Cancer Lett.* 2011 Mar. 28; 302(2):100-8. FIG. 12 shows the results of the MTT cytotoxicity assays performed on TMZ sensitive cells (U251), TMZ resistant cells (U251TR) and normal astrocytes. TMZ-POH demonstrated cytotoxicity towards both TMZ sensitive and TMZ resistant U251 cells, but not towards normal astrocytes.

Figure 13:
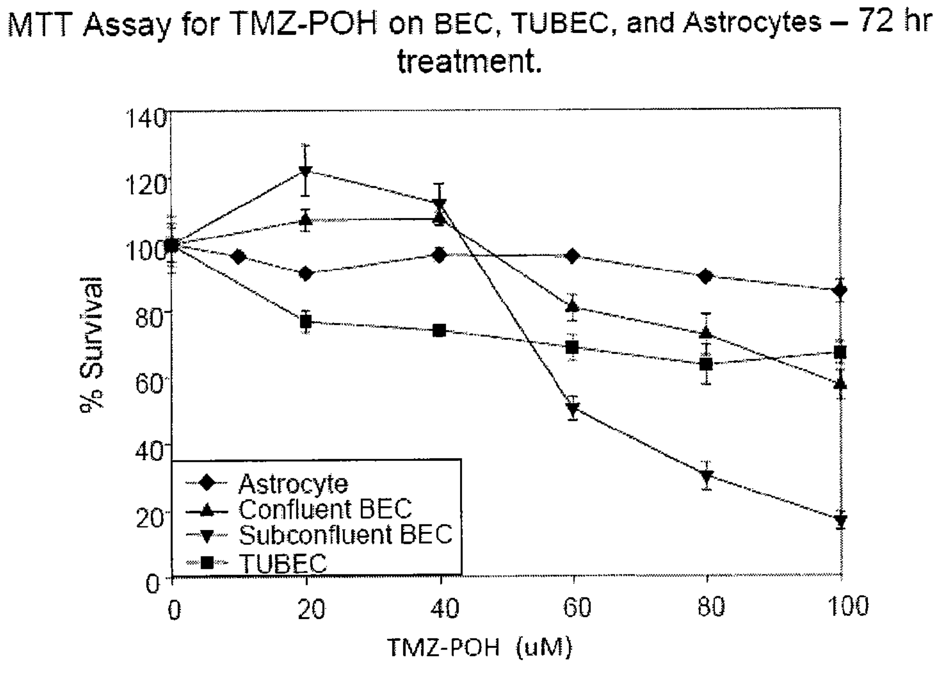
FIG. 13 shows the results of the MTT cytotoxicity assays demonstrating the efficacy of the TMZ-POH conjugate in killing normal astrocytes, brain endothelial cells (BEC; confluent and subconfluent), and tumor brain endothelial cells (TuBEC).

Example 10: In Vitro Cytotoxicity Studies of TMZ-POH on BEC, TuBEC, and Normal Astrocytes MTT cytotoxicity assays were carried out after cells were treated with the TMZ-POH conjugate. The MTT cytotoxicity assays were carried out as described in Chen T C, et al. Green tea epigallocatechin gallate enhances therapeutic efficacy of temozolomide in orthotopic mouse glioblastoma models. *Cancer Lett.* 2011 Mar. 28; 302(2):100-8. FIG. 13 shows the results of the MTT cytotoxicity assays performed on normal astrocytes, brain endothelial cells (BEC; confluent and subconfluent), and tumor brain endothelial cells (TuBEC). TMZ-POH did not induce significant cytotoxicity on normal astrocytes, confluent BEC, or TuBEC. Mild to moderate cytotoxicity was demonstrated in subconfluent BEC at high concentrations of TMZ-POH.

Figure 14:
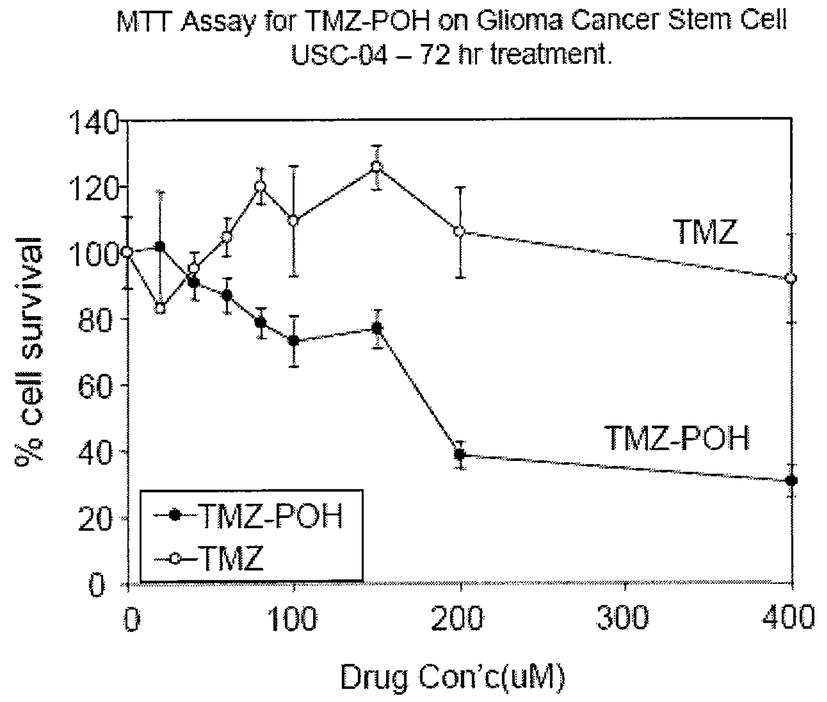
FIG. 14 shows the results of the MTT cytotoxicity assays demonstrating the efficacy of TMZ and the TMZ-POH conjugate in killing USC-04 glioma cancer stem cells.
Figure 15:
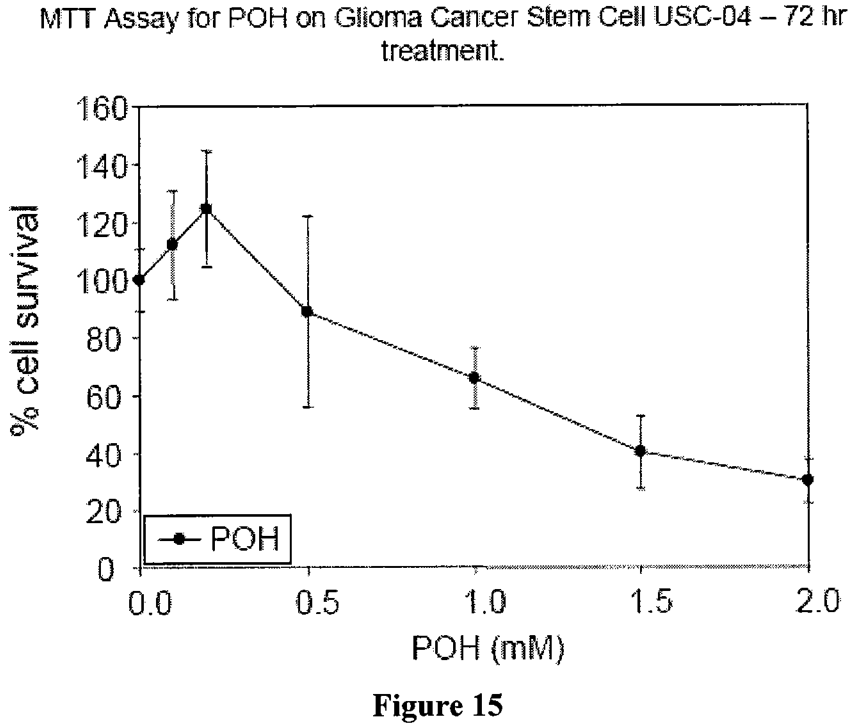
FIG. 15 shows the results of the MTT cytotoxicity assays demonstrating the efficacy of POH in killing USC-04 glioma cancer stem cells.

Example 11: In Vitro Cytotoxicity Studies of TMZ and TMZ-POH on USC-04 Glioma Cancer Stem Cells MTT cytotoxicity assays were carried out after cells were treated with the TMZ alone, POH alone, or the TMZ-POH conjugate. The MTT cytotoxicity assays were carried out as described in Chen T C, et al. Green tea epigallocatechin gallate enhances therapeutic efficacy of temozolomide in orthotopic mouse glioblastoma models. *Cancer Lett.* 2011 Mar. 28; 302(2):100-8. FIG. 14 shows the results of the MTT cytotoxicity assays performed on USC-04 glioma cancer stem cells. TMZ did not induce significant cytotoxicity with increasing concentrations (0-400 uM). TMZ-POH demonstrated evidence of cytotoxicity with 1050 at 150 uM. FIG. 15 shows the results of the MTT cytotoxicity assays performed on USC-04 glioma cancer stem cells treated with POH. POH demonstrated cytotoxicity on USC-04 with increasing concentrations (0-2 mM).

Figure 16:
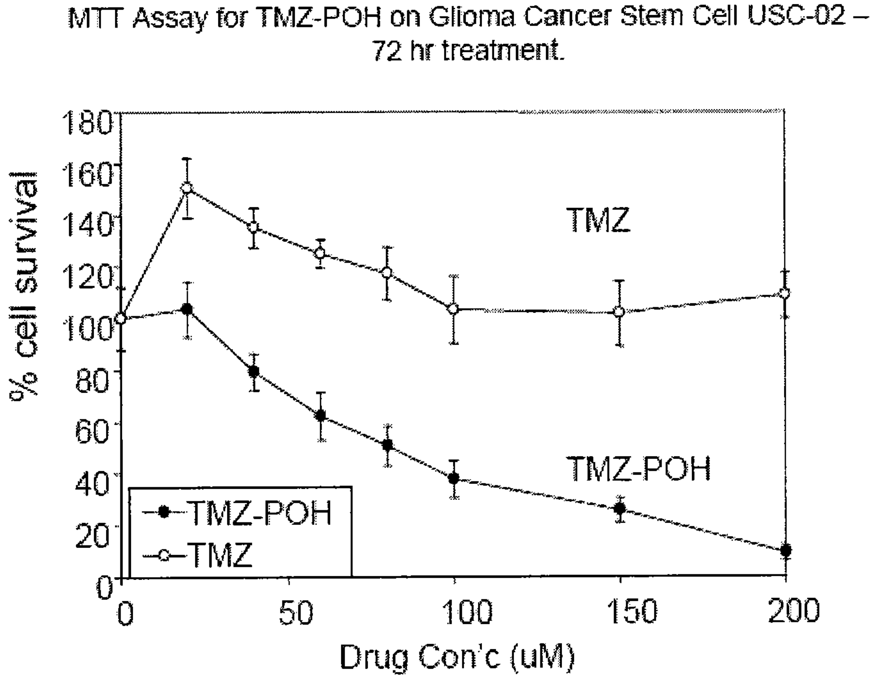
FIG. 16 shows the results of the MTT cytotoxicity assays demonstrating the efficacy of TMZ and the TMZ-POH conjugate in killing USC-02 glioma cancer stem cells.
Figure 17:
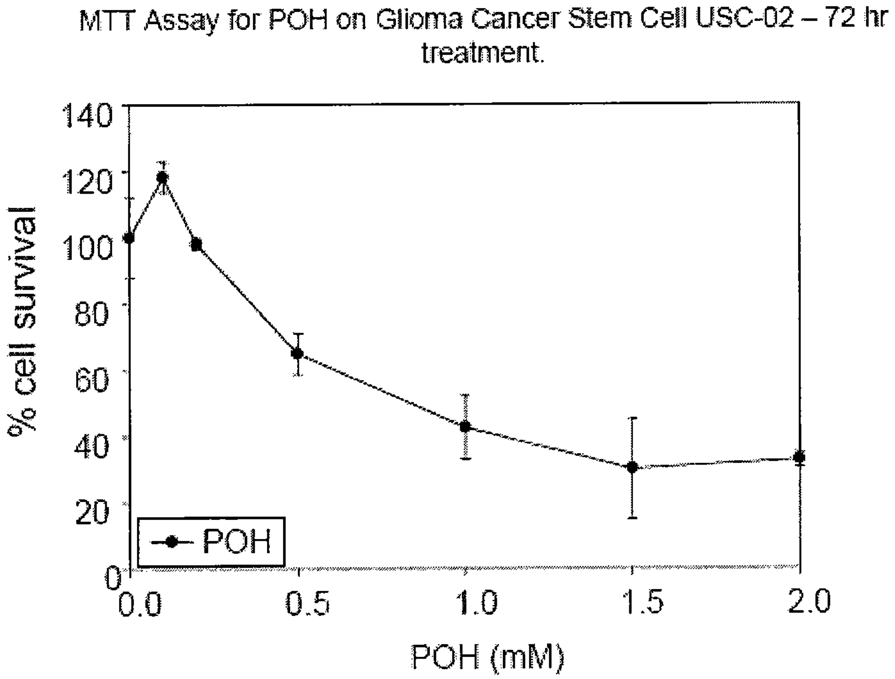
FIG. 17 shows the results of the MTT cytotoxicity assays demonstrating the efficacy of POH in killing USC-02 glioma cancer stem cells.

Example 12: In Vitro Cytotoxicity Studies of TMZ and TMZ-POH on USC-02 Glioma Cancer Stem Cells MTT cytotoxicity assays were carried out after cells were treated with the TMZ alone, POH alone, or the TMZ-POH conjugate. The MTT cytotoxicity assays were carried out as described in Chen T C, et al. Green tea epigallocatechin gallate enhances therapeutic efficacy of temozolomide in orthotopic mouse glioblastoma models. *Cancer Lett.* 2011 Mar. 28; 302(2):100-8. FIG. 16 shows the results of the MTT cytotoxicity assays performed on USC-02 glioma cancer stem cells. TMZ did not induce significant cytotoxicity with increasing concentrations (0-400 uM). TMZ-POH demonstrated evidence of cytotoxicity with 1050 at 60 uM. FIG. 17 shows the results of the MTT cytotoxicity assays performed on USC-02 glioma cancer stem cells treated with POH. POH demonstrated cytotoxicity on USC-02 with increasing concentrations (0-2 mM).

Figure 18:
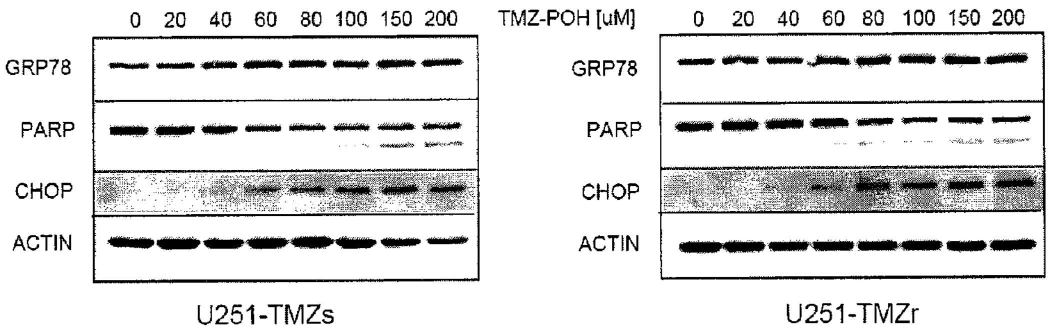
FIG. 18 shows a western blot demonstrating that TMZ-POH induces ER stress (ERS) in TMZ sensitive ("U251-TMZs") and resistant ("U251-TMZr") U251 glioma cells.

Example 13: In Vitro Studies of ER Stress by TMZ-POH on TMZ Sensitive and Resistant Glioma Cells Western blots were performed after TMZ sensitive and resistant glioma cells were treated with the TMZ-POH conjugate for 18 hr. FIG. 18 shows a western blot demonstrating that TMZ-POH induces ER stress (ERS) in TMZ sensitive and resistant U251 glioma cells. Activation of the proapoptotic protein CHOP was shown at concentrations as low as 60 uM of TMZ-POH.

Example 14: In Vitro and In Vivo Studies of TMZ-POH on Certain Breast Cancer Cells Pharmacological Agents TMZ was obtained from the pharmacy at the University of Southern California (USC) and dissolved in ethanol to a concentration of 50 mM. TMZ-POH, which is also referred to as T-P in this example, was provided by NeOnc Technologies Inc. and was dissolved in DMSO at 100 mM. Perillyl alcohol (POH) and O6-benzylguanine (O6-BG) were purchased from Sigma-Aldrich (St. Louis, Mo.) and diluted with DMSO to make stock solutions of 100 mM. DMSO was from Sigma-Aldrich. In all cases of cell treatment, the final DMSO concentration in the culture medium never exceeded 0.5%. Stock solutions of all drugs were stored at −20° C.

Cell Lines

The human cancer cell lines were obtained from the American Tissue Culture Collection (ATCC; Manassas, Va.), except for HCC-1937, which was provided by Dr. Michael Press. Cells were propagated in DMEM (provided by the Cell Culture Core Lab of the USC/Norris Comprehensive Cancer Center and prepared with raw materials from Cellgro/MediaTech, Manassas, Va.) supplemented with 10% fetal bovine serum, 2 mmol/L glutamine, 100 U/mL penicillin, and 0.1 mg/mL streptomycin in a humidified incubator at 37° C. and a 5% $CO_2$ atmosphere.

Colony Formation Assay

Depending on the cell line (and plating efficiency), 200-350 cells were seeded into each well of a 6-well plate. After cells had fully attached to the surface of the culture plate, they were exposed to drug treatment (or DMSO solvent alone) for various times up to 48 hours. Thereafter, the drugs were removed, fresh growth medium was added, and the cells were kept in culture undisturbed for 12-16 days, during which time the surviving cells spawned colonies of descendants. Colonies (defined as groups of >50 cells) were visualized by staining for 4 hours with 1% methylene blue (in methanol), and then were counted.

In the case of O6-BG treatment, cells were pretreated with 10 μM O6-BG for one hour before addition of TMZ or TMZ-POH. After 24 hours, another 10 μM O6-BG was added to the medium. Another 24 hours later, drug-laced medium was removed, and fresh medium without drugs was added. Thereafter, cells remained undisturbed until staining with methylene blue.

Stable Transfections

MDA-MB-231 cells were co-transfected in 6-well plates with the use of Lipofectamine 2000 (Invitrogen, Carlsbad, Calif.) according to manufacturer's instructions. 2 μg pSV2MGMT (containing the human MGMT cDNA) was combined with 0.2 μg pSV2neo (containing the neomycin gene for selection of cells in G418). Both plasmids were provided by Bernd Kaina (Mainz, Germany). Individual clones of transfected cells were selected in medium containing 750 μg/mL G418 and propagated in 250 μg/mL G418. G418 was obtained as G418 disulfate salt from Sigma-Aldrich and dissolved in PBS at 75 mg/mL. Selection medium was removed from cells several days before experimental drug treatment.

Immunoblots

Total cell lysates were analyzed by Western blot analysis as described in P. Pyrko et al. Downregulation of survivin expression and concomitant induction of apoptosis by celecoxib and its non-cyclooxygenase-2-inhibitory analog, dimethyl-celecoxib (DMC), in tumor cells in vitro and in vivo. *Mol Cancer* 5 (2006) 19. The primary antibodies were purchased from Cell Signaling Technology (Beverly, Mass.) or Santa Cruz Biotechnology, Inc. (Santa Cruz, Calif.) and used according to the manufacturers' recommendations. All immunoblots were repeated at least once to confirm the results.

In Vivo Model

All animal protocols were approved by the Institutional Animal Care and Use Committee (IACUC) of University of Southern California, and all rules and regulations were followed during experimentation on animals. Athymic mice (Harlan, Inc., Indianapolis, Ind.) were implanted intracranially with $2\times10^5$ cells. A subline of MDA-MB-231 cells called D3H2LN was used, which was transfected with the firefly luciferase gene and had been selected for aggressive growth and metastasis in vivo. Ten days after intracranial implantation, efficient tumor take was confirmed in all animals via non-invasive whole-body bioluminescent imaging. For this purpose, mice were intravenously injected with 50 mg/kg D-Luciferin (Perkin Elmer, Waltham, Mass.) and imaged using the Xenogen IVIS-200 Imaging System (Caliper/Perkin Elmer). Images were analyzed by region-of-interest (ROI) analysis using the Living Image software package (Caliper/Perkin Elmer) to quantitate light output (radiance, i.e., photons per second per square centimeter per steradian).

Animals were distributed into three groups so that each group contained animals with comparable radiance within the ROI (i.e., area of the head) and drug treatment was initiated. Group 1 was the control group that received vehicle only (45% glycerol, 45% ethanol, 10% DMSO) via subcutaneous injection. Group 2 was the experimental group that received 25 mg/kg TMZ-POH via subcutaneous (s.c.)

injection. Group 3 was the comparison group and animals received 25 mg/kg TMZ via gavage. Treatment was once per day for a period of 10 days (i.e., 10 treatments total). Thereafter, all surviving animals were imaged again, once per week.

Statistical Analysis

All parametric data were analyzed using the Student t-test to calculate the significance values; a probability value (p)<0.05 was considered statistically significant.

Results

Figure 19:
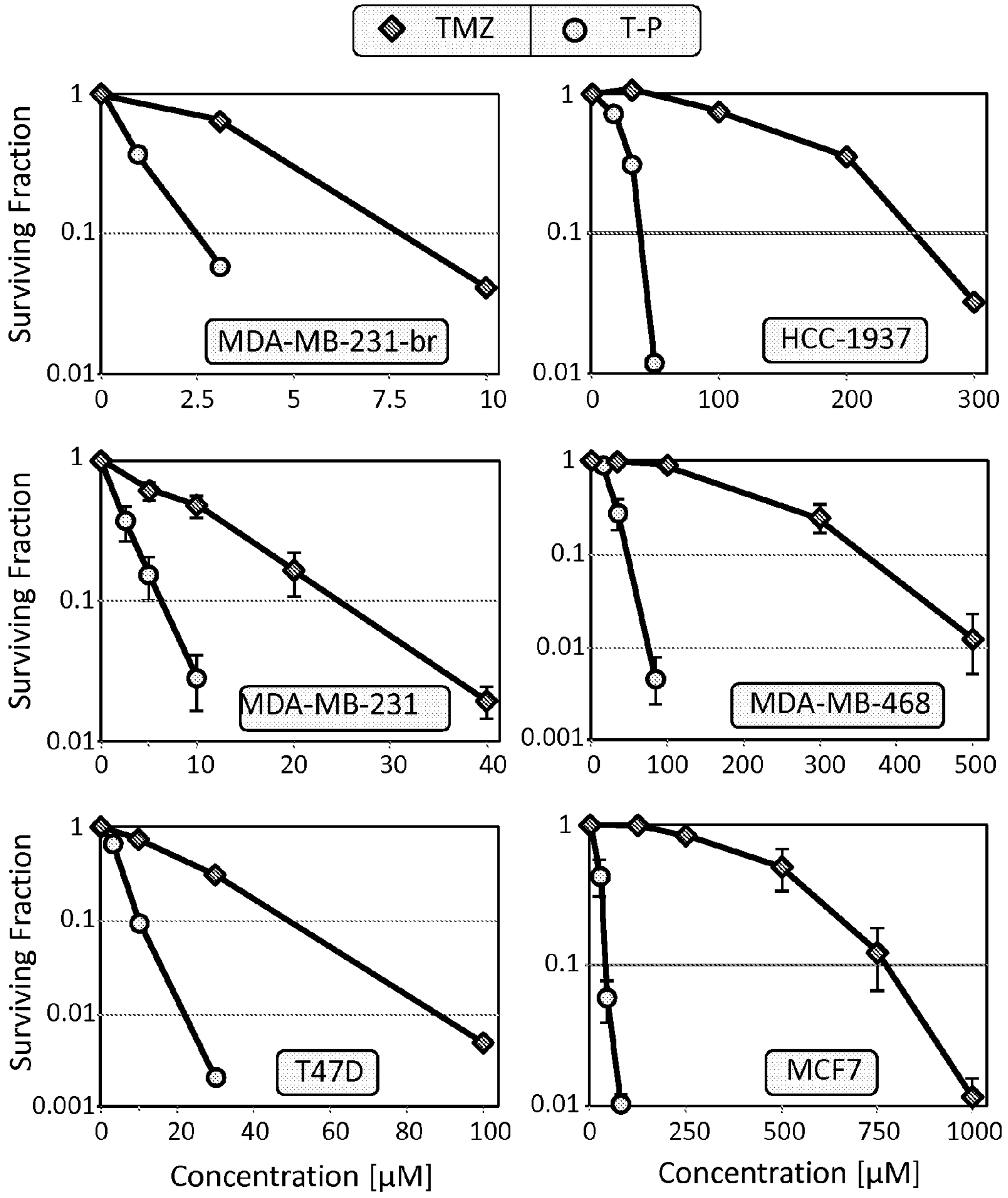
FIG. 19 shows survival of breast cancer cells after drug treatment, where various breast cancer cell lines were exposed to increasing concentrations of TMZ or TMZ-POH for 48 hours, and survival was determined via colony formation assay (CFA). Shown is the fraction of colony-forming cells, where colony formation by control cells (treated with DMSO vehicle only) is set at 1. Graphs with error bars display mean (±SD) from ≥3 independent experiments; graphs without error bars show the average from two independent experiments.

The cytotoxic potency of TMZ-POH, was analyzed by colony formation assay (CFA) in a variety of human breast cancer cell lines and compared to the cytotoxicity of TMZ. We used estrogen receptor positive cells MCF7 and T47D, the triple-negative lines MDA-MB-231, MDA-MB-468, and HCC-1937, and a brain-seeking variant of the 231 cell line, MDA-MB-231-br. As shown in FIG. 19, low micromolar concentrations of TMZ-POH prevented colony formation in all six cell lines, and in all instances TMZ-POH's potency was substantially stronger than that of TMZ.

Figure 20A:
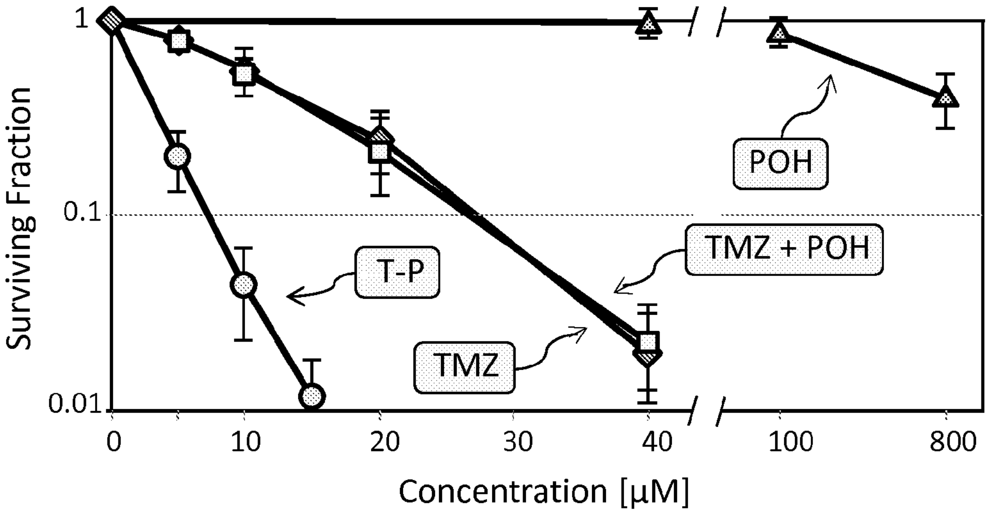
FIGS. 20A-20B show cytotoxic potency of TMZ-POH and its individual components, where survival of drug-treated MDA-MB-231 cells was determined by CFA.
Figure 20B:
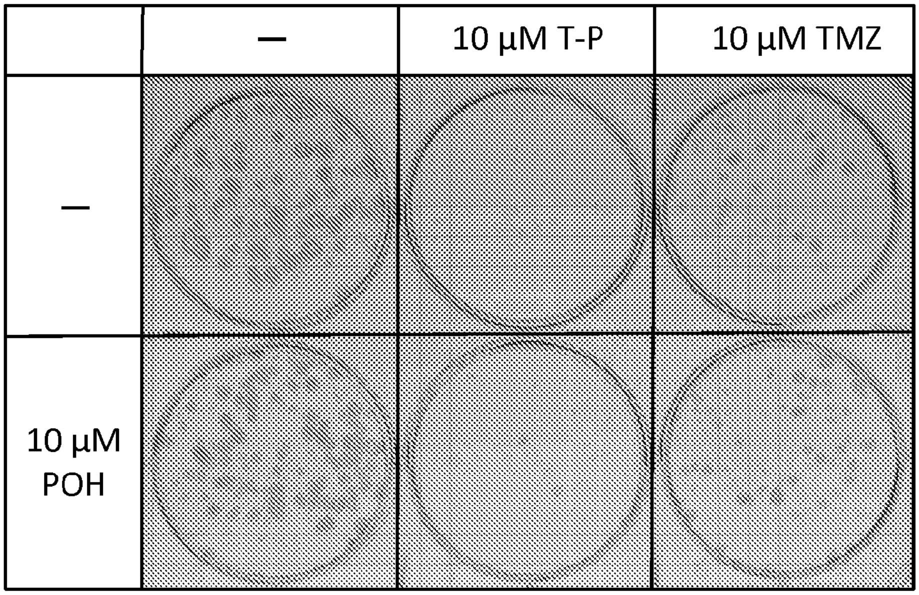

Previous studies showed that POH is able to exert cytotoxic effects in cancer cells, although concentrations approaching the millimolar range were required. Thus, we tested whether simply mixing the two compounds TMZ and POH could mimic the effects of the TMZ-POH conjugate. MDA-MB-231 cells were treated with the individual compounds (TMZ-POH, TMZ or POH) alone, or with an equimolar mix of TMZ plus POH, and cell survival was analyzed by CFA. As shown in FIGS. 20A and 20B, TMZ-POH was much more potent than a mix of TMZ plus POH, i.e., mixing TMZ with POH was unable to achieve the strong cytotoxic potency of TMZ-POH, and in fact, the addition of equimolar concentrations of POH to TMZ did not increase the potency over TMZ alone. For instance, 10 μM TMZ reduced colony formation by about 50%, and the combination of 10 μM TMZ with 10 μM POH also caused a 50% reduction; in comparison, 10 μM TMZ-POH caused about 95% fewer colonies (FIG. 20A). Consistent with earlier reports, POH by itself required concentrations well above 100 μM in order to become cytotoxic, and its IC50 in MDA-MB-231 cells was about 700 μM (FIG. 20A).

FIG. 20B shows a representative example of an individual CFA. It illustrates that 10 μM blocks colony formation substantially more potently than TMZ, and that the addition of equimolar concentrations of POH to either TMZ or TMZ-POH is unable to enhance toxicity any further. Altogether, the above results shows that TMZ-POH has with increased potency over TMZ that cannot be matched by merely mixing its individual parts, TMZ and POH.

Figure 21A:
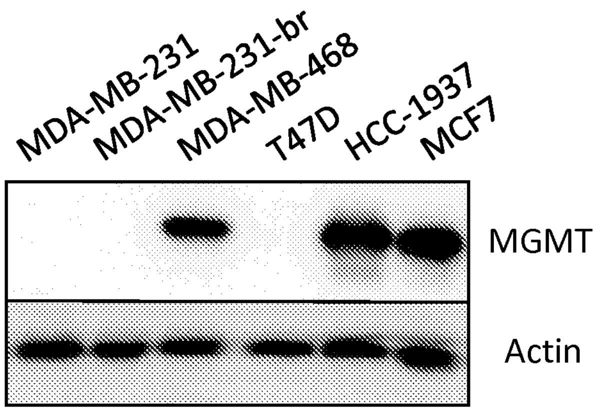
FIGS. 21A-21C show MGMT expression levels in various cell lines, where all parts show Western blot analysis of MGMT protein levels with actin as the loading control.
Figure 21B:
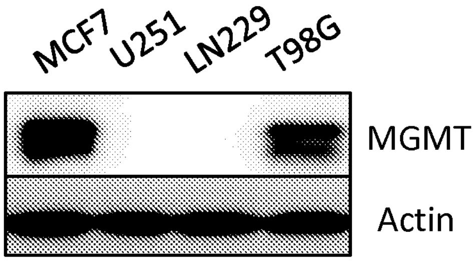

Because the DNA repair protein MGMT is known to play a key role in cellular resistance to TMZ, we investigated how it would impact the cytotoxic potency of TMZ-POH. We first determined its basal level of expression in the six breast cancer cell lines we used above. FIG. 21A shows that three cell lines (MDA-MB-468, HCC-1937, MCF7) were strongly positive, whereas the others (T47D, MDA-MB-231, MDA-MB-231-br) had undetectable levels of MGMT protein, as determined by Western blot analysis. For comparison purposes, we also assessed MGMT protein levels in three commonly used GBM cell lines known to be MGMT negative (U251, LN229) and positive (T98G). This side-by-side evaluation revealed that MGMT protein levels in the positive breast cancer lines were similar to the levels found in the T98G brain cancer line.

MGMT expression was aligned with the cytotoxic potency of TMZ-POH in comparison to TMZ. As summarized in Table 2, the IC50 of TMZ-POH (i.e., the concentration required to decrease colony formation by 50%) was noticeably higher in all three MGMT-positive breast cancer cell lines. Whereas the IC50 in MGMT-negative cell lines ranged from 1.2 to 4.6 μM, it increased to 31 to 33 μM in the three MGMT-positive lines. Nonetheless, these IC50 values still were substantially lower than the corresponding IC50s of TMZ for each cell line. Noteworthy as well is the differential (fold increase in potency) between TMZ-POH and TMZ shown in Table 2: The fold-increase in cytotoxic potency of TMZ-POH, as compared to TMZ, is consistently greater in each of the MGMT-positive cell lines (6.3 to 15.5-fold) as compared to the MGMT-negative cell lines (3.2 to 4.3-fold). This latter finding suggests that the increased potency of TMZ-POH over TMZ, although apparent in all cell lines analyzed, might become particularly advantageous in the context of therapeutically targeting MGMT-positive cells.

TABLE 2

Drug Sensitivities of Various Breast Cancer Cell Lines

| Cell Line | MGMT status | IC50 TMZ (μM) | IC50 T-P (μM) | Differential (−fold) |
|---|---|---|---|---|
| MDA-MB-231-br | − | 3.8 | 1.2 | 3.2 |
| MDA-MB-231 | − | 9.9 | 2.3 | 4.3 |
| T47D | − | 20 | 4.6 | 4.3 |
| HCC-1937 | + | 186 | 31 | 6.0 |
| MDA-MB-468 | + | 195 | 31 | 6.3 |
| MCF7 | + | 513 | 33 | 15.5 |

Figure 21C:
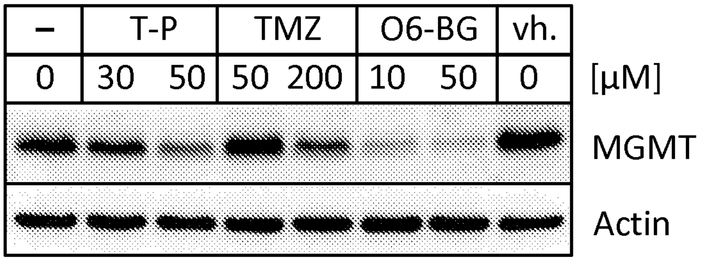

The major cytotoxic DNA lesion set by TMZ is methylation of O6-guanine, and it is well known that removal of this methyl group by MGMT leads to rapid degradation of the DNA repair protein. As well, the pseudosubstrate O6-BG also activates the suicide mechanism of MGMT, which is confirmed in FIG. 21C, showing that treatment of cells with O6-BG strongly decreases MGMT protein levels. Treatment of cells with TMZ also down-regulates MGMT levels, but the effect is fairly weak and high concentrations of the drug are required. In comparison, TMZ-POH affects MGMT levels more potently than TMZ; for instance, while 50 μM TMZ has no effect, 50 μM TMZ-POH causes a significant decrease (FIG. 21C). Together, these results indicate that TMZ-POH's superior potency over TMZ may involve more extensive methylation of O6-guanine targets.

While the above results suggested that TMZ-POH's mechanism of action might be due to the drug's increased efficacy of setting cytotoxic DNA lesions, there was also a possibility that covalently conjugating POH might have conferred additional mechanistic features to the new molecule. Additional experiments were performed to characterize the significance of DNA damage, and in particular O6-guanine methylation, caused by TMZ-POH.

Figure 22A:
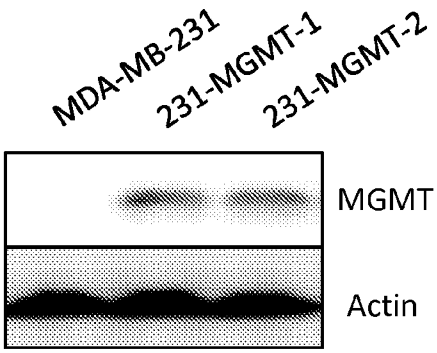
FIGS. 22A-22B show drug sensitivity of MGMT-transfected cells, where MDA-MB-231 cells were stably transfected with MGMT cDNA.
Figure 22B:
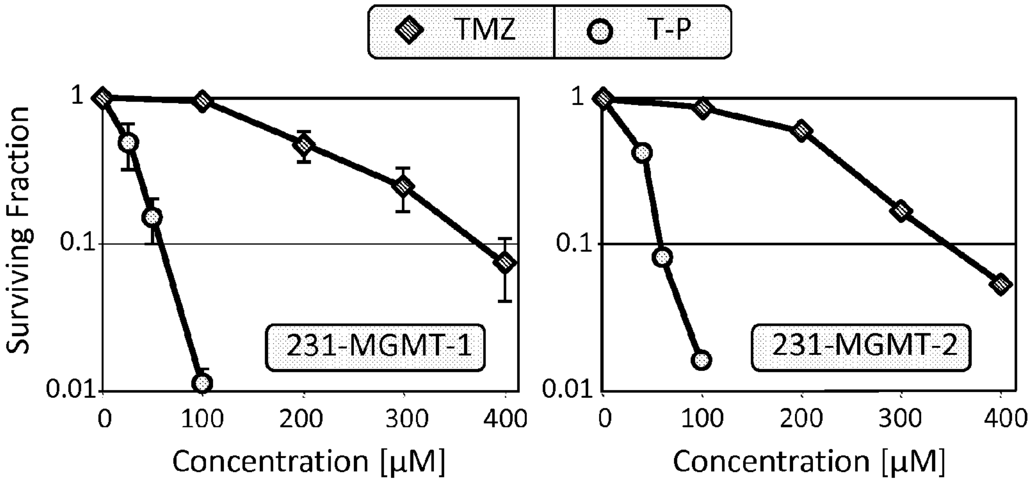

While the experiments summarized in Table 2 revealed a correlation of MGMT positivity with decreased TMZ-POH toxicity, they did not establish cause and effect. To investigate the latter, we stably transfected MGMT-negative MDA-MB-231 cells with MGMT cDNA and isolated individual clones. FIG. 22A shows elevated expression of MGMT protein in two different clones (231-MGMT-1 and 231-MGMT-2) of transfected cells. Both clones were treated with increasing concentrations of TMZ-POH and TMZ and analyzed by CFA. As shown in FIG. 22B and Table 3, resistance of cells to drug treatment clearly increased for both TMZ-POH and TMZ, as compared to parental cells. Intriguingly however, similar to what was noted in Table 2, resistance to TMZ-POH increased less than resistance to TMZ (summarized in Table 3).

TABLE 3

Drug Sensitivities of Cells Transfected with MGMT cDNA

| Cell Line | MGMT status | IC50 TMZ (μM) | IC50 T-P (μM) | Differential (−fold) |
|---|---|---|---|---|
| MDA-MB-231 | − | 9.9 | 2.3 | 4.3 |
| 231-MGMT-1 | + | 202 | 27 | 7.5 |
| 231-MGMT-2 | + | 212 | 34 | 6.2 |

Figure 23A:
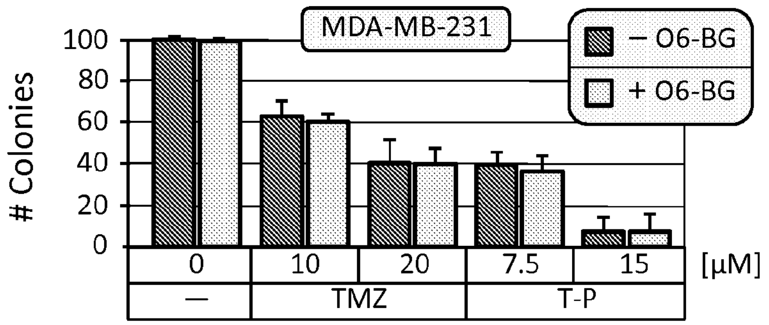
FIGS. 23A-23C show effect of inclusion of O6-BG, where cells were exposed to TMZ or TMZ-POH for 48 hours in the presence or absence of O6-BG, and cell survival was determined by CFA.
Figure 23B:
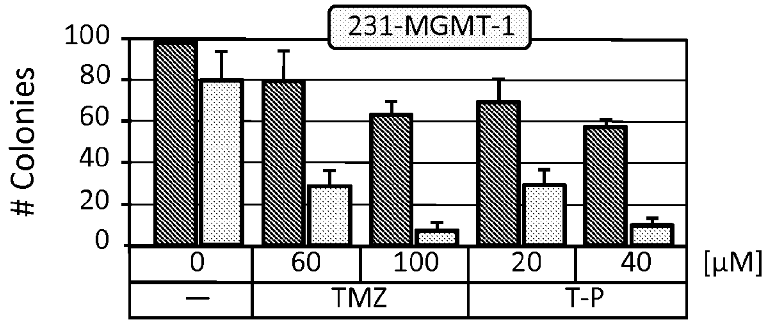
Figure 23C:
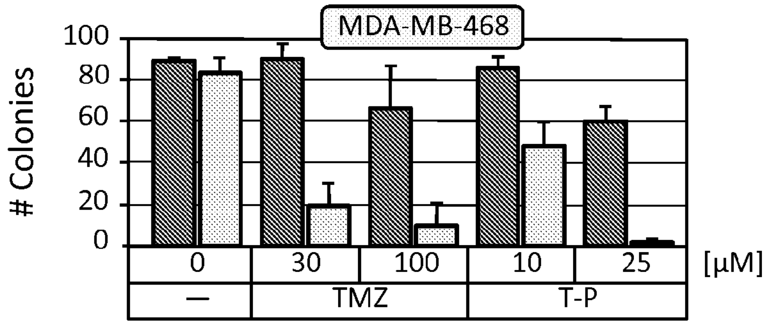

CFAs were also performed with the addition of the MGMT inhibitor O6-BG. Cells were pre-treated with O6-BG for 60 minutes before addition of TMZ-POH or TMZ. As shown in FIG. 23A, O6-BG had no effect on the survival of drug-treated MDA-MB-231 cells, consistent with their MGMT-negative status that does not provide a target for O6-BG. In contrast, O6-BG greatly enhanced toxicity of TMZ-POH and TMZ in 231-MGMT-1 (FIG. 23B) and 231-MGMT-2 cells (not shown). Similarly, O6-BG also increased the cytotoxic outcome of TMZ-POH and TMZ treatment in MGMT-positive MDA-MB-468 (FIG. 23C) and MCF7 cells (not shown). Altogether, these results indicate that the key trigger for cell death caused by TMZ-POH is methylation of O6-guanine, which appears to be achieved much more effectively by TMZ-POH as compared to TMZ.

Figure 24A:
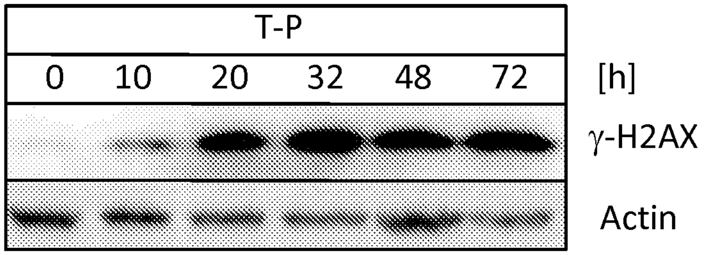
FIGS. 24A-24D show drug effects on DNA damage marker, where cells were treated with different concentrations of TMZ-POH or TMZ and analyzed by Western blot analysis for expression levels of γ-H2AX, a marker for double-strand DNA damage. Actin was used as a loading control. MDA-MB-231 cells were treated with 50 μM TMZ-POH for the indicated time periods (FIG. 24A); MDA-MB-231 cells were treated with 50 μM TMZ-POH or 50 μM TMZ for the indicated time periods (FIG. 24B); MDA-MB-231 cells were treated with TMZ-POH, TMZ, POH, or TMZ combined with POH (all at 10 μM each) for 24 hours (FIG. 24C); MCF7 cells were treated with or without 50 μM TMZ-POH in the presence or absence of 30 μM O6-BG for 48 hours (FIG. 24D).
Figure 24B:
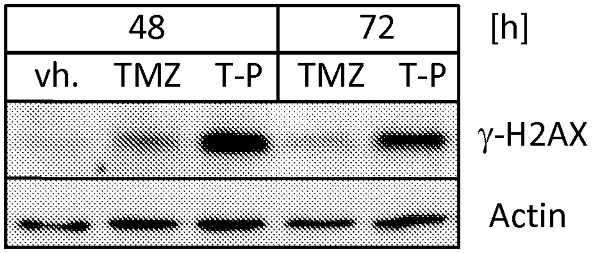
Figure 24C:
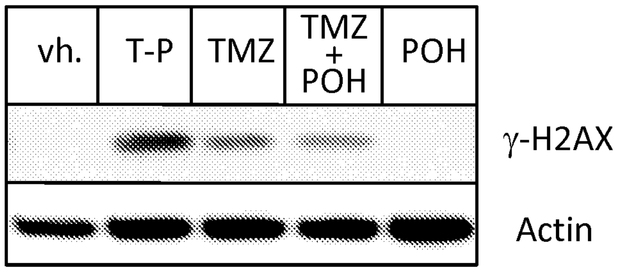

The above conclusion was further confirmed by studying H2AX protein. Phosphorylation of H2AX, noted as γ-H2AX, is a marker for double strand breaks in DNA. MDA-MB-231 cells treated with TMZ-POH over a time course of 72 hours revealed substantially increased levels of γ-H2AX (FIG. 24A), and this effect of TMZ-POH was much stronger as compared to TMZ (FIG. 24B). As well, the mere combination of TMZ with POH was unable to mimic the strong induction of γ-H2AX caused by conjugated TMZ-POH (FIG. 24C), consistent with the CFA results shown in FIG. 20 and the notion that TMZ-POH represents a chemical entity different from the mix of TMZ plus POH.

Figure 24D:
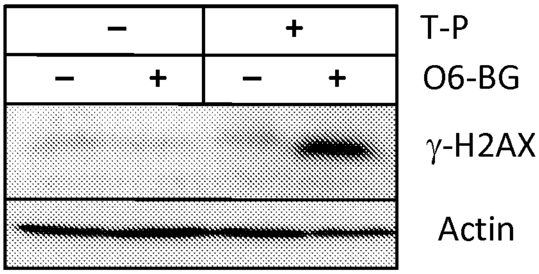

The same concentration of TMZ-POH that was applied to MDA-MB-231 cells was also added to MGMT-positive MCF-7 cells. However, in this case, there was no increased phosphorylation of H2AX, consistent with the established model that MGMT rapidly repairs O6-methyl-guanine lesions; however, when these cells were pre-treated with O6-BG, increased levels of γ-H2AX became readily apparent (FIG. 24D). In sum, the above results indicate TMZ-POH as an alkylating agent with cytotoxic mechanism similar to TMZ, but with potency that is substantially greater than the original compound.

Figure 25A:
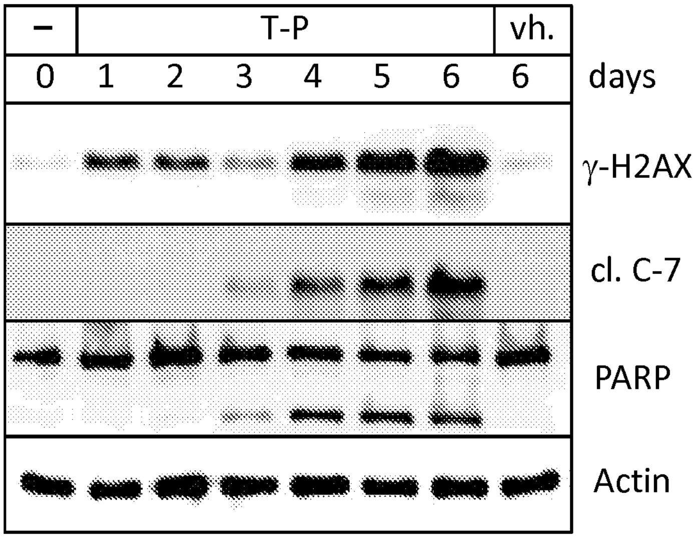
FIGS. 25A-25B show DNA damage and cell death marker analysis, where MDA-MB-231 cells were used for Western blot analysis of expression levels for markers of DNA damage (γ-H2AX) and cell death (activated caspase 7 and cleaved PARP).

It is known that GBM cells treated with physiological concentrations of TMZ (<100 μM) in vitro can survive for several (5-7) days seemingly unaffected before substantial cell death becomes apparent. We observed a similar phenotype when breast cancer cell lines were treated with TMZ-POH, i.e., cell cultures only began to deteriorate approximately a week after the onset of drug treatment. In order to characterize TMZ-POH-induced cell death in greater detail, we treated MDA-MB-231 cells with 15 μM of the drug and collected cell lysates daily over the course of 6 days. The lysates were analyzed by Western blot for the presence of two apoptosis markers, cleaved (i.e. activated) caspase 7 and cleaved PARP-1 (poly ADP-ribose polymerase-1), along with the DNA damage marker γ-H2AX. As above, TMZ-POH treatment resulted in pronounced increase in γ-H2AX expression levels, which except for an unexplained dip at 3 days continued to increase over time (FIG. 25A). Both active caspase 7 and cleaved PARP started to increase at day 3 and remained elevated for several more days until day 6 (FIG. 25A), which is about the time when microscopic examination of treated cells reveals increasing deterioration of the monolayer. These results indicate that TMZ-POH-induced cell death, similar to what has been reported for physiological concentrations of TMZ, is a slow process and involves apoptotic mechanisms.

Figure 25B:
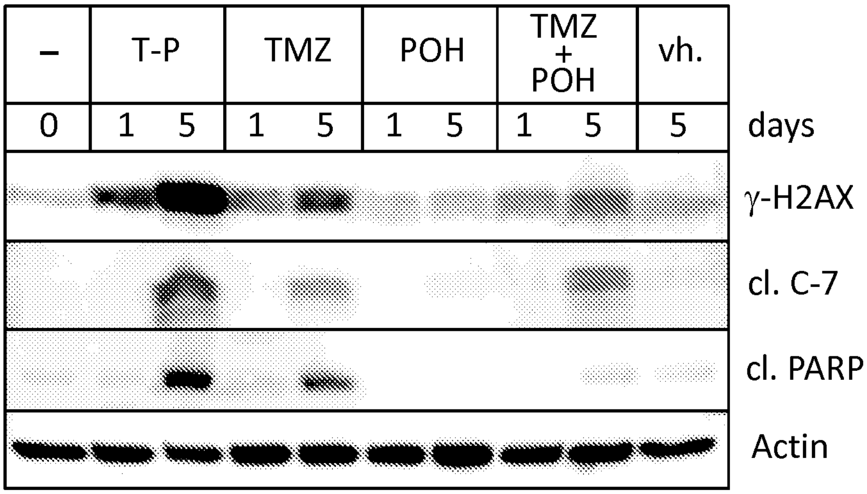

As shown in FIGS. 20A-20B above, an equimolar combination of TMZ+POH was unable to achieve the same potency in blocking colony survival as the TMZ-POH conjugate. Having established TMZ-POH's impact on DNA damage and its activation of apoptosis, we next determined whether TMZ-POH's superior effect would also be reflected at the molecular level of these marker proteins. We treated cells with the same concentration (20 μM) of TMZ-POH, TMZ, POH, or TMZ combined with POH (TMZ+POH), and analyzed the induction of γ-H2AX, activated caspase 7, and cleaved PARP. As shown in FIG. 25B, all three indicator proteins were induced quite prominently by TMZ-POH after 5 days of treatment, whereas TMZ or TMZ+POH exerted noticeably weaker effects and POH alone was inactive in these measurements. Thus, the results from the cell survival assay (FIGS. 20A-20B) correlated closely with the effects of these compounds on DNA damage and apoptosis markers (FIG. 25B), and in all cases TMZ-POH clearly generated the strongest anticancer impact.

TMZ is a prodrug, and it is well known that its activation takes place spontaneously in aqueous solution at 37° C. (i.e., no cellular functions are required for this conversion). As well, the half-lives of both prodrug and active product are fairly short, where all cytotoxic triggers are set within the first few hours of treatment. To evaluate whether TMZ-POH and TMZ differed in their half-lives, we determined how quickly, and for how long, the drugs exhibited cytotoxic activity in cell culture. First, we exposed cells to variably short periods of drug treatment, washed off the drug, and then continued to keep cells in medium without drug to determine survival and colony-forming ability. For most of these experiments, we used 15 μM TMZ-POH and 30 μM TMZ, because these concentrations are approximately equipotent in the >90% cytotoxicity range (when measured by CFAs and a drug exposure time of 24 hours).

Figure 26A:
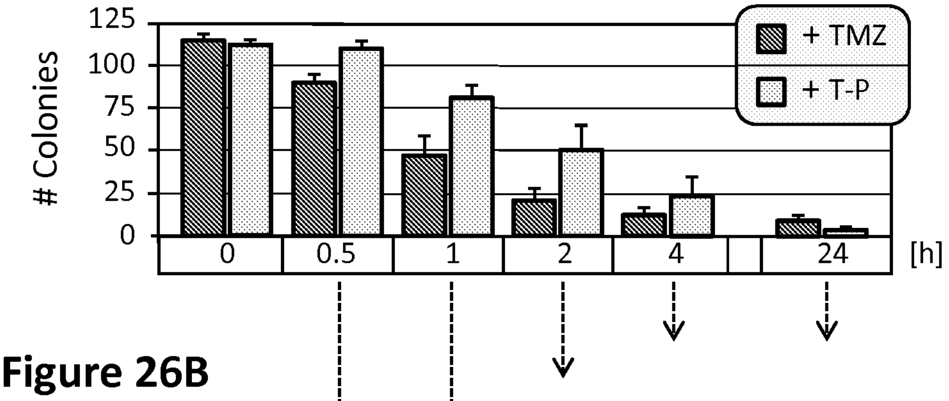
FIGS. 26A-26C depicts determination of drug stability, where MDA-MB-231 cells were analyzed in colony formation assays.

As shown in FIG. 26A (right two bars), exposure of cells to 15 μM TMZ-POH or 30 μM TMZ resulted in about 3% and 8% colony survival, respectively, when drugs remained in the medium for 24 hours. Yet, despite TMZ-POH unfolding slightly more potency over the course of 24 hours, TMZ displayed noticeably greater efficacy when cells were exposed for shorter time periods. As shown in FIG. 26A, a one-hour exposure to TMZ reduced colony formation by >50%, whereas during the same time period TMZ-POH reduced it by only 20%; similarly, a two-hour exposure to TMZ had more than double the cytotoxic impact (23% survival) than TMZ-POH (51%). Thus, TMZ acted more quickly than TMZ-POH; it required only 4 hours to exert maximum toxicity, whereas TMZ-POH had not yet reached its maximum impact at this time point.

Figure 26B:
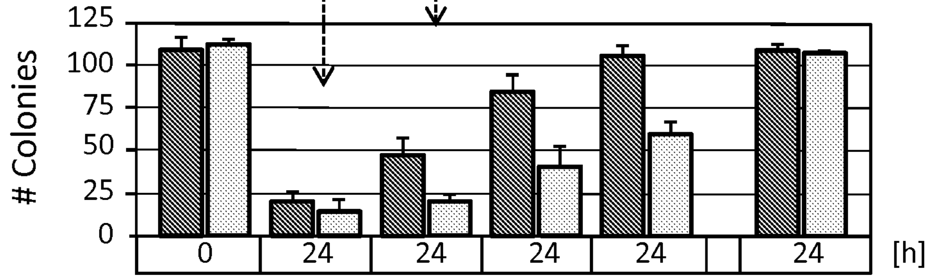

We next modified this experiment as follows. After cells had been exposed to drug treatment for the specific times shown in FIG. 26A, we removed the medium containing the drug from the cells, and transferred this supernatant to fresh cells, which were then exposed for 24 hours. As shown in FIG. 26B (right two bars), when supernatant was transferred after prior 24-hours of incubation, no cytotoxic activity remained, i.e., there was no reduction in colony-forming ability of the receiving cells. In contrast, when supernatant was transferred after prior one-hour incubation, colony-forming ability of receiving cells was 48% in cells receiving TMZ-containing supernatant, and 22% in TMZ-POH-containing supernatant. Even more strikingly, TMZ-containing supernatant had lost all of its activity when transferred after 4 hours, whereas TMZ-POH-containing supernatant still contained nearly 50% of its cytotoxic activity (FIG. 26B). Together, these results demonstrate that TMZ-POH retained its cytotoxic potency substantially longer than TMZ.

Figure 26C:
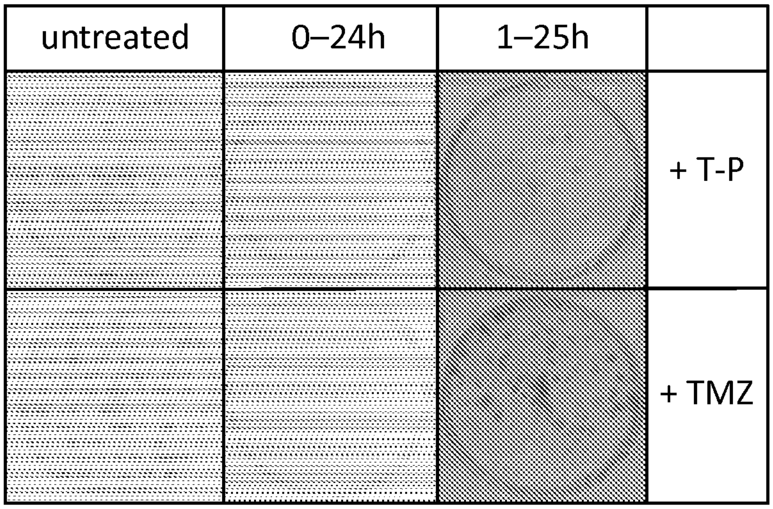

To exclude the involvement of cellular enzymes in the turnover of TMZ-POH, we incubated TMZ-POH (and TMZ) in phosphate-buffered saline at 37° C. for one hour (in the absence of cells). After this pre-incubation, TMZ-POH and TMZ were added to cells for 24 hours, and survival was determined by CFA. As a control, both drugs were also added to cells without prior incubation in aqueous solution. A representative CFA is shown in FIG. 26C, where the middle panel confirms that both drugs were used at approximately equipotent concentrations; i.e., when added straight to cells, they reduced survival by ~95%. However, pre-incubation in aqueous solution for only one hour preempted the cytotoxic potency of TMZ by about 50%, but that of TMZ-POH much less (80% remaining; see right panel). These results establish that TMZ-POH is more stable than TMZ, suggesting that its increased potency over TMZ might be due to longer half-life, which may provide for extended opportunity to inflict cytotoxic DNA damage.

We also investigated whether TMZ-POH would be able to exert its anticancer effects in vivo as well, and whether it would be able to do so with a mouse tumor model representing breast cancer spread to the brain. We used D3H2LN cells, which are a bioluminescent variant of the MDA-MB-231 cell line with aggressive tumor growth in mice. These cells were implanted into the brains of nude mice, and 10 days later all animals were imaged for luciferase expression in order to confirm efficient tumor take.

Figure 27A:
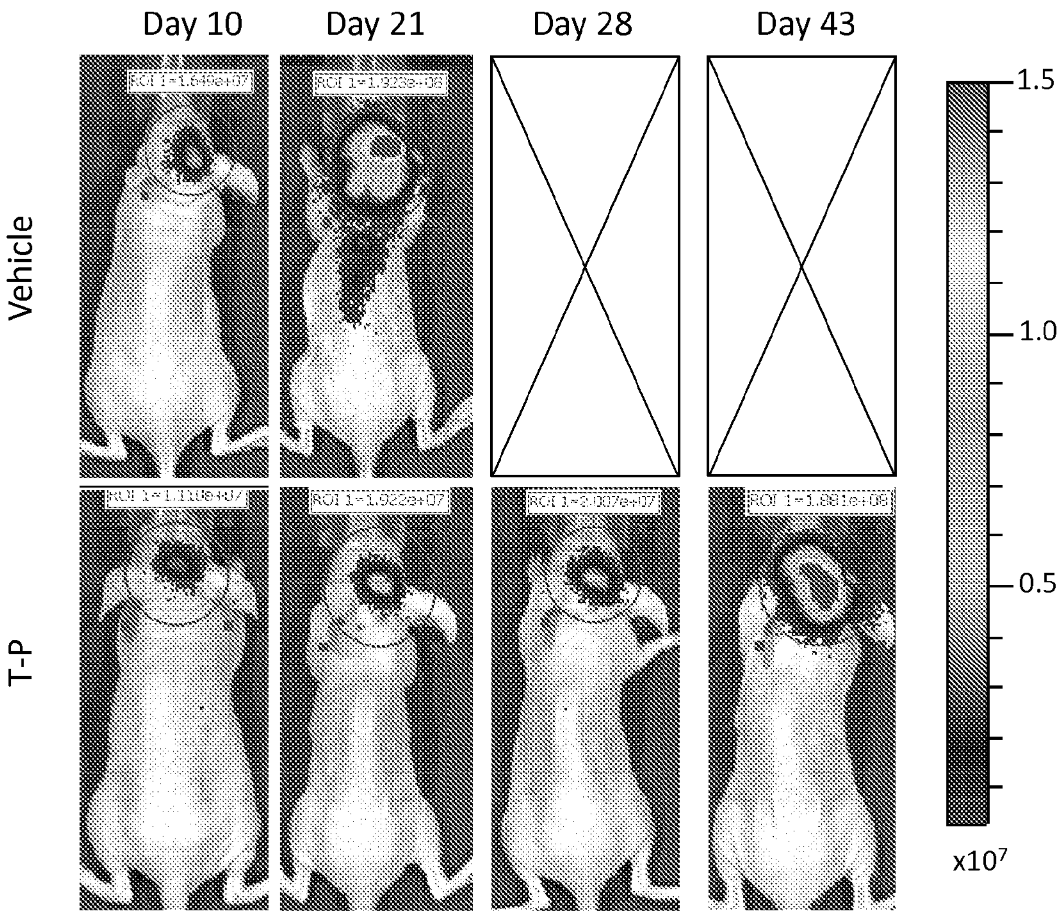
FIGS. 27A-27B show drug effects on intracranial tumor growth, where luciferase-positive D3H2LN cells were implanted into the brains of 24 nude mice. Ten days later, tumor take was confirmed via bioluminescent imaging, and treatment was initiated with vehicle only (control group), 25 mg/kg TMZ-POH, or 25 mg/kg TMZ, once daily over the course of 10 days.

Animals were distributed into three groups and treated once daily for 10 days with vehicle alone (control), 25 mg/kg TMZ-POH, or 25 mg/kg TMZ. Another whole-body imaging after this 10-day treatment period showed (FIG. 27A) that all vehicle-only treated animals exhibited much increased bioluminescent radiance (indicative of vigorous intracranial tumor growth), some of which had conspicuously spread along the spine. Most of these animals also exhibited behavioral signs of neurological problems and reduced body weight, which necessitated euthanasia. In stark contrast, all animals in the TMZ-POH-treated group seemed to thrive, and their imaging analysis showed only small changes in radiance (FIG. 27A). In comparison, all animals in the TMZ-treated group showed clearly increasing bioluminescence over time, indicating that tumor growth had continued throughout the 10-day treatment period, and had begun to include the spine in some of the animals. Overall, the TMZ-treated group seemed to have fared somewhat better than the vehicle-treated group, but clearly worse than the animals treated with TMZ-POH.

All animals were cared for and observed in the absence of any further drug treatment. As summarized in FIG. 27B, vehicle-treated animals were moribund by day 20 and had to be euthanized within the following four days (median survival: 22 days). TMZ-treated animals survived somewhat longer (median survival: 28 days). Remarkably, by day 36, when all TMZ-treated animals had succumbed to disease, all TMZ-POH-treated animals were still alive with no obvious signs of distress. Median survival of TMZ-POH-treated animals turned out to be 50 days, i.e., they survived an additional 30 after the termination of treatment, as compared to TMZ-treated animals, which survived only an additional 8 days after treatment. Altogether, these results demonstrate potent anticancer effects of TMZ-POH that are considerably stronger than those of TMZ in vitro and in vivo.

Discussion

A landmark phase III trial completed 10 years ago established a significant survival benefit for the alkylating agent temozolomide when added to radiotherapy (plus surgery when possible) for newly diagnosed glioblastoma. R. Stupp et al., Radiotherapy plus concomitant and adjuvant temozolomide for glioblastoma. *N Engl J Med* 352 (2005) 987-996. TMZ prolonged median survival from 12.1 to 14.6 months, and increased 5-year overall survival 5-fold from 1.9 to 9.8%. R. Stupp et al., Effects of radiotherapy with concomitant and adjuvant temozolomide versus radiotherapy alone on survival in glioblastoma in a randomised phase III study: 5-year analysis of the EORTC-NCIC trial. *Lancet Oncol* 10 (2009) 459-466. Altogether, these positive outcomes have cemented TMZ plus radiotherapy as the current standard of care for most patients with GBM. As would be expected, this approach was also evaluated for activity against intracranial metastases secondary to primary tumors of the lung, breast, and other extracranial sites. However, the results of several phase II trials in heavily pretreated patients were not impressive enough to establish this regimen as a standard of care for instances of metastatic spread to the brain from cancers such as breast carcinoma. We therefore sought to create a novel analog of TMZ with superior activity against brain metastases.

In the past, extensive molecular modeling studies of antitumor imidazotetrazines including TMZ, showed that the initial activating ring-opening reaction, involving nucleophilic addition at C-4 of the tetrazinone ring, is not affected by bulky moieties at C-8. J. Arrowsmith, S. A. Jennings, A. S. Clark, M. F. Stevens, Antitumor imidazotetrazines, 41. Conjugation of the antitumor agents mitozolomide and temozolomide to peptides and lexitropsins bearing DNA major and minor groove-binding structural motifs, *J Med Chem* 45 (2002) 5458-5470; A. S. Clark et al., Antitumor imidazotetrazines. 32. Synthesis of novel imidazotetrazinones and related bicyclic heterocycles to probe the mode of action of the antitumor drug temozolomide, *J Med Chem* 38 (1995) 1493-1504; E. Lunt et al. Antitumor imidazotetrazines. 14. Synthesis and antitumor activity of 6- and 8-substituted imidazo[5,1-d]-1,2,3,5-tetrazinones and 8-substituted pyrazolo[5,1-d]-1,2,3,5-tetrazinones, *J Med Chem* 30 (1987) 357-366. Therefore, irrespective of the nature of the targeting group conjugated at C-8, the final step in the activation process releases the electrophilic methyldiazonium ion that methylates nucleophilic sites in DNA. Based on these earlier structural and bioactivity studies, we expected that TMZ-POH would preserve the release of the reactive methyldiazonium, and therefore that the cytotoxic activity of TMZ-POH would involve DNA methylation, similar to its parental molecule TMZ.

Our data are consistent with the above mechanistic model. For instance, we show that the presence of MGMT, which highly specifically repairs O6-methylguanine and provides profound protection against TMZ, minimizes DNA damage caused by TMZ-POH (FIG. 24D) and increases cellular resistance to this agent (FIG. 22B). Conversely, the presence of O6-BG, a specific inhibitor of MGMT, substantially enhances DNA damage caused by TMZ-POH (FIG. 24D) and increases this agent's cytotoxic potency exclusively in MGMT-positive cells (FIG. 23). As well, TMZ-POH treatment of cells leads to a reduction in MGMT protein levels (FIG. 21C), which is a well-established effect in the case of TMZ, due to the DNA repair enzyme's "suicide" mechanism of action, whereby acceptance of the alkyl group from O6-methylguanine leads to the protein's rapid degradation.

While our data establish DNA alkylation by TMZ-POH as a key mechanism by which this agent exerts its cytotoxic effect, we cannot exclude the possibility that its POH moiety may contribute additional functions. POH is known to affect several intracellular processes. For instance, it has been shown to inhibit the activity of telomerase and of sodium-potassium pump (Na+/K+-ATPase) [52; 53]. As well, it has been described as a farnesyl-transferase inhibitor that results in the blockage of ras oncoprotein activity (I. R. et al., Inhibition of protein by metabolites of limonene. *Biochem Pharmacol* 57 (1999) 801-809; P. L. Crowell et al., Selective inhibition of isoprenylation of 21-26-kDa proteins by the anticarcinogen d-limonene and its metabolites. *J Biol Chem* 266 (1991) 17679-17685), although this has been challenged (J. Karlson et al Inhibition of tumor cell growth by monoterpenes in vitro: evidence of a Ras-independent mechanism of action, *Anticancer Drugs* 7 (1996) 422-429; R. J. Ruch et al., Growth inhibition of rat liver epithelial tumor cells by monoterpenes does not involve Ras plasma membrane association, *Carcinogenesis* 15 (1994) 787-789.). Importantly, in all these cases relatively high concentrations of POH (well above 100 μM) are required to achieve 50% inhibition of target activity (see also FIG. 20A). In comparison, TMZ-POH is active in the range of 1-5 μM in MGMT-negative cells (Table 2). Notably as well, when POH is mixed with TMZ and applied as a separate agent, this combination is unable to replicate the high potency of conjugated TMZ-POH (FIGS. 20A-20B, 24C, 25B), indicating that the mere presence of non-conjugated POH is unable to provide additional potency over TZM. These considerations, combined with TMZ-POH's notable sensitivity to MGMT and O6-BG as detailed above, diminish the likelihood for involvement of functions other than DNA damage.

If conjugation of POH indeed does not provide additional pro-apoptotic mechanisms over TMZ alone, why is TMZ-POH significantly more potent than TMZ? It has been well established that TMZ (and its active degradation product) exhibits rapid turnover in vitro and in vivo, with a half-life in the range of 1-2 hours. Consistent with these characteristics, we find that after 4 hours of incubation in medium, nearly 100% of TMZ's cytotoxic activity has been spent (FIGS. 26A-26C). In contrast, TMZ-POH appears significantly longer-lived, where after 4 hours about 50% activity remains (FIGS. 26A-26C). Thus, while not wishing to be bound by any particular theory, we propose that the extended presence of TMZ-POH may provide for greater opportunity to set DNA lesions, resulting in increased cytotoxicity.

Figure 27B:
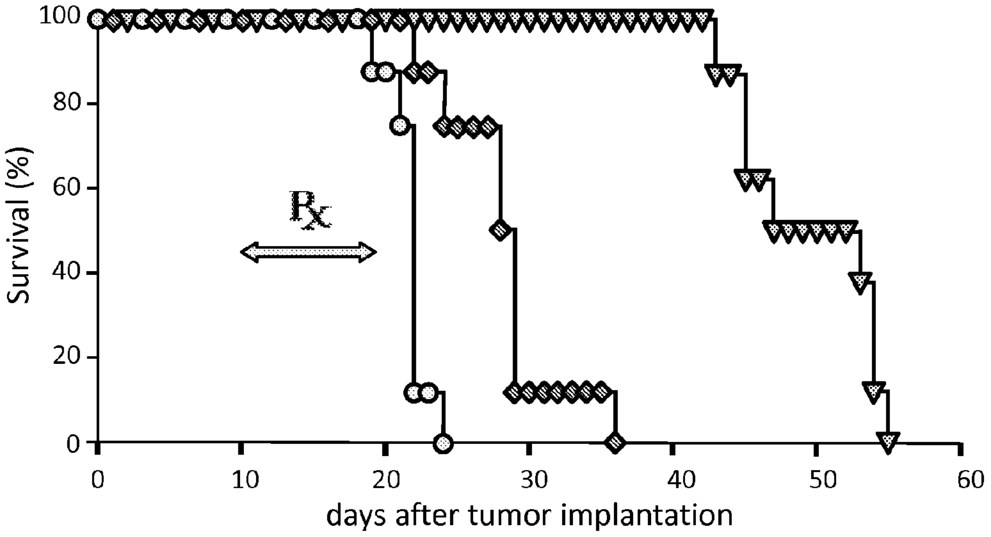

While the extended half-life of TMZ-POH may suffice to explain its greater potency in vitro, it remains to be established whether it also contributes to its substantially increased in vivo potency in our brain metastasis model (FIGS. 27A-27B). Because the lipophilicity of TMZ-POH is increased over TMZ (data not shown), it is also possible that TMZ-POH may cross the BBB more efficiently than TMZ. In the case of TMZ, it is known that drug levels achieved in the cerebrospinal fluid (CSF) are 80% lower than drug levels in the systemic circulation, i.e., in plasma. It is therefore conceivable that TMZ, despite its established therapeutic benefit, would exert even greater activity, if only higher intracranial concentrations could be achieved. In this regard, TMZ-POH might be the vehicle to achieve this.

It is quite intriguing that TMZ displayed only minor activity in our intracranial in vivo model (FIGS. 27A-27B). The breast cancer cell line we used, a variant of MDA-MB-231, does exhibit exquisite in vitro sensitivity to TMZ (IC50<10 μM), and therefore is more sensitive to TMZ than most MGMT-negative GBM cell lines reported in the literature and inclusive of several GBM cell lines we analyzed in parallel (data not shown). As well, the TMZ dosage used (25 mg/kg) is well within the range of dosages shown to exert potent activity in GBM mouse models, where even 5 mg/kg has significant activity. T. C. Chen et al. Green tea epigallocatechin gallate enhances therapeutic efficacy of temozolomide in orthotopic mouse glioblastoma models, *Cancer Lett* 302 (2011) 100-108. We therefore speculate that this triple-negative 231 cell line might harbor intrinsic mechanisms of resistance to TMZ that emerge only in the in vivo environment, and perhaps are reflective of the unimpressive responses that were noted when breast cancer patients with brain metastases were treated with TMZ. While this conjecture remains hypothetical at this time, it is obvious from our studies that TMZ-POH provides far superior therapeutic benefit than TMZ in our intracranial tumor model (FIGS. 27A-27B), which may bode well for the clinical setting.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

The invention claimed is:

1. A method for treating a brain metastasis of a breast cancer in a mammal, comprising administering to the mammal a therapeutically effective amount of a compound comprising perillyl alcohol (POH) conjugated with temozolomide (TMZ).

2. The method of claim 1, wherein the compound is 3-methyl 4-oxo-3,4-dihydroimidazo[5,1-d] [1,2,3,5]tetrazine-8-carbonyl-carbamic acid-4-isopropenyl cyclohex-1-enylmethyl ester (TMZ-POH).

3. The method of claim 1, wherein the compound is administered by inhalation, intranasally, orally, intravenously, subcutaneously or intramuscularly.

4. The method of claim 1, wherein the compound is administered intranasally using a nasal delivery device selected from the group consisting of an intranasal inhaler, an intranasal spray device, an atomizer, a nebulizer, a metered dose inhaler (MDI), a pressurized dose inhaler, an insufflator, a unit dose container, a pump, a dropper, a nasal spray bottle, a squeeze bottle and a bidirectional device.

5. The method of claim 1, further comprising treating the mammal with radiation before, during, or after the administration of the compound.

6. The method of claim 1, further comprising delivering to the mammal an additional chemotherapeutic agent.

7. A method for treating metastatic breast cancer in a mammal that has spread to the brain of the mammal, comprising administering to the mammal a therapeutically effective amount of 3-methyl 4-oxo-3,4-dihydroimidazo[5,1-d] [1,2,3,5]tetrazine-8-carbonyl-carbamic acid-4-isopropenyl cyclohex-1-enylmethyl ester (TMZ-POH).

* * * * *

UNITED STATES PATENT AND TRADEMARK OFFICE

CERTIFICATE OF CORRECTION

PATENT NO. : 9,913,838 B2
APPLICATION NO. : 15/026649
DATED : March 13, 2018
INVENTOR(S) : Thomas Chen It is certified that error appears in the above-identified patent and that said Letters Patent is hereby corrected as shown below:

In the Specification

After the "CROSS REFERENCE TO RELATED APPLICATIONS" Column 1, Line 22, insert as follows:
-- STATEMENT OF GOVERNMENT SUPPORT
This invention was made with government support under CA217551 awarded by the National Institutes of Health. The government has certain rights in the invention. --

Signed and Sealed this
Twenty-seventh Day of May, 2025

Coke Morgan Stewart
*Acting Director of the United States Patent and Trademark Office*